(12) United States Patent
Li et al.

(10) Patent No.: US 6,780,626 B2
(45) Date of Patent: Aug. 24, 2004

(54) ISOLATED HUMAN KINASE PROTEINS, NUCLEIC ACID MOLECULES ENCODING HUMAN KINASE PROTEINS, AND USES THEREOF

(75) Inventors: Jiayin Li, Potomac, MD (US); Karl Guegler, Menlo Park, CA (US); Ellen M. Beasley, Darnestown, MD (US); Karen A. Ketchum, Germantown, MD (US); Valentina Di Francesco, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/339,657

(22) Filed: Jan. 10, 2003

(65) Prior Publication Data

US 2003/0129645 A1 Jul. 10, 2003

Related U.S. Application Data

(62) Division of application No. 10/060,332, filed on Feb. 1, 2002, now Pat. No. 6,528,294, which is a division of application No. 09/735,934, filed on Dec. 14, 2000, now Pat. No. 6,372,468.
(60) Provisional application No. 60/232,633, filed on Sep. 14, 2000, now abandoned.

(51) Int. Cl.$^7$ ............................ C12N 9/12; C12N 1/20; C12N 15/00; C12N 5/00; C07H 21/04
(52) U.S. Cl. .................... 435/194; 435/320.1; 435/325; 435/252.3; 536/23.2
(58) Field of Search ............................. 435/194, 252.3, 435/320.1, 325; 536/23.2

(56) References Cited

U.S. PATENT DOCUMENTS

2004/0018185 A1 * 1/2004 Yue et al. .................. 424/94.5

FOREIGN PATENT DOCUMENTS

| WO | WO 99 20747 A | 4/1999 |
| WO | WO 00 73469 A | 12/2000 |
| WO | WO 01 54733 A | 8/2001 |

OTHER PUBLICATIONS

Wilson et al. "2.2 MB of Contiguous Nucleotide Sequence from Chromosome III of C. Elegans." Nature, London, GB. vol. 368, No. 6466. Mar. 3, 1994, pp. 32–38 XP002029739.

Matsuoka et al. "Linkage of ATM to Cell Cycle Regulation by the CHK2 Protein Kinase." Science. American Association for the Advancement of Science. vol. 282. Dec. 4, 1998, pp. 1893–1897. XP002922301.

Chaturvedi et al. "Mammalian CHK2 is a Downstream Effector of the ATM–Dependent DNA Damage Checkpoint Pathway." Oncogene. Hant, GB. vol. 18, No. 28, Jul. 15, 1999, pp. 4047–4054. XP001025153.

International Search report published Aug. 29, 2002 with publication of International Application.

* cited by examiner

Primary Examiner—Maryam Monshipouri
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

12 Claims, 42 Drawing Sheets

```
   1 ATGGCCACCG CCCCCTCTTA TCCCGCCGGG CTCCCTGGCT CTCCCGGGCC
  51 GGGGTCTCCT CCGCCCCCCG GCGGCCTAGA GCTGCAGTCG CCGCCACCGC
 101 TACTGCCCCA GATCCCGGCC CCGGGTTCCG GGGTCTCCTT TCACATCCAG
 151 ATCGGGCTGA CCCGCGAGTT CGTGCTGTTG CCCGCCGCCT CCGAGCTGGC
 201 TCATGTGAAG CAGCTGGCCT GTTCCATCGT GGACCAGAAG TTCCCTGAGT
 251 GTGGCTTCTA CGGCCTTTAC GACAAGATCC TGCTTTTCAA ACATGACCCC
 301 ACGTCGGCCA ACCTCCTGCA GCTGGTGCGC TCGTCCGGAG ACATCCAGGA
 351 GGGCGACCTG GTGGAGGTGG TGCTGTCGGC CTCGGCCACC TTCGAGGACT
 401 TCCAGATCCG CCCGCACGCC CTCACGGTGC ACTCCTATCG GGCGCCTGCC
 451 TTCTGTGATC ACTGCGGGGA GATGCTCTTC GGCCTAGTGC GCCAGGGCCT
 501 CAAGTGCGAT GGCTGCGGGC TGAACTACCA CAAGCGCTGT GCCTTCAGCA
 551 TCCCCAACAA CTGTAGTGGG GCCCGCAAAC GGCGCCTGTC ATCCACGTCT
 601 CTGGCCAGTG CCACTCGGT GCGCCTCGGC ACCTCCGAGT CCCTGCCCTG
 651 CACGGCTGAA GAGCTGAGCC GTAGCACCAC CGAACTCCTG CCTCGCCGTC
 701 CCCCGTCATC CTCTTCCTCC TCTTCTGCCT CATCGTATAC GGGCCGCCCC
 751 ATTGAGCTGG ACAAGATGCT GCTCTCCAAG GTCAAGGTGC CGCACACCTT
 801 CCTCATCCAC AGCTATACAC GGCCCACCGT TTGCCAGGCT TGCAAGAAAC
 851 TCCTCAAGGG CCTCTTCCGG CAGGGCCTGC AATGCAAAGA CTGCAAGTTT
 901 AACTGTCACA AACGCTGCGC CACCCGCGTC CCTAATGACT GCCTGGGGGA
 951 GGCCCTTATC AATGGAGATG TGCCGATGGA GGAGGCCACC GATTTCAGCG
1001 AGGCTGACAA GAGCGCCCTC ATGGATGAGT CAGAGGACTC CGGTGTCATC
1051 CCTGGCTCCC ACTCAGAGAA TGCGCTCCAC GCCAGTGAGG AGGAGGAAGG
1101 CGAGGGAGGC AAGGCCCAGA GCTCCCTGGG GTACATCCCC CTAATGAGGG
1151 TGGTGCAATC GGTGCGACAC ACGACGCGGA AATCCAGCAC CACGCTGCGG
1201 GAGGGTTGGG TGGTTCATTA CAGCAACAAG GACACGCTGA GAAAGCGGCA
1251 CTATTGGCGC CTGGACTGCA AGTGTATCAC GCTCTTCCAG AACAACACGA
1301 CCAACAGATA CTATAAGGAA ATTCCGCTGT CAGAAATCCT CACGGTGGAG
1351 TCCGCCCAGA ACTTCAGCCT TGTGCCGCCG GGCACCAACC CACACTGCTT
1401 TGAGATCGTC ACTGCCAATG CCACCTACTT CGTGGGCGAG ATGCCTGGCG
1451 GGACTCCGGG TGGGCCAAGT GGGCAGGGGG CTGAGGCCGC CCGGGGCTGG
1501 GAGACAGCCA TCCGCCAGGC CCTGATGCCC GTCATCCTTC AGGACGCACC
1551 CAGCGCCCCA GGCCACGCGC CCACAGACA AGCTTCTCTG AGCATCTCTG
1601 TGTCCAACAG TCAGATCCAA GAGAATGTGG ACATTGCCAC TGTCTACCAG
1651 ATCTTCCCTG ACGAAGTGCT GGGCTCAGGG CAGTTTGGAG TGGTCTATGG
1701 AGGAAAACAC CGGAAGACAG GCCGGGACGT GGCAGTTAAG GTCATTGACA
1751 AACTGCGCTT CCCTACCAAG CAGGAGAGCC AGCTCCGGAA TGAAGTGGCC
1801 ATTCTGCAGA GCCTGCGGCA TCCCGGGATC GTGAACCTGG AGTGCATGTT
1851 CGAGACGCCT GAGAAAGTGT TTGTGGTGAT GGAGAAGCTG CATGGGGACA
1901 TGTTGGAGAT GATCCTGTCC AGTGAGAAGG GCCGGCTGCC TGAGCGCCTC
1951 ACCAAGTTCC TCATCACCCA GATCCTGGTG GCTTTGAGAC ACCTTCACTT
2001 CAAGAACATT GTCCACTGTG ACTTGAAACC AGAAACGTG TTGCTGGCAT
2051 CAGCAGACCC ATTTCCTCAG GTGAAGCTGT GTGACTTTGG CTTTGCTCGC
2101 ATCATCGGCG AGAAGTCGTT CCGCCGCTCA GTGGTGGGCA CGCCGGCCTA
2151 CCTGGCACCC GAGGTGCTGC TCAACCAGGG CTACAACCGC TCGCTGGACA
2201 TGTGGTCAGT GGGCGTGATC ATGTACGTCA GCCTCAGCGG CACCTTCCCT
2251 TTCAACGAGG ATGAGGACAT CAATGACCAG ATCCAGAACG CCGCCTTCAT
```

FIGURE 1A

```
2301 GTACCCGGCC AGCCCCTGGA GCCACATCTC AGCTGGAGCC ATTGACCTCA
2351 TCAACAACCT GCTGCAGGTG AAGATGCGCA AACGCTACAG CGTGGACAAA
2401 TCTCTCAGCC ACCCCTGGTT ACAGGAGTAC CAGACGTGGC TGGACCTCCG
2451 AGAGCTGGAG GGGAAGATGG GAGAGCGATA CATCACGCAT GAGAGTGACG
2501 ACGCGCGCTG GGAGCAGTTT GCAGCAGAGC ATCCGCTGCC TGGGTCTGGG
2551 CTGCCCACGG ACAGGGATCT CGGTGGGGCC TGTCCACCAC AGGACCACGA
2601 CATGCAGGGG CTGGCGGAGC GCATCAGTGT TCTCTGA (SEQ ID NO:1)
```

FEATURES:
Start Codon: 1
Stop Codon: 2635
3'UTR: 2638

Homologous proteins:
Top 10 BLAST Hits

|  | Score | E |
|---|---|---|
| gi\|4506075\|ref\|NP_002733.1\| protein kinase C, mu [Homo sapiens]... | 1225 | 0.0 |
| gi\|6679351\|ref\|NP_032884.1\| protein kinase C, mu [Mus musculus]... | 1219 | 0.0 |
| gi\|11433471\|ref\|XP_007234.1\| protein kinase C, mu [Homo sapiens] | 1148 | 0.0 |
| gi\|5031689\|ref\|NP_005804.1\| protein kinase C, nu; serine-threon... | 1129 | 0.0 |
| gi\|7434268\|pir\|\|T08777 probable protein kinase C (EC 2.7.1.-) m... | 1113 | 0.0 |
| gi\|7508444\|pir\|\|T20881 hypothetical protein T25E12.4a - Caenorh... | 783 | 0.0 |
| gi\|11424892\|ref\|XP_009034.1\| hypothetical protein [Homo sapiens] | 543 | e-153 |
| gi\|7509169\|pir\|\|T26297 hypothetical protein W09C5.5 - Caenorhab... | 506 | e-142 |
| gi\|7705493\|ref\|NP_057541.1\| DKFZP586E0820 protein; hypothetical... | 445 | e-135 |
| gi\|4996218\|dbj\|BAA78373.1\| (AB020616) PKC mu [Rattus norvegicus] | 274 | 4e-72 |

BLAST to dbEST:

|  | Score | E |
|---|---|---|
| gi\|9138571 /dataset=dbest /taxon=9606... | 1221 | 0.0 |
| gi\|6920751 /dataset=dbest /taxon=960... | 934 | 0.0 |
| gi\|8909831 /dataset=dbest /taxon=9606... | 880 | 0.0 |
| gi\|2111489 /dataset=dbest /taxon=9606 ... | 823 | 0.0 |
| gi\|3959429 /dataset=dbest /taxon=9606 ... | 819 | 0.0 |
| gi\|2355835 /dataset=dbest /taxon=9606 ... | 807 | 0.0 |
| gi\|7540197 /dataset=dbest /taxon=9606... | 799 | 0.0 |
| gi\|8365632 /dataset=dbest /taxon=9606... | 757 | 0.0 |
| gi\|2206813 /dataset=dbest /taxon=9606 ... | 757 | 0.0 |
| gi\|3924014 /dataset=dbest /taxon=9606 ... | 749 | 0.0 |

EXPRESSION INFORMATION FOR MODULATORY USE:
library source:
Expression information from BLAST dbEST hits:
gi\|9138571  Lung
gi\|6920751  Lymph

FIGURE 1B gi|8909831  Carcinoid lung
gi|2111489  Ovary tumor
gi|3959429  Kidney
gi|2355835  Colon
gi|7540197  Cervix
gi|8365632  Kidney
gi|2206813  Ovary tumor
gi|3924014  Lymph node (mantle cell lymphoma)

Expression information from PCR-based tissue screening panels:
Human bone marrow
Human brain
Human colon
Human fetal brain
Human fetal heart
Human kidney
Human fetal lung
Human fetal liver
Human heart
Human kidney
Human lung
Human uterus
Human pancreas

FIGURE 1C

```
  1 MATAPSYPAG LPGSPGPGSP PPPGGLELQS PPPLLPQIPA PGSGVSFHIQ
 51 IGLTREFVLL PAASELAHVK QLACSIVDQK FPECGFYGLY DKILLFKHDP
101 TSANLLQLVR SSGDIQEGDL VEVVLSASAT FEDFQIRPHA LTVHSYRAPA
151 FCDHCGEMLF GLVRQGLKCD GCGLNYHKRC AFSIPNNCSG ARKRRLSSTS
201 LASGHSVRLG TSESLPCTAE ELSRSTTELL PRRPPSSSSS SSASSYTGRP
251 IELDKMLLSK VKVPHTFLIH SYTRPTVCQA CKKLLKGLFR QGLQCKDCKF
301 NCHKRCATRV PNDCLGEALI NGDVPMEEAT DFSEADKSAL MDESEDSGVI
351 PGSHSENALH ASEEEEGEGG KAQSSLGYIP LMRVVQSVRH TTRKSSTTLR
401 EGWVVHYSNK DTLRKRHYWR LDCKCITLFQ NNTTNRYYKE IPLSEILTVE
451 SAQNFSLVPP GTNPHCFEIV TANATYFVGE MPGGTPGGPS GQGAEAARGW
501 ETAIRQALMP VILQDAPSAP GHAPHRQASL SISVSNSQIQ ENVDIATVYQ
551 IFPDEVLGSG QFGVVYGGKH RKTGRDVAVK VIDKLRFPTK QESQLRNEVA
601 ILQSLRHPGI VNLECMFETP EKVFVVMEKL HGDMLEMILS SEKGRLPERL
651 TKFLITQILV ALRHLHFKNI VHCDLKPENV LLASADPFPQ VKLCDFGFAR
701 IIGEKSFRRS VVGTPAYLAP EVLLNQGYNR SLDMWSVGVI MYVSLSGTFP
751 FNEDEDINDQ IQNAAFMYPA SPWSHISAGA IDLINNLLQV KMRKRYSVDK
801 SLSHPWLQEY QTWLDLRELE GKMGERYITH ESDDARWEQF AAEHPLPGSG
851 LPTDRDLGGA CPPQDHDMQG LAERISVL (SEQ ID NO:2)
```

FEATURES:
Functional domains and key regions:
[1] PDOC00001 PS00001 ASN_GLYCOSYLATION
N-glycosylation site Number of matches: 6
    1    187-190 NCSG
    2    431-434 NNTT
    3    432-435 NTTN
    4    454-457 NFSL
    5    473-476 NATY
    6    729-732 NRSL

[2] PDOC00004 PS00004 CAMP_PHOSPHO_SITE
cAMP- and cGMP-dependent protein kinase phosphorylation site Number of matches: 3
    1    194-197 RRLS
    2    393-396 RKSS
    3    794-797 KRYS

[3] PDOC00005 PS00005 PKC_PHOSPHO_SITE
Protein kinase C phosphorylation site

Number of matches: 15
    1    145-147 SYR
    2    206-208 SVR

FIGURE 2A

```
 3    387-389 SVR
 4    247-249 TGR
 5    573-575 TGR
 6    206-208 SVR
 7    387-389 SVR
 8    391-393 TTR
 9    392-394 TRK
10    398-400 TLR
11    412-414 TLR
12    408-410 SNK
13    398-400 TLR
14    412-414 TLR
15    434-436 TNR
```

[4] PDOC00006 PS00006 CK2_PHOSPHO_SITE
Casein kinase II phosphorylation site

```
Number of matches: 14
     1    75-78  SIVD
     2   111-114 SSGD
     3   130-133 TFED
     4   218-221 TAEE
     5   225-228 STTE
     6   333-336 SEAD
     7   353-356 SHSE
     8   362-365 SEEE
     9   398-401 TLRE
    10   408-411 SNKD
    11   573-576 TGRD
    12   589-592 TKQE
    13   812-815 TWLD
    14   853-856 TDRD
```

[5] PDOC00007 PS00007 TYR_PHOSPHO_SITE
Tyrosine kinase phosphorylation site

```
         80-87 KFPECGFY
```

[6] PDOC00008 PS00008 MYRISTYL
N-myristoylation site

```
Number of matches: 8
     1    42-47  GSGVSF
     2   171-176 GCGLNY
     3   210-215 GTSESL
     4   348-353 GVIPGS
```

FIGURE 2B

```
    5    483-488  GGTPGG
    6    487-492  GGPSGQ
    7    493-498  GAEAAR
    8    563-568  GVVYGG
```

[7] PDOC00379 PS00479 DAG_PE_BIND_DOM_1
Phorbol esters / diacylglycerol binding domain

```
Number of matches: 2
    1    139-188  HALTVHSYRAPAFCDHCGEMLFGLVRQGLKCDGCGLNYHKRCAFSIPNNC
    2    265-314  HTFLIHSYTRPTVCQACKKLLKGLFRQGLQCKDCKFNCHKRCATRVPNDC
```

[8] PDOC00100 PS00107 PROTEIN_KINASE_ATP
Protein kinases ATP-binding region signature

```
        557-580  LGSGQFGVVYGGKHRKTGRDVAVK
```

[9] PDOC00100 PS00108 PROTEIN_KINASE_ST
Serine/Threonine protein kinases active-site signature

```
        670-682  IVHCDLKPENVLL
```

Membrane spanning structure and domains:

| Helix | Begin | End | Score | Certainty |
|---|---|---|---|---|
| 1 | 5 | 25 | 0.757 | Putative |
| 2 | 40 | 60 | 0.765 | Putative |
| 3 | 738 | 758 | 1.560 | Certain |
| 4 | 767 | 787 | 0.860 | Putative |

BLAST Alignment to Top Hit:
>gi|4506075|ref|NP_002733.1| protein kinase C, mu [Homo sapiens]
sp|Q15139|KPCM_HUMAN PROTEIN KINASE C, MU TYPE (NPKC-MU)
pir||A53215 protein kinase C (EC 2.7.1.-) mu precursor - human
emb|CAA53384.1| (X75756) protein kinase C mu [Homo sapiens]
        Length = 912

Score = 1225 bits (3134), Expect = 0.0
Identities = 625/918 (68%), Positives = 717/918 (78%), Gaps = 41/918 (4%)
Frame = +1

```
Query:  4   ATAPSYPAGLPGSPGPGSPPPPGGLELQSPPPLLPQIPAPGSGVSFHIQIGLTREFVLLP  183
            A A +  A +PGS GPG              P P L  + AP  G+SFH+QIGL+RE VLL
Sbjct: 19   AAAAAAAALVPGS-GPG------------PAPFLAPVAAPVGGISFHLQIGLSREPVLLL  65
```

FIGURE 2C

```
Query:  184  AASE----LAHVKQLACSIVDQKFPECGFYGLYDKILLFKHDPTSANLLQLVRSSGDIQE  351
             S       LAHV+++ACSIVDQKFPECGFYG+YDKILLF+HDPTS N+LQLV+++ DIQE
Sbjct:   66  QDSSGDYSLAHVREMACSIVDQKFPECGFYGMYDKILLFRHDPTSENILQLVKAASDIQE  125

Query:  352  GDLVEVVLSASATFEDFQIRPHALTVHSYRAPAFCDHCGEMLFGLVRQGLKCDGCGLNYH  531
             GDL+EVVLS SATFEDFQIRPHAL VHSYRAPAFCDHCGEML+GLVRQGLKC+GCGLNYH
Sbjct:  126  GDLIEVVLSRSATFEDFQIRPHALFVHSYRAPAFCDHCGEMLWGLVRQGLKCEGCGLNYH  185

Query:  532  KRCAFSIPNNCSGARKRRLSSTSLASGHSVRLGTSESLPCTAEE--LSRSTTELLPRRPP  705
             KRCAF IPNNCSG R+RRLS+ SL     ++R ++E    +E  L +S +E    R
Sbjct:  186  KRCAFKIPNNCSGVRRRRLSNVSLTGVSTIRTSSAELSTSAPDEPLLQKSPSESFIGREK  245

Query:  706  SSSSSSSASSYTGRPIELDKMLLSKVKVPHTFLIHSYTRPTVCQACKKLLKGLFRQGLQC  885
             S+S S    Y GRPI LDK+L+SKVKVPHTF+IHSYTRPTVCQ CKKLLKGLFRQGLQC
Sbjct:  246  RSNSQS----YIGRPIHLDKILMSKVKVPHTFVIHSYTRPTVCQYCKKLLKGLFRQGLQC  301

Query:  886  KDCKFNCHKRCATRVPNDCLGEALINGD---------VPMEEATDFSEADK-SALMDESE  1035
             KDC+FNCHKRCA +VPN+CLGE  INGD         V MEE +D ++++ S LMD+ E
Sbjct:  302  KDCRFNCHKRCAPKVPNNCLGEVTINGDLLSPGAESDVVMEEGSDDNDSERNSGLMDDME  361

Query: 1036  DSGVIPGSHSENALHASEEEEGEGGKAQ---------------SSLGYIPLMRVVQSVRH  1170
             ++ V    ++A  A  E + + G+ Q                S+    IPLMRVVQSV+H
Sbjct:  362  EAMV------QDAEMAMAECQNDSGEMQDPDPDHEDANRTISPSTSNNIPLMRVVQSVKH  415

Query: 1171  TTRKSSTTLREGWVVHYSNKDTLRKRHYWRLDCKCITLFQNNTTNRYYKEIPLSEILTVE  1350
             T RKSST ++EGW+V+HY++KDTLRKRHYWRLD KCITLFQN+T +RYYKEIPLSEIL++E
Sbjct:  416  TKRKSSTVMKEGWMVHYTSKDTLRKRHYWRLDSKCITLFQNDTGSRYYKEIPLSEILSLE  475

Query: 1351  SAQNFSLVPPGTNPHCFEIVTANATYFVGEMPGGTPGGPS--------GQGAEAARGWET  1506
             +  +L+P G NPHCFEI TAN  Y+VGE    P  PS         G GA+ AR WE
Sbjct:  476  PVKTSALIPNGANPHCFEITTANVVYYVGENVVN-PSSPSPNNSVLTSGVGADVARMWEI  534

Query: 1507  AIRQALMPVILQDAPSAPGHAPHRQASLSISVSNSQIQENVDIATVYQIFPDEVLGSGQF  1686
             AI+ ALMPVI + +   G  HR  S+SISVSN QIQENVDI+TVYQIFPDEVLGSGQF
Sbjct:  535  AIQHALMPVIPKGSSVGTGTNLHRDISVSISVSNCQIQENVDISTVYQIFPDEVLGSGQF  594

Query: 1687  GVVYGGKHRKTGRDVAVKVIDKLRFPTKQESQLRNEVAILQSLRHPGIVNLECMFETPEK  1866
             G+VYGGKHRKTGRDVA+K+IDKLRFPTKQESQLRNEVAILQ+L HPG+VNLECMFETPE+
Sbjct:  595  GIVYGGKHRKTGRDVAIKIIDKLRFPTKQESQLRNEVAILQNLHHPGVVNLECMFETPER  654

Query: 1867  VFVVMEKLHGDMLEMILSSEKGRLPERLTKFLITQILVALRHLHFKNIVHCDLKPENVLL  2046
             VFVVMEKLHGDMLEMILSSEKGRLPE +TKFLITQILVALRHLHFKNIVHCDLKPENVLL
Sbjct:  655  VFVVMEKLHGDMLEMILSSEKGRLPEHITKFLITQILVALRHLHFKNIVHCDLKPENVLL  714
```

FIGURE 2D

```
Query: 2047 ASADPFPQVKLCDFGFARIIGEKSFRRSVVGTPAYLAPEVLLNQGYNRSLDMWSVGVIMY 2226
              ASADPFPQVKLCDFGFARIIGEKSFRRSVVGTPAYLAPEVL N+GYNRSLDMWSVGVI+Y
Sbjct:  715 ASADPFPQVKLCDFGFARIIGEKSFRRSVVGTPAYLAPEVLRNKGYNRSLDMWSVGVIIY  774

Query: 2227 VSLSGTFPFNEDEDINDQIQNAAFMYPASPWSHISAGAIDLINNLLQVKMRKRYSVDKSL 2406
              VSLSGTFPFNEDEDI+DQIQNAAFMYP +PW IS  AIDLINNLLQVKMRKRYSVDK+L
Sbjct:  775 VSLSGTFPFNEDEDIHDQIQNAAFMYPPNPWKEISHEAIDLINNLLQVKMRKRYSVDKTL  834

Query: 2407 SHPWLQEYQTWLDLRELEGKMGERYITHESDDARWEQFAAEHPL--PGSGLPTDRDLGGA 2580
              SHPWLQ+YQTWLDLRELE K+GERYITHESDD RWE++A E  L P   +
Sbjct:  835 SHPWLQDYQTWLDLRELECKIGERYITHESDDLRWEKYAGEQRLQYPTHLINPSASHSDT  894

Query: 2581 CPPQDHDMQGLAERISVL 2634
              ++ +M+ L ER+S+L
Sbjct:  895 PETEETEMKALGERVSIL  912 (SEQ ID NO:4)
```

Hmmer search results (Pfam):

| Model | Description | Score | E-value | N |
|---|---|---|---|---|
| PF00069 | Eukaryotic protein kinase domain | 263.2 | 3.4e-75 | 1 |
| PF00130 | Phorbol esters/diacylglycerol binding domain | 137.2 | 3e-37 | 2 |
| CE00022 | CE00022 MAGUK_subfamily_d | 94.6 | 8.1e-28 | 2 |
| PF00169 | PH domain | 34.9 | 2.3e-08 | 1 |
| CE00031 | CE00031 VEGFR | 3.7 | 0.31 | 1 |
| CE00287 | CE00287 PTK_Eph_orphan_receptor | -48.0 | 3.6e-05 | 1 |
| CE00292 | CE00292 PTK_membrane_span | -73.8 | 0.00011 | 1 |
| CE00289 | CE00289 PTK_PDGF_receptor | -78.2 | 5.1 | 1 |
| CE00286 | E00286 PTK_EGF_receptor | -85.0 | 6.5e-06 | 1 |
| CE00291 | CE00291 PTK_fgf_receptor | -111.3 | 0.022 | 1 |
| CE00016 | CE00016 GSK_glycogen_synthase_kinase | -168.8 | 2.7e-07 | 1 |
| CE00290 | CE00290 PTK_Trk_family | -171.4 | 0.0018 | 1 |
| CE00288 | CE00288 PTK_Insulin_receptor | -231.1 | 0.53 | 1 |

Parsed for domains:

| Model | Domain | seq-f | seq-t | hmm-f | hmm-t | | score | E-value |
|---|---|---|---|---|---|---|---|---|
| PF00130 | 1/2 | 139 | 188 .. | 1 | 51 | [] | 66.5 | 4.7e-16 |
| PF00130 | 2/2 | 265 | 314 .. | 1 | 51 | [] | 78.6 | 1.3e-19 |
| PF00169 | 1/1 | 398 | 478 .. | 1 | 65 | [. | 34.9 | 2.3e-08 |
| CE00022 | 1/2 | 555 | 614 .. | 21 | 83 | .. | 2.3 | 1.4 |
| CE00289 | 1/1 | 554 | 641 .. | 1 | 109 | [] | -78.2 | 5.1 |
| CE00031 | 1/1 | 671 | 742 .. | 1068 | 1139 | .. | 3.7 | 0.31 |
| CE00292 | 1/1 | 551 | 780 .. | 1 | 288 | [] | -73.8 | 0.00011 |
| CE00288 | 1/1 | 551 | 784 .. | 1 | 269 | [] | -231.1 | 0.53 |
| CE00286 | 1/1 | 551 | 787 .. | 1 | 263 | [] | -85.0 | 6.5e-06 |
| CE00291 | 1/1 | 555 | 787 .. | 1 | 285 | [] | -111.3 | 0.022 |

FIGURE 2E

| CE00290 | 1/1 | 551 | 788 | .. | 1 | 282 | [] | -171.4 | 0.0018 |
| CE00287 | 1/1 | 551 | 805 | .. | 1 | 260 | [] | -48.0 | 3.6e-05 |
| PF00069 | 1/1 | 551 | 807 | .. | 1 | 278 | [] | 263.2 | 3.4e-75 |
| CE00022 | 2/2 | 657 | 809 | .. | 129 | 285 | .. | 92.2 | 4e-27 |
| CE00016 | 1/1 | 471 | 872 | .. | 1 | 433 | [] | -168.8 | 2.7e-07 |

FIGURE 2F

```
   1 CGCGGCGGGG AGGGCAGGGG TGACGCTCGG AGAACAGAGA GGCCGAACCC
  51 AGAGAGCGGG CCGGGACCTG ATACCGATTT CCCACCCGTC CCCTGCCATG
 101 GGCGCCGGAC GCCTGCCGGA GAGGGCTCCC CTCCTTAAAG GGCCAGTGGC
 151 CTCCAAGCCC GACGCCTGCG ACCGGCGGTG GGTGATAGTG TTTCCCCTCC
 201 CTGTCCAGCC GAGGGAAAAG TTAACTTTCC AGGCTTGGCT GTGTTCAGGG
 251 AAGGAACTGG TCTCGCCTGC CTGCCCTCCA TCCCTCACAC CATCCCTTGT
 301 CCCGGACCCT GGAGGCGGAG GTCCAGCCCC CAACTCGGAG GCCCCGGGCC
 351 CACCCTCCCC TTCCGCCCCC GGCCCCTCGG CAGGCTCCGC CCCTCTCTGA
 401 CGTCGCCGAG GCCCGCGCCG ATTGGTCGAC TGCACTGTCG CTCCGGACAC
 451 TTCCTCCTGG GCCGCCGCCG CCGCCGCCGA CTTAAACTTT GGAGGGGGAA
 501 AAAGAGCTAC TGGCGCCTGG CGACCCTCCC TGCCCCCCAC CCAACCCCGC
 551 TCCGGCAACG CCCCCTTCCT CACGGCTCCC GACCGAACTT TTCTCCAACT
 601 TCTGCGACTC GTGAGATTCC CTTCTACCCA CTCCGGCCCT CGGGACCCCT
 651 CTGCCCATCC CCTGGCCGGT CGGGTCCCTG CGAACCCCTT TATCTCTGGA
 701 ATCCACTCGG TCCCCGACTC AGAGACTCCT GCCCTCCACC CCCAAGGTGA
 751 ATTCCCCCGG GCCGCCTTCT GAGTGGGATC CTCTTCTTGG AGCACTGGAT
 801 CCTGGGATTC CCTCTGCCCC CTTCTCAATC CCTCCTCTAG GGAAGGGGCC
 851 TTTGAATCGC GGGCTCTCCT GATCCCTGTG ACCCCGACCT ACTAGATTTC
 901 CTCTCAGGCT TCTTGGAATC TCAATCGCTG GGACCTCCAA CCCACTACTT
 951 TTCTCCTTTC TGATCTTCTG GGAGCCCTGG ATTCCGGGCC TCTGACCCAC
1001 TATAGTGCCT TTCTCTCCTT CCCAGGACCC CGCCATCCTC AGGTCCCCTC
1051 CGCCTGCCAG ATCTTTTCTC GGATCCCCGC TCTCCCACCA CCTGCTCACG
1101 AGATCCCGCG GATCTAGAAC CCAGGGTCCC CCGGGGCCCC CCGGCCGGGT
1151 CCCGGGTGGG CTCCAGGCGG CCGGTCCCCG GCCTCCCCCC ATGGCCACCG
1201 CCCCCTCTTA TCCCGCCGGG CTCCCTGGCT CTCCCGGGCC GGGGTCTCCT
1251 CCGCCCCCCG GCGGCCTAGA GCTGCAGTCG CCGCCACCGC TACTGCCCCA
1301 GATCCCGGCC CCGGGTTCCG GGTCTCCTT  TCACATCCAG ATCGGGCTGA
1351 CCCGCGAGTT CGTGCTGTTG CCCGCCGCCT CCGAGCTGGC TCATGTGAAG
1401 CAGCTGGCCT GTTCCATCGT GGACCAGAAG GTGAGGGCGC AGGCTCCCTG
1451 GATCCAGCTC GGGGAGAGGT TGAAGGAGGG GGCGCTGGCA GAGGGGTCTG
1501 GGGCCTGGTG TGCGGAAGAG GGAGGAAGGA GACCTGAGCT TTGGGTGATG
1551 GAGGGATAGG GGGCATTGCC CCCCTTCCAT TGCCCCTCTC CCCACCATCC
1601 CTTTGAGAGA GGACTGGGCA GGGGTGGGGT GCCCCAGAGG CCTCCCCAAA
1651 TTTCATGTCC CTGCATGTCG TTGTTTTCTG CAGCAAACAG GGAGGAAGGG
1701 AGGGGCCAGC CAGGTGTAGA GAGGGGAGGA AGGGGCAGCA GATGTCGGCG
1751 GACCTCCACG TCCAGGCCCA TCCCGGGCCT CCCATTTGGT GGAAACAGGA
1801 GAAATTGAAC CCGGGCTGGC CATGGTGATC CGGTGACATG TGTGGGTGCA
1851 GGTGCTTGAG TTAGCTGCCA GGGCAAGTG  AGGTCTCGGA GCCCAATTCT
1901 GCCCTCCCCT AAGCCTGAGA TATGTGTGGA GGGGCAGGCA CTCCTACAGA
1951 CCCTGGGGAC TCTATTCCCT TTCCTAGTCA CAGTGCTGTT AGCCTACTCT
2001 TAATTTTGGA CACCAGGGTC CCCAGGGTGG GCAGCTGGGT GTTATGGCAA
2051 GAGGAAACCA GGTGGAACTC CACGTCTAAA CCGTGAAATG TTAAAAGAAT
2101 AGTGGGCTTC TGTGTTGGAG TACTGGACTG TAGAAATGTT AGAATATTAG
2151 AATCATAACT TGTTGGAATA TGCATCCTAG GCAATTAAAT TGCCCCCATG
2201 TTCGTGTTCA AATATTAGAA TTCTAGGTTT GTGAAATAGT AAAACATTAA
2251 AATGCTGGAA TATTAGATTC CTAGATTGTT GAATCCTAGA AAGTTAAAAT
```

FIGURE 3A

```
2301 GTTAGAATTT TAGAATGCTG GATGGATGAG GTCCTTGAAT GCTAAAGAAT
2351 TCAAAGAGCA CAGTCCTAGC TTGTCAGACT CCTAGAATAT TAAAATATTA
2401 GATTACCGCT TATTTAGGTT ATTGAAATCC TAAAATGTAT AGTGATACCA
2451 GGTAGGAATC TAGAATGTAT AATTCTATAA TGTGAGCATG TTGGAGTCCC
2501 AAAATATCCA AATTCCAGAA TCTTTTCAGA CTCCTGGAAA TGAATCCTTT
2551 GGGCATCAGA GAAACGTGGG GAACTGGGCC AGCTCCCCCA TTCTACAGAC
2601 AAGGAAACTG AAGCTTAGAG AAAAACTTCC CAAGGGGTCA GGGCCAAGGC
2651 AGTCCTGGTC TTCTGTGGAC TCTCTCTTAG CAGTGAGAAC TGATAGGGTT
2701 TTGCCCACCA AATGCCTAAA TCCCGCAGGC CCAGCTCACC ACCCCAACTC
2751 AGCCCACTTC ATGGGAAGCT GGTGGCAGTG GGGTACGGG GGCAGATTGT
2801 CCCTTGGGTG AACTTCTTTG TCCAGTGCTC AAGTCCCCAG CCTGCCCCGC
2851 TCAGGCTTCA CCCCAGTTTT ATTTTTCTGC CAGGTCCAGG TGTGTTAGGG
2901 CCGCGTACCT TCCTTCCCGA GGCCCCACCG GGGCAGTTTC ACTTTCTGTT
2951 CTACTAGGTT TCATTTCCTG CCCCCAGGCC CCCAAAGCTG AGGACCCAGA
3001 CACCTGGGTC CTTTGAGCAT TGGGTGGCAG GCGCCCTCCT TATCTCCAGC
3051 GCCCTCGAGT CCAAGTCCCC CGGCCCCCC CCCCACTTT CCCAGGAGCC
3101 CCGAAAAGTC CTCCTTCCAG CTCGCCCAC CCCAGTGCTG GGCCTGGAGC
3151 CAGGTAACTG GGACAACAAT AGACAGATCC AGGAAGGAAG CTGGGGGGCG
3201 GGTGTGTGAG CCTGGGGAGG AGGCACAGGG GAGGGAGTGT TCATTCAGCA
3251 TCCCCTCCCA CCTCCGCCAG GTTCCGGAAA ATTCGAGGTG TCCACGCTCC
3301 CGGAGCCACT CTCCCTCCCA CCCCAGCTCC CCCTTCCAGC CACCAAACCC
3351 ACGCCGGCGC CCCCTCCCCG TACAATTGGG GCGCTGGCAT CCTGCCCGGC
3401 TCGCGCTGGG GTTGGGAGGG GGCAGGCAGG AAGCGAGGGC CTGCGGGGTC
3451 TCTGCGTTTC CGGGGGAAAC AGCCGGCCCT GCCCTGGGAG GGTCACAGTC
3501 CGCCCGCTGC TGAAGGCGGC TCTGAGCTTT TCCGTCGCCA CATCCCTCTC
3551 CCGCCCCTCA GTTCCCTGAG TGTGGCTTCT ACGGCCTTTA CGACAAGATC
3601 CTGCTTTTCA AACATGACCC CACGTCGGCC AACCTCCTGC AGCTGGTGCG
3651 CTCGTCCGGA GACATCCAGG AGGGCGACCT GGTGGAGGTG GTGCTGTCGG
3701 GTGAGAGGTG GTGGCCGGCC TGGGGCGGG GCCTCGGGTG GGGGCGGGGC
3751 ATCTGGGGGA GGAGAGGGTA GGGGGAGTTA GAAGTCAGGA GAGGCCGGGT
3801 GTAGTGGCTC ACGCCTGTGA TCCCAGCACT TTGGGAGGCT GAGCTGGAGC
3851 TGGGGGGATC GCTTGAGCCC AGGAGTTCGA GATCAGCCTG GGCAACATAG
3901 TGAGATTCCA TCTCTACCCC TTTCTCTCCC TCTGAAAAAA AAAAATAAGG
3951 AGAGTTGGGG GCTTCTGGAA GATGGTTACA GAGTGGGGTC ATGAAGGCGC
4001 TCTTTAGGGA CTGGTCTAAA CTTTCATTTA TGGATTAGGA TGCTAGTGAC
4051 ACGCTTTGTA CAGTTTGAAA ATTCATTGAG CTGTGCACTT GTGATGTGCG
4101 GCCTTTCCTG AACATATGTT ATACTTATTT ATTTATAAAA CTAGTCAAGT
4151 GCAGTAGTTA GAAGGGGGAA AAGAGGAGAA GAAGGAGTTG GATCTGTAAC
4201 TGACTGTGTT ATGCTTAAAT ATAAAGGTAA AAAATGGGCC AGCTGCAGTG
4251 GCTCACACCT GTAATCCCAG CAGTTTGGGA GGCTGAGGTG GAGGATCGC
4301 TGGAGCCCAG GAGTTTGAGA CCAGCCTGGG CAACATAAGG AGACCCCATC
4351 TCTTAAAAAA AAAAAAAAAA AAAAAGTTA ACCGGGCGAG GTGGCACACG
4401 TCTGTAGTCT CAGCTACTTG GGAGGCTGAG GTGGAGGAT TTCTTGAGCT
4451 TAGGAGTTTG AGGCTGCAGT GAGCCACGAT CATGTCACTG CACTCCAGCC
4501 TGGGCAACAG AGAGAGACCC TATCTCTAAA AAAGAAAAAA AGTAGAAAAA
4551 GAAAAAAAAA AGTTATGATG TCCATGGCTC CTGCCACGAA AATGCTAAAT
```

FIGURE 3B

```
4601 TAAATCAGAA TCTCTGCAAA GTGAGATGGA ATCTGCACAT CAGTATTTTT
4651 AAAAGCCCCC AGGTGATTTT CTAAGACACA GCCAGAAGCC AGTTCATCCA
4701 CTCACTATTC CAGTAGTATA GATGGGCATG CTCTCAGCAC CTTAGAGCAG
4751 TCTATGGCCC TTGGTCCCTC TTGAGGGTGG GGGCAGCTGC CTTTTTCATG
4801 GCTGTCTTCC CTGCTGCTCC GGCATACTGC AGTGCCCAGT GAAACCGGCT
4851 CAATGAATGA ATGACAGAAG TCTGGATTTA CACCTTTAGT GACCTTGTTC
4901 AGGCTTTAAG TACTCTTTCA TATCATAAGC TGGCCTCACT TGAATTTTTA
4951 TCTTCATTGT TGTCTCTCCC CTAAACCTGA GTTTTGTTTT GTTTTTGTCA
5001 TTTTTATTAT TTTTTGTTTT TTTAGACGGA GTCTCGCTCT GTCACCCAGG
5051 CTGGAGTGCA GTGGCGCAAA CTCAGCTTGC TGCAACCTCT GCCTCCTGGG
5101 TTCAAGCGAT TCTCCTGCCT CAGCCTCCCG AGTAGCTGGG ATTACAGGCG
5151 CCTGCTACCA CACGTGGCTA ATTTTTGTAT TTTTAGTAGA GACGGGATTT
5201 CACCTTGTTG GCCAGGCTGG TCTCGAACTG CTGATCTTAA GTGATCTGCC
5251 CACCTCAGCC TCCCAAAGTG CTGCGATTAC AGGTGTGAGC CACCGCTCCC
5301 GGCCCTGTTA TTTTGTTTTG AGGCAGGGTC TTGTTCTGTC ACCCAGGCTG
5351 GAATGCAGTG GCATGACCAC CACTCACTGC AGCCTCTACC TCCCAGACTG
5401 AAGCAATCAT CCCGCCTCAG CCTCCTGAGG TGGCTGGACT ATAGGCATTA
5451 CAGGCATGCA CCACCACACT GGGCTTTTTT TTTTTTTCTT TTTTTTAGAC
5501 AGAATCTTAC TCTGTCACCC AGGCTGGAGT GCCGTGGCAT GATCTTGGCT
5551 CACGGCAACC TCTGCCTCCC GGGTTCAAGC AATTCTCCTG CCTCAGCCTC
5601 CTGAGTAGCT GGGATTACAG GCACGCGGCA CCAGGCCTGG CTAATTTTTG
5651 TATTTTTAGT AGAGACGGGG TTTCATCATG TTGGCCAGGC TGGTTTCGAA
5701 CTTCTGACCT CAAGTGATCC GCCCACCTGG GCCTCCCAAA GTGCTGGGAT
5751 TACAGATGTG AGCCACCGGG CACCGCCTAT CCATGTTCTT TTTTGTTGTT
5801 GGTGGTGGTA TTTTTAATTA AAAATTTTTT AATTTGGTAA AATATACATA
5851 ACATAAAAAT TACTATTTTA GGCCGGGTGC AGTGGCTCAC GCCTGTAATC
5901 CCAACACTTT GAGAGACCGA GGCGGGCAGA TCACCTGAGT CGGGAGTTTG
5951 AGACCATCCC TGGCCAACAT GGTGAAACTC CGTCTCTACT AAAAATACAA
6001 AAATTAGTCG GGTGTGGTGG CGCATGCCTG TAATCCCAGC TACTCTGGAG
6051 GCTGAGGCAG GAGAACTGCT TGAACCCGGG AGGCGGACTT GTGGTGAGCC
6101 GAGATCTCAC TACTGTACTC CAGCCTGGGT GACAGAGTGA AACTCTCTAA
6151 CAAACACAAA CAAAAAAGCC CACAACATTT TAAGCACTTT TAAGCGTACA
6201 GTTCAGTAAT TTAAAGTTCA CGCACACTGT TGTGCAGCCG GTCTCCAGAA
6251 CTGTTGTCAT CTTGCGAAAC TGAAGCTCCT TGCCCGTTAA ACAACTCCCC
6301 AATTCCCGCT CTGTCCCTGC CCAGGGCGTA GGGATATATG TGTTTTGTTC
6351 AGGGGTGGAG CTGGGATTTG AACCCAGGCA GAATGTAGTA TGAGAGCAAA
6401 TGAAGGAAGG AAGGAAAGAT CACACCTTGC GGCTGGGAGC ACTGTGAGAA
6451 ATCAGGGAAC GTGGGGTCTG GAAAAGCTTT GGCCTACCCC GCCTCAAGCA
6501 TCCACCCCTA TTTTCCGCCT ACAGCCTCGG CCACCTTCGA GGACTTCCAG
6551 ATCCGCCCGC ACGCCCTCAC GGTGCACTCC TATCGGGCGC CTGCCTTCTG
6601 TGATCACTGC GGGAGATGC TCTTCGGCCT AGTGCGCCAG GGCCTCAAGT
6651 GCGATGGTGA GAGCTAAAGG GTTGGGGGCG GGGCCTGGGG CGGGGCTCTG
6701 CACCGGGGGC GGAGCGTAAT GGTCCTGGCA CGGGGACAGC GTGGGGAGGA
6751 GGAGCGGGTC TCAGAGCTGG GGGCGCAGCC TAGGAAGTAA TAATGGGAAG
6801 AAGGATGGGC CCAGAAGCAG AGCTTGGGGA AGGAGTGGTG GGGCTGGGCC
6851 GGGGCTCAGG TCTAGGGGCG GAGCCTAGGA GGTGGAGCTG GGAGGGACAA
```

FIGURE 3C

```
6901 GTAGGGGCTT AAGAACAGAG CCTAGGGGAG CAGAAGGGTG GCGGGGGAAG
6951 AGGGTGGGGC CTCTATCAGT TAGGGATCAA GCAGAGAAAC ATCCAGGAGG
7001 AGATATATAT TGAGATATTT ATATGCAAGG AATCAGCTTA CAGAATTGTG
7051 TGGGCTGGCT AGGCAACTCA AATCTGGCTG GCACAGTGG GGAGGCCAG
7101 TAATCCCAGC ACTTTGGGAG GCAAAGGTAG GTGGATCACT TGAGGCCAGG
7151 AGTTCAAGAC CAGCCTGGGC AACATAGCAA GACTCTGCCT GTACAAAAAA
7201 TAATTAGCCA AGCATGGTGA CAGACACTTG TGGTCCCAGC CACTTGGGAG
7251 GCTGAGGCGG GAGGATCACT TGAGCCTGGG AGCTCGACAC TGTAGTGAGC
7301 CCTGATTGCA CCACTGCACA CCAGCCTGGG TGACAGAGCG AGACCCTGGC
7351 TCAAAAACAG GAAAAAGGCC GGACACGGTG GCTCATGCCT GTAATCCCAG
7401 CACTTTGGGA GGCCGAGGCG GGTGGATCAC GAGGTCAGGA GATTGAGACC
7451 CTCCCTGGCT AACATGGTGA AACCCCGTCT CTACTAAAAA TACAAAAAAT
7501 TAGCCGGACG TGGTGGCACA CGCCTGTAGT CCCAGCTACT TGGGAGGCTG
7551 AGGCAGGAGA ATTGCTTGGA CCTGAGAGGA GGAGGTTGCA GTGAGCCGAG
7601 ATTGTGCCAC TGCACTCCAG CCTGGTGATA GAGTGAGACT CCTTCTGAAA
7651 ACAGAAACAA AAACAAAACA ATAAAAAGAA AAAGAAAAAA AAATCCATCC
7701 TATCAGGAAG GGCAAGTGGG AACTCAGGCA CAAGCTGAAG CTGATGTCCA
7751 CAGGTGGAAT TTCTTCATCC GAAAAGTCTC TGATCTGCTT TTTAAAACAT
7801 TCAGCTGATT GAATGAGACC CACCTAGAAC AAGCAGGATC ACCTCTCCCA
7851 CTTACAGTCA GCTGATTATG GATTTTCATC ACATCCAGAA AATACCTCCA
7901 CTGGGCCGGG TGCGGTGGCT CACGCCTGTA ATCCCAGCAC TCTGGGAGGC
7951 CGAGGCAGGT GAATCACCTG AGGTCAGGAG TTCGAGACCA GCCTGTCCAA
8001 CATGGTGAAA CCCCGTCTCT ACTAAAAATA CAAAAAAGCC GGCGTGTTGG
8051 TGGACGCCTG TAATTCCAGC TACTCGGGAG GCTCAGTCAG GAGAATCTCT
8101 TGAACCCGGG AGGCAGAGCT TGCAGTGAGC TGAGATTGCA CCATTACACT
8151 CCAGCCTGGG CAACAAGAGC AAAACTCTGT CTCAAAAAAA TGAAAAGAAA
8201 AGAAAATACC TCCATGGGGC CTTCTCTCCC CAGTTCTTCC TGGAGTCGGG
8251 GAAAAGCTGG GTTGAGAAGG TGAAAAGAAA AAACAAACCT TGACTGGGCA
8301 CAGTGGTTCA CACCTGTAAC CCCAGCACTT TGGAGGCTGA GGCAGGCGGA
8351 TCATGAGGTC AAGAGATTGA GACCACCCTG GCCAACATGG TGAAACCCCA
8401 TCTCTCCTAA AAATACAAAA ATTAGCGGGC GTGGTGGCAT GTGCCTATAG
8451 TCCCAGCTAC TTGGGAGGCT GAGGTAGGAG AATCACTTGA ACCCAGGAGA
8501 CAGAGGTTGC AGTGAGCCGA GATCGTGCCA CTGCACTCCA GCCTGGCAAC
8551 AGAGCGAGAC TCCGTCTCAA AAAAAAAAAA ACAAAAAAAA AAAACACAAA
8601 CAAACCAACC TTCATGGCAA CATCTAGATT AGTGTCTGAA TAACTGTGGA
8651 TCTCGCCTAG CCAAGCTGAC ACATTAACAT GACTATCAGG GTCCATCTCT
8701 TGTCAACCTG GCACCTGTCT TAGTTTGTCA GGGCTGCCTT AACAAAATAC
8751 CACCCTGCGT GGCTTAAATG ACAGACATTT ACTTCTCAAA ATCCCTGGAA
8801 TTGTGAGAGG CTGGAAAGAC AAAGATCCAG ATTCTGGCAG GGTTCTGTTT
8851 CTGGTGTAGC CTGCTTTCCT GCCTTGCAGA GGGCCATCAT TTCACTGTGC
8901 GCTCACATGG GACACGGAGA GAGAGATCCC TGGTATCTCT TCCCTTTATA
8951 AGGAAGGCCA GGCATGGTGG CTCATGCCTA TAATCCCAGC ACTTTGGGAG
9001 GATGGTGGAT CGCTTGAGTC CAGGAGTTCG AGACCAGCAT GGGCGACATG
9051 GTGAAACCCC GTCTCTAAAA AATACAACAA ATTGGCCAGG CATGGTGGTG
9101 CATACCTCTA GTCCTAGCTA CTCAAGAGGC TGAGGTGGGA GGATCACCTG
9151 GGCCTGGGAG GTTGAGGCTG CGGTGAGCCG TGATCATGCC ACTGCACTCC
```

FIGURE 3D

```
9201  AGCCTAGGTG ACAGAACACG ATTGTCTCAG GAAAAAAAAA AAAAAAAAA
9251  AAAAAAGGGT CACCAGTCCC ATTGGATTAC AGCCACACTC TTTCGGCCTC
9301  AATTAACCTT AATTACCTCC ATAAAGGCAC CGTCTCCAGA TATAGTTGCA
9351  TTGGAGGTTA GGGTTTCAAC ATAAGAATTT TGGGGGAGAC ACAGACATTT
9401  AGTCCATAAC AGCACCCATA CATATCTCCT TAAATCATAG TTTAAAAATA
9451  TACAGGTTTT CTTTTTTGGA GACAGCGTCT CAGTCTGTCA CCCAGGCTGG
9501  AGTGCAGTGG CGCGATCTCA GCTCACCACA ACCTCCACTT CCCAGGCTCA
9551  AGCGATTCTC CTGCCTCAGC CTACCGAGTA GCTGGGATTA CAGGCACACA
9601  CCATTACTGC CCGGCTAATT TTTGTATTTC TAGTAGAGAC GGGGTTTCAC
9651  CACGTTGGCC AGGCTGGTCT TGAACTCCTG ACCTCAAATG ATCCACCCGC
9701  CTTGCCCTCC CACAGTGCTG GGATTACAGG CATGAGCCAC CGCGCCTGTC
9751  CAAAACATAC AGTTCTTTAA GCCAAGATGT CTCAAGGTTC AGCCCAAGTG
9801  TCAAGATCTA TATAGGTCCT CTGTCCCTGT TATTCATGCT TCTGAGTGAG
9851  AATGTTGAAA TCGGGGCTCT GCCTACAGAT GAAGGCCATG TACCTGCATT
9901  GGCTATGAGG ACAGATGACA GGTGAGGACC ATCCATTCTG TGATGAGACC
9951  CTGTGGCTCC ATTTTTTTGT GTGTGTGAGA CAGAGTCTTG CTCCGTCACC
10001 CAGGATGGAG TGCAGTGGCG TGGTCTTGGC TCACTGCAAC CTCTACCTCC
10051 TGGGTTCAAG CAATTCTCCT GCTTCAGCCT CCCAAATAGC TGGGATTACA
10101 GGTGCGCACC ACCACTCCTG GCTAATTTTT GTATTTTTAG TAGACGGGGT
10151 TTCACCATGT TGGCCAGGCT GGTTTCAAGT AATCCACCCT CCTCAGCCTC
10201 CCCAAGTGCT GGGATTACAG ACATGAGCCA CTGCGCTGGG CCCCATGCGC
10251 CTCCATTTTT GTATGGTGTG CCCTGCAATT AGAGCCATAT TCTTGGATGT
10301 TCCATTGGGT ATTAGGTCTG AGACAGCATC TCTAGCTCCG TGGGTGCCAC
10351 GCTTGTACAG AAATCCTGAT TCTGGGCCAG GCACGGTGGC TCACACCTGT
10401 AATCCCAGCA CTTTGGGAGG CCAAGGCGGG CGGATCATGA GGTCAGGAGT
10451 TAGAGACCAG CCTGGCCAAC ATGGTGAAAC CCTGTCTCTA CTAAAACTAG
10501 AAAAATTAGC TGGGTGTGGT GGCGGGTACC TATAATCCCA GCTACTCGGG
10551 AGGCTGAGGC AGGAGAATCA TTTGAACCTG AGGGGGTGGA GGTTGCAGTG
10601 AGCCGAGATC ATACCATTGC ACTCCAGCCT GGGTGACAGG GTGAGACTCC
10651 GTCTCAAAAA AAAAAAAAA AAAGAAATCC AGTTTCTCCA ATATCCTGTG
10701 TTCCAGATCA TCATGCAGTC CAAAGTATAC TTGTATTATT TAAGGACTCT
10751 AGGCCTGCAG ATACTGATTC AGTGCATTAA AAGCTCTTAT AAATATTGCC
10801 ATCGTCCACA CACCATATCC AACTCTTGAG GTCTCAGCAT ATGCAGTCTT
10851 TGTCATGATA CAGCCCTGGT GTCATCAAGT CCTAATGGGT TATCAGCACA
10901 GACTTCACTG GTGCAGCATC ACAGATGATG GTCCCAGTTC CTATGGTGGC
10951 AAGAGAACCC CAAATGACTA CATTCCGACA GGAGTTTAAC TCTATCCTGA
11001 GACTCATTCT GAGAGTTATA GATAAGATTC TGAAATTCTG GAAGGCACAT
11051 GAGTGATTCA AGGCCAACAC TGGGAAATGG TTCCTGTGTG CAAAGACCAT
11101 TTGCCCTGCT GAAGCTCTTC TTGCAGGGCC AACACCGTTC TCCAAGCTTG
11151 CCTCCGTGAT TACAGCATGC AGCCAAGACA GTGCCTACAA TGAGGAGGTG
11201 TGGAACTGGA AAGCCTGGAG CAGGCGGGTA CCAGAAGGGC TCCCAAAGGC
11251 TGGAGGAACA TTCTTCACTC CAGAATAGAA AGCGATCCTG GAATCGTTTG
11301 GAATCACTGG AGATGTATTA GAGCACACAT ACAGAACGTC CAGTGGGAAA
11351 CAGGGAGTTG AGCTGATTTC TCCATGGATG AGGATTTTAA AAGATAAAAT
11401 AGGCAGGGCA CAGTGGCTCA TGCCTGTAAT CCCAACACTT TGGGAGGCTG
11451 AGGTGGGAGG ATCACTTGAG CCCAGGAGTT CAAGACCAGC CTGGGCAATG
```

FIGURE 3E

```
11501 TAGCGAGACC CCATCTCTAC AAAAAAATAA AAATAAAAAA ATTATCTGGG
11551 CATGGTAGTG TATGTCTGTG GTTCTGGCTA CTCAGGAGGC TGAGGCAGGA
11601 GGATTACTTG AGCCCAGGAG TTGAAGGCTG CAGTGAGCTA TGATTGTGCC
11651 ATTGTGCTTC AGCCGGGGGT ACAGGGAGAT CCTGTCTCTA CAAAATAAAA
11701 TAAGACAATA AGAAGTCATA CTTCTGCCTA GTATGGTACA ATGGACCTGA
11751 GTACAACTGA GAACTCTTTT TTTTTTTTTG AAACTGAGTC TCGCTGTATT
11801 GCCCAGGCTG GAGTGCAGTG GCGTGATCTC AGCTCACTAC AACCTCTGCC
11851 TCCTGGGTTC AAGTGATTCT CCTGCCTCAG CCTCCGGAGT AGCTGGGATT
11901 ACAGGCGTGT GCCACTACAC CCGGCTAATT TTGTATTTTT AGTAGAGATG
11951 GGGTTTTGCC ATGTTGGCCA GTGTGGTCTC AAACTCCTGA CCTCAAGTGA
12001 TCCGCCGGCC TTGGCCTCCC AAAGTGCTGG GATTACAGGC GTGAGCCACC
12051 ATGCGTGGCC CACACTACTA AGATTTAATC ACACTACTTA GGGATTGCCT
12101 GGATTCCAGG TCTACAGAAA AGAGAAAGTG GGGTACAGGG GGTGAGCAGA
12151 CCTGGAGGGA TAGTGACCTT AGGGGTGGGG GTGAGGAGAG GCATTTTCTT
12201 TTGGAAAGTT GGGGTTGGGG AAAGAGGGGG AACCAAAGGG GCCTCAGAAA
12251 AAGGAAGGTC AGGGTTAGAA GGGGGAACAG GTGTCTCTAG GGAGATGGAC
12301 AGGAGTTTTG GGGAGGACTA GAAGGAGGTG CTTACCATAG AGGACTGGGG
12351 CTGGGTCAGA GCTTTGGCGG GGACTTTTGA GGCATCCATT GTTGCAGTGG
12401 GAAAAGGTGG GGTGTGAGGC GCGTTCAGGG CCTGGGGGGC AGATGGGGTG
12451 ATGTCGGGGC TACAAGCTGG AACTAGGGGT GGAGCTTTGG AGGGAACCTT
12501 TGAGGTATCC CTTGTTGGAG TGGGAAAATT TTGGGTGTGA GGCGTGTTCA
12551 GGGTCTGGGG GACAGATGGG GTGATGGCAG GGCTACAAGC TGAAACTGGG
12601 GACAGAGCTT TGGGGGGAGC CTTTGAGGTG ACCCTTGTTG GAGTGAGAAA
12651 AGGGGTGTGG GTGTGTTCAG GGTCTGGGGG ACAGATGGGG TGATGGTGGG
12701 GCTACAAGCT GGAACTTGGG GCAGAACTCT AAGGAGGGGT GGGCCTGAAG
12751 GGGCTGATAC ACTTACGGAT AGTAGTGCCT TTTGGAGGAG ATCGTGCTGG
12801 CGGGGGGTGA TGGGACAGGA CCAGGTGAGA GATTGGGTGG AAAGGGCACA
12851 ACTTCTCAAG AAGAGACCTA GGAGGGGCAG ACGCCATGTC TCTTACTCTC
12901 TGGCGCCCCC TGCAGGCTGC GGGCTGAACT ACCACAAGCG CTGTGCCTTC
12951 AGCATCCCCA ACAACTGTAG TGGGCCCGC AAACGGCGCC TGTCATCCAC
13001 GTCTCTGGCC AGTGGCCACT CGGTGCGCCT CGGCACCTCC GAGTCCCTGC
13051 CCTGCACGGC TGAAGAGCTG GTGAGGAGAT GGGGGATGGG ACGGGTTGGT
13101 GGCTAGGGGG GTGACTTGGC CCAGGCATGG GGCCAACGCA CTGATGTGTC
13151 CCCTCCATTC TTGCCAATGA CAGAGCCGTA GCACCACCGA ACTCCTGCCT
13201 CGCCGTCCCC CGTCATCCTC TTCCTCCTCT TCTGCCTCAT CGTATACGGG
13251 CCGCCCCATT GAGCTGGACA AGATGCTGCT CTCCAAGGTC AAGGTGCCGC
13301 ACACCTTCCT CATCCACAGC TATACACGGC CCACCGTTTG CCAGGCTTGC
13351 AAGAAACTCC TCAAGGGCCT CTTCCGGCAG GGCCTGCAAT GCAAAGGTTA
13401 GCTGGGCCTG TCGGGGAGGA CAGTACAGGG TCAGAACCTC CTTCCCGCCC
13451 CAACCTGGTC TTGTGGCAGG ACACAAGGAT CTGAGCCTTG GGACCCCAGG
13501 GCCTCAGAAG GGGAGGGCCC TGAATCCTAG TGTTCTGGGA CCTTTGGAAT
13551 TCTGGAATCT TAGAACCTCA GTTGTGTGT TGTGTGTGTG TGTGTGTGTG
13601 TGTGTGTTGT GTTGTTTTTT GAAGACAGGG TGTCACTCTA TCACCCAGGC
13651 TGGAGTGCAG TGGCGCAATC ACGGCTCACT GCAGCTTCAA CCTCTTGGGT
13701 TCAAGTGATC CTCCTGCCTC AGCCTCCCAA GTAGCTAGGA CTACAGGTGG
13751 TGCCACCACA CCCAGCTAAT TTTCTTTTCT TTTTTTTTTT TTTGAGACGG
```

FIGURE 3F

```
13801 AGTCTCACTC TGTCGCCCAG GCTGGAGTGC AGTGGTGTGA TCTCGGGCTC
13851 ACTGCAAACT CTGCCTCCTG GGATCAGGAC ATTCTCCTGC CTCAGCCTCC
13901 TGAGTAGCTG GGACTACAGG CGCCCGCCAC CATGCCTGGC TAATTTTTTT
13951 GTATTTTTAG TAGAGACGGG GTTTCACCAT GTTAGCTAGG ATGGTCTCGA
14001 TCTCCTGACC TTGTGATCCA CCTGCCTCGA CCTCCCAAAA TGCCGGGATT
14051 ACAGGCGTGA GCCACCGCGC CTGGCCACAC CCAGCTAATT TTTAAATCAT
14101 TTGTAGAGAG AAGGTATCAC TATATTGTTC AGGCTGGTCT TGAACTCCTG
14151 GGCTCAAGCA ATCCTCCTAC CTCGGCCTCC CAAAGTGCTG GGATTACAGG
14201 TGTGAGCCAC CGCGCCCAGC TGAACCTCAG TCTTTAGAAC CTTGGAATCC
14251 TAGATTCATA ACGTGCTTAG CATGAATTC TAAAACTGTA GAACCTGAGA
14301 ATTCTAGAAT CAGAACCATA GCATTCAAGA ATTCCGAATG ATAGAATTCA
14351 GCTAAAATAA CAACAGAACT TTAGATTACA CATCTTAGAT CTCCCAAGTT
14401 ATAGACTCTC AGAGCATGAG AATTTTGGAA CCATGGGATT TGAGGGTAAT
14451 AGAAACATAG GCACATCAAA TTTGAGAGTC TTAGACGTCT AGAATCATAT
14501 AAGCTTGAAA CCATCGTAAC CTAGAATCCT GGAAATTCTA GACTCCCAGA
14551 ACTTTGAACA ATCAAATTCT AGAATCCAGC CAGGTGTGGT GGCTCATGCA
14601 TGTAATCTCA GCACTTTGGG AGGCCAAGGT AGGTGGATCA CTTGAGCCTA
14651 GGAGTTTAAG ACCAGCCTGG GCAACATGGT GAAACCCTGT CTCTACAAAA
14701 AAAATTAAAA ATTAGCCAGG CATGGCAGCA TGCATCTGTG GTTCCAGCTA
14751 CTTGGGACTC TGAGGAGGGA GGATTGCTTG AGCCCAGGAG GTTGAGGCTG
14801 CAGTGAGCCA TGATTGTGCC ACTGCATTCC AGCCTGGGTG ACAGAGCAAG
14851 AACTTGTCTC AAAAAAAGAA AAAAAAAAT TCTAGAACCT CAGAAGCCTA
14901 GATCCACATA AACTTAGAAA CATCCAATTC AAGAATTTAC TGGAACAATC
14951 AAATTCTAGA ATCTTAGAAG CCTAGAGCTA AAGAAGCATA GAAACATCAA
15001 ATTCTAGAAT CTTGTATGTA TAGAATCCTA GAACCTTGGA ATCTGCAGAT
15051 TCTGGAGGTA GAGAAGCCTA GAATTGTAGA ACCCTAGAAC TGTCAAATTT
15101 TAGAGTTTAG ATATATAACA CCCTAAAATC TTGGACATTA AAGAGTCTTA
15151 GAAGTGTTGA CTCATAGATG TCTAGAGTTC TAGAAACTTG GACATCAAAC
15201 TCTGAAGCCT TAGAAATACG GAATCAGGTC AGGGGCAGTA GCTCACACCT
15251 GTAATCCCAG CACTTTGGGA GGCTTAGGTG GGTGGATTGC TTGAGCCCAG
15301 GAGTTCAAGA CCAGCTTGTA CAACATGGAA AGACCCCATC TCTACAAAAA
15351 ATACGAAAAA TTAGCCAGGC ATGGTAGTGC GTGCCTGTAG TTTCAGCTAC
15401 TCAGGAGGCT GAGGTGGGAA GATCGCTTGA GCCTGGGAGG CAGAGGTTGC
15451 AGTGAGCCGA GATGGTGCCA TTGCACACTC TAGTCTGGGT GACAGCCAGA
15501 CTGTTTCTTA AAAAAAAAAA AAAAAAAAAA AAACCAGAAT CATAGAACCT
15551 TCATAAAATA GGTTTTTAGT AAACTCTAGA ATCTTCGATG TATAGTGTCC
15601 CTAGAACCGT GGAAACACTG AACTCTACAG CAATGGTTCT CGACCAGGGG
15651 CCGTTTTGCT CCTAGGGGAT GTTTGGCAAG GGTTGGAGAT GGTTTTGTTT
15701 GGTACGCTGG GATAGTGCTA CTGGCATCCA GTAGGTAGAA GTCAGAGATG
15751 CAGCTAAACA TCCTACAATA CACAGAGCAA GTGCCCTAAA ACAAGGAATT
15801 ATCCTGGGCA CTGTGTTAGT GTCACGGGTT GAGGAACCCA GCCCTAGGGT
15851 GTTCAGAGTC TGGAGTCACA GCACATTAGA ACCAATAACA CACACACACA
15901 CACACACACA CAAGTCGGGC GCGGTGGCTC ACGCCTGTAA TCCCAGCACT
15951 TTTAGGAGGC CAAGGCAGGT GGATCATCTG AGGTCAGGAG CGCGAAACCA
16001 GCCTGACCAA CATGGCGAAA CCCCGTCTCT ACTAAAAACA CAAAAAAATC
16051 AGCTGGGCGT GGTAGTGGGC GCCTGTAGTC CCACGCCCAG CTAATTTTTG
```

FIGURE 3G

```
16101  TATTTTTAGT AGAGACGAGG TTTTACCATG TAGGGCAGGC TGGTTTCGAA
16151  CTCCTGACCT CAAATGATCT GCTCTCCCCG GCCTCCCAAA ATACCGAGAT
16201  TACAGGCGGG AGCCACTGCA CCCAGCAGTC GTCGGGATTT TGAGTCTAGC
16251  CCTCCTACTT AATCAAGACC CCCCCGATGG TTGGGAAAAC TGTGGCTGAA
16301  AGTGGGAAAA TGACCAGGGC AGCAGCAGCC AGTGTTCTTA CCCAGACAGC
16351  AAGAGTAGAC TCTTTTGAGC CTGAGGCTTA GGGTCAAGGT TCAAGCCTTC
16401  CAGGTAACCT CTCTTCCCCT TCTCACCCGT TCCCTTGTTC CCTGTCCTAC
16451  CAGACTGCAA GTTTAACTGT CACAAACGCT GCGCCACCCG CGTCCCTAAT
16501  GACTGCCTGG GGGAGGCCCT TATCAATGGA GGTGAGAGGC TGGGGGGATG
16551  CTGGGGAGAA AGGGGAAGGG GCAGGACTGG GTGGAGACCC CTCTGATGCC
16601  TCCGTCCCCA CAGATGTGCC GATGGAGGAG GCCACCGATT TCAGCGAGGC
16651  TGACAAGAGC GCCCTCATGG ATGAGTCAGA GGACTCCGGT GTCATCCCTG
16701  GCTCCCACTC AGAGAATGCG CTCCACGCCA GTGAGGAGGA GGAAGGCGAG
16751  GGAGGCAAGG CCCAGAGGTA TACACAGAAC CCTCCAAGAG ACCCTGGGGG
16801  AAGACCCTCC TGCACAGTGA ACCTCAATTT CTTTTTCTCT ACAATGGGCT
16851  GACATCACCT CATATTTATA AATTTTCCCA GTTCCTGAGG CAAACCTTTT
16901  AAAGCACTAC AATTTTTTTT AAATAATTTT TTGTTTGAGA CAGGGTCTCG
16951  GTCTGTCGCC CAGGCTGGTG CAGTGGTGCA GTCTTGACTC ACTGCAGCCT
17001  CGACCACCTG GGCTCAAGCG ATCCTGCCAC CTTAGCCTCT CGAGTAGCTG
17051  GGACCACAGG CTCGTCCACC ACACCCAGCT AATTTTTGTA TTTCTGTAGA
17101  GACAGGGTCT ACCCTATGTT GCCCAGGCTG GTCTTGAACT CCTGACTCCT
17151  GAGCTCAAGT GATCCACCCG CCTCAGCCTC CCAAAGGGTC TTGCTTTGTT
17201  GCCCACTGGA GTGCAGTGGT GTGATTGTGG CTCACTGTAA CCTCAAACTC
17251  CTGGGCTCAG GTGATCCTCC TGCCTCAGCC TCCCGAGTAT CTGGGACTAC
17301  AGGGATGCAC TGCTATCCCT GGCTAATTTT AGACGGCGTT TCGCTCTTGT
17351  TGCCCAGGCT GGAGTGCAGT GATGCAATTT CAGTTCATTG CAACCTCTGT
17401  CTCCTGGGTT CAAGCGATTC TCCTGCCTCA GCCTCCCAAG TAGCTGGGAC
17451  TACAGGCACC CGCCCAGGCC CAGCTACTTT TTTTGTATTT TTAGTAGAGA
17501  CAGGGTTTTG CCATGTTGGT CAGGCTGGTC TTGAACTCCC AACCTCAGGT
17551  AATCCACCTG CCTCGGCCTC CCAAAGTGCT GGGATTACAG GCATGAGCCA
17601  CCGCGCCTGA CCTATATTCC TCTTCTTTTT TTTTTTTTTT TTTTTTTAAG
17651  ATAGGGGGTC TTGCTATGTT GCCCAGGGTG GTCTTGAACT TCTGCGCTCA
17701  AGCAATCCTC CCACCTCAGC CTCCCAAAGT TCTGGGATTA CAGGTGTGTG
17751  CCACTGTGCC CCCAGCCTAC ACATTTTTAA ACTATACACG GAGTTCATAC
17801  TTAGTCAGCT CCACTGGAAT GTGAGCTCAG GTGCATGAGG GCAAGGATAT
17851  TTTCTGCCCT CCCAGGTGCC TAGGACAGGA CTGGCTCAGA TCAGGCACTT
17901  CCTATCTGGG TGTGGCGTGA ATGTTTATTG AGAAAGCACA GTTCACACAG
17951  GCGCTGGAGG GTGACAGCCC AGATCCCAGC TCTACCACTT CACTTGCTAG
18001  GCGCTTCCCT GTGTGCCACG GTTTCCTCCT GGGGCGATGA GGTACCTACC
18051  CCACGGGGTG ATAAACCTGG GGTAGGGGTA AGGGGCACC  CTCACAGGTG
18101  CACTGGAAAA TATTTAATGA GCACCTGCTG TGTTCAAGCA CACAGCTATG
18151  AACAAAAGAG GTAAAAGTCT GCCCTTCTGG AGCTGACTGC CTCAGTGGGG
18201  AGACAGCTAA TAAATGCATC CATAGCATCG GTATTGGTA  ATGGTGATAA
18251  AAACAAGAGG AGATGGAGAA TGGGGACAT  GCTATCTTAG GGTCCTTCAA
18301  GGAGACCTCG CTGAGGAAGT GGCAGTTGAA GGGAGGGGAG GGAAGGAGCC
18351  TTGTGGGGCT CTGGGGGAAA AGGCTTCCAG GCAGAGGCAA CAGCGAGTGC
```

FIGURE 3H

```
18401 AAAGGCCCTG GGGTGGAGGC ACCGTGTTCC AGGGACAGCA AAGAGACCCA
18451 TGTAGCTGCA GCAGGGAGGG CGAGGGGAAG AGGGTTGGAC AGAAAGGGGA
18501 TGGGTAAGCC AGTCACAGTG ACGACAGAGT GTTTCCTGCG GTGCCTCCCA
18551 ACCCAAGCAG CCTGAAGCCG CAGGTTCCCT TTCTCCCACG TCTTTCCTGG
18601 GAATGCCTAG TAACACCGTC ATACACTGTC AAGAGTTGGA CCTTGAGGGA
18651 TTGGGGGTGG CGGGTGTGGG GAGAGGCAGC CCATTTCACA GATGGGGAAA
18701 CTGAGTCTCA GGCAAAGAGA TGTGATCAAG GCCACCCAGG TTCTGATCTA
18751 GCACAGGGAT CCAGAGATTG TTGGTTCCAG AGTTGAGCAA GTCACTTAAT
18801 CTCTCAAATC TCAAACTCCT GACCTCAAGT GATCCCCCCA CTTCTGCCTC
18851 CCAAAGTGTT GGGATTACAG GCATGAGCCA CCATGCCCAG CAGGCCACTT
18901 AATCTCTGTA GACCTTCCTT ACTGTACTAA CAGCATCTGC ACAAATGAGG
18951 GAGGTGAGGC CAGAGAGGT TGAATCACTT ACCCAGTGTC ACACAGCTGG
19001 CTCCACAATT GCTGGACTAA ATACCAATTA GCACTTACTG GAGGTCCTCT
19051 GTATGCCAGG CACTGTACTA AGCTCCGTAG AAAGGTTTCC ATTCCTCATA
19101 GCATCCCCTT TGGGTGGACA AACTGAGGCA TGAAGAGGTT AGGTAATTTG
19151 CTAGGCAGCC TGACTTCAGA AAGGCCTACT ACAGAAGCCC TCTCAAGAAT
19201 CTCCTTCTGG GCCAGCGTGG TGGCTCACAC CTGTAAGCAC TCTGGGAGGC
19251 CGAGGCGGAT GGATCTCGTG AACGGATTCT AAGGGTGGGA CTAGGGGCAG
19301 GAGTTAGGGA AGGAGTTGAG GCAAAGAGTT CGAGACCAGC CTGGCCAACA
19351 TGGTGAAACC TCATCACTAC TAAAAATACA AAAATTAGCC AGGGGTGGTG
19401 GCGTGCACCT AATGGTCACC GTGATTGTCC CGGCCACTCA GGAGGCTGAG
19451 GCACGAGAAT CGCTTGAACC CGGGAGGCAG AGGTTGCAGT GAGCCGAGAT
19501 CGCACCACTG CATTCCAGCC TGGGTGACAG AGCGAGCCTC TTAAAAACAA
19551 ACAAAAAGCA ACTCCCGGGT GTGTGTTGGG GGGAAAATGT CAAAACAAAC
19601 CAAACAAACA AAAACAGTCC CCAACTCCCT AGTTTCCCAG AGATGCCCCC
19651 TGCATTCCCA AGCAGCATGG TCACTTTCTG CATGTGACTT CTCACCCCTT
19701 CCTCTTCCTT CGCAGCTCCC TGGGGTACAT CCCCCTAATG AGGGTGGTGC
19751 AATCGGTGCG ACACACGACG CGGAAATCCA GCACCACGCT GCGGGAGGGT
19801 TGGGTGGTTC ATTACAGCAA CAAGGACACG CTGGTGAGTG GCCGGGGCGG
19851 GGCCGGGTAC GGCGGAGCGA AGGCTGGAAG AGGGGCGGCT CAGCTTGAGT
19901 AGGCGGGGCT AGGTGGGTGG GGCTGGAGCT AGGCGCGAGC GGGGCCAGTA
19951 GTGGGCTGGG CCGTGCTGGA GGCGGGGCTA GAATTAGAAG TGTGGGCTGT
20001 AAGGGTGGGA CTACGGGCAG GAGTTAGGGA AGACCCGGGG CTCAGGGCAA
20051 GGTCAGGGGC GGGGCTAGAG TTAGGGGAGG AGCTTGGCTG GAGGAAGAGG
20101 GCTAAGTGGG GGCGAGTCTG GGGTTAGGGC GTGGGGGCTG GGCTAGGGTT
20151 AAGGCTAGGG GCGGGGCTGG GGTTAGGGCG TGTGGTGGGG TGGGGTTACG
20201 GCGTGGGGTA GGTGCTAGAG TTACGGCGTG CACGTGGTGC TCCAGGCACC
20251 TGGAGCCCCA AGCAGCTCCA CGGGATAGGG ACTGGGCAGG AAAGTCTGGC
20301 GGTTCACGTG ACTCTTCAAA CATCTCTGCA GAGAAAGCGG CACTATTGGC
20351 GCCTGGACTG CAAGTGTATC ACGCTCTTCC AGAACAACAC GACCAACAGA
20401 TACTATAAGG TAAGCCTCCG GGCTTTCAGC TCCCTCGGAC TTCCCGCTGT
20451 GCCCACAAAC TTTCCCACAC CTCCTCCTAC CCCCAGTTAC TCCAGACAGA
20501 TCCTGCAAAT CACACCCTCT GCCCACCCCC AGCCTCCCTG CTTCCAGCTC
20551 ATCAGCAAGT GCTGCCCATC CGATTCTGGC CCCACCACTT TCCAGCCAGG
20601 GGGACTCCGG GCAGGTTCCC TTACTTCTCA GTGCCTCACG CTTCTCACCT
20651 GCAAAATGCC TCAAATGCTA ATACTCACCT CAGGGCTGGT GCGAGAATTC
```

FIGURE 31

```
20701 AAAGAGCCAA TCCACTAAAC CAATTGGCTT AAGGCGTGGT ATATATTAAG
20751 CTCCCAGTAA TTCTAAGGCT GTTCTCACTA TTCCTTTATT TTTTGTTATT
20801 TATTTATTTT TTGAGACAGA GTCTCACTCT GTCGCCCAGC TGGAGTGCAG
20851 TGGCGCGATC TCGGCTCACT GCAACCTCCG CTTCCCGGGT TCAAGCGATT
20901 CTCCTGCCTC AGCCTCCCAC CCTAGGACTA CAGGTGAATG CCACCACACC
20951 CAGCTAATTT TTGTATTTTT AGTAGAGACG GGGTTTCACC ATGTTGGACA
21001 GGATGGTCTT GATCTCTTGA CCTCATGATC TGCCCCCCTC GGCCTCCCAA
21051 AGTGCTGGGA TTACAGGCAT GAGCCACCGC ACCCGGCCTC ACTATTTCTT
21101 TATAATTAAT GTATTGCATT GTGTGCGTAT TCGTCACCAC CTCCCATGCC
21151 CACACTGTGT CCCAGCCACT GTCTTCCACC TGGATGGTTT CAGCCTTCTC
21201 CTTGCAGGGT CCTTGCTTCT GACCTCACAA CCTCTGTCAT TTCCCCCACA
21251 GCCAGGGGGA GTCTTCATTA AAACCGTCAA ACCCCCCAGT GGCTCCCATT
21301 GTCTTAGAAG TAATAAAACC TGGTACTCCA GCTGTTACCT GCCCTGGAAG
21351 CGTCTTCCTT GAACTTTCCA TGGCTGGTTC CTTATCATCT TCCCATTTTG
21401 CTCAGACCAC ACCATCTAAA ATGCTGTCCT TGGCCAGGCG TGGTGGCTCA
21451 CGCCTGTAAT CCCAGCGCTT TCAGAGGCCG AGGTGGGCGG ATCACTTGAG
21501 ATCATGAGTT CGAAACCAGC CTGGCCAATA TGGTGAAACC TTGTCTGTAC
21551 TAAAAATACA AAAATTAGCT GGGCATGGTG GCGGGTGCCT ATAACCCCAG
21601 CTACTTGGGA GGCTGAGGCA GGAGAATTGC TTGAACCTGG GAGGTGGAGG
21651 TTGCAGTGAG CTGAGATCGC GTCACTGCAC TCCTGCCTGG GCAACAGAGC
21701 AAGACTCCAT CTCAAAAAAA TAAAATAAAA TAAAATATAA TGCTGTCCTC
21751 ACCATGCCCC CCCGACGTGT CCATGTCATC ACCTGGTTTT ATGGGCTGCC
21801 TAAGTCATTC ATTCTTTCCT CTCTCCTACC TCCCTCCTTC CTCTTTTGAC
21851 ACGTTTCCCA CCCCATAGTC CCTGTGCCTT CTGTCCCGCC TGGGTCCCCT
21901 CAGCCTCCTT CCTGGTTCTC TGTCTCCATC TCATTCTATT CCATCTGCCC
21951 TCCGCACACA AGCGGATGAT GCTCAAAAGC CTTCAGTGGC TTCCTAGGGC
22001 CCTTGGACAA AGCCCAGGCT CTTCCTTGTG GCCCGCAAAG CCCTGTGTGG
22051 CCTCATTTCC TCCATTTATT ATCAAACGTT TATTTTTGAG ACGGAGTCTC
22101 GCTCTGTCAC CCAGGCTGGA GTGCAGTGGC GCGATCTTGG CTCACTGCAA
22151 CCTCCGCCTC CGGGGTTCAA GTGATTCTTC TGCCTCAGCC TCCCAAGTAG
22201 CTAGGATTAT AGGTGTGCCA CCACGCCTGG CTAATTTTTG TATTTTTAGT
22251 AGAGATGGGC TTTCACCATG TTGGTCAGGC GGGTCTCGAA CTCCTGACTT
22301 TGTGATCCGC CTGCCTTGGC CTCCCAAAGT GTTGGGATTA CAGGCATGAG
22351 CCACCATGCC CAGCCCATTT ATTTATTTTG AGACAGGCTC TTGCCCTGTC
22401 TCCCAGGTGC AGTGGCATGA TCATGGCTCA CTGTAACCTC TGCCTCCCTG
22451 GCTCAAATGA TTCTCCCACC TCCACAGTAG CTGGGATTAC AGGTGCGCAC
22501 CACCACACCT GGCTAGTTTT TTTATTTTTT GTAGAGATGG GGTCTCATT
22551 GTGTTGCTCT GGCTGGTCTC AAACTCCTGG GCTCCAGCGA TCTGCCTGCC
22601 TTGGCCTCCC AAAGTGCTGG GATTACAGGC TTGTGGCACC ATGCCTAATT
22651 TTTAAATTTT TTGTAGAGCT GGGGTCTCAC TGTGTTGCCC AGGCTGGTCT
22701 TGAACTCCTG GGCCATCTGC CCACCTCGGC CTCCCAAAGT GCTGGGAGTA
22751 CAGGCACGAG CCACCACATC CGGCCATCAA AATGTTTATC AAGCTTTTAC
22801 TATGTCCAGG CACCGCCCCA TGTGATGGGG ATACAGCTTG GCTTTTGAGC
22851 ATAGCCTTTC CTTAGGGCCT TTGCACATGC TGTTCCCCTA CTCCCTTGCC
22901 AACTGGCTGC TTCTTACCTT TCTGGTCTCT GCTTCAATAT CACTTCTGCC
22951 AGTAATTAGT ATTATTATTA TTATTTTTGA GACGGAATCT CACTCTGTCG
```

FIGURE 3J

```
23001 CCCAGGCTGG AGTGCAGTGG TGCGATCTTG GCTCATTACA ACCACCGCCT
23051 CCCAGGTGCA AGCGATTTTC CTGCCTCAGC CTCCCGATTA GCTGGGATTA
23101 CAGGCGCACA CCACCACGCC TGGCTAATTT TTGTATTTTC AGTAGAGACG
23151 GGATTTTGCC ATGTTGGCCA GGCTGGTCTC GAACTCCTGA CCTCAAGTGA
23201 GCTGCCCACC TCGGCCTTCC AAAGTGTTGG GATTACAGGC ATGAGCCACC
23251 GCACCTGGCC TCTGCCAGTA ATTATAAAAG AACAGTGAGA ACAGGCTTAG
23301 AATTACTGGG AACTTGTCTG ACCACTGTGC AAACCAGGCC CATCCCTATC
23351 AACATGGATC CCGTGTATCC TTCTGGGTAA GCACTAGAAT TCCAAGGTCT
23401 GCCTGGCATC CTCACCTGTG CTGGTTCCAC GTCCTGCAGG AAATTCCGCT
23451 GTCAGAAATC CTCACGGTGG AGTCCGCCCA GAACTTCAGC CTTGTGCCGC
23501 CGGGCACCAA CCCACACTGC TTTGAGATCG TCACTGCCAA TGCCACCTAC
23551 TTCGTGGGCG AGATGCCTGG CGGGACTCCG GGTGGGCCAA GTGGGCAGGG
23601 GGCTGAGGCC GCCCGGGGCT GGGAGACAGC CATCCGCCAG GCCCTGATGC
23651 CCGTCATCCT TCAGGACGCA CCCAGCGCCC CAGGCCACGC GCCCCACAGT
23701 AAGTCCTCCC ACCTCGGGTC CTTGAGAGAA TAGATCTAGA TGGGTGGGGC
23751 ACGGTTCTGG GGAATGGAAG GGCCAAAGAG GAAAGTGGGC AATGGTGGGG
23801 TTGAGAACGC AGCTTCTGGA CTCAGCAGGC CTGGGTTCAA ACTCTGTTAA
23851 TCACTCCTGT TAATCCCAGC GCTTTGGGAA GCCAAGGAGG GAGGATCACT
23901 TGAGGCCAGG AGTTCAAGAC CAGCCTGGGC AACATAATGA GATTCCATCT
23951 CTACAAAAAA TAAAAACAAT TAGCCAGGTG TGGTGGTGCA CACCTGTAGT
24001 TCCAGGTACT TGGAAGGCTG AGGCAGGAGA ATTGCTTGAG CCTGGGAGTA
24051 GTGAGTCATG ATTGCATCAC TGCACTCCAG TCTGGGTGAC AGAGCAAGAC
24101 TCTGTCTCCA AAACAGAAAA AACAACAACA ACAAAAATCC ACAACAAATC
24151 TCTGTTAAGC TCCTGGCCTG ATATGTGGCC CTGGGCATAT CACTTCCCCT
24201 CCATGAGCCT TGTCCCAGGT GCTGATAAGT CCTCATGCAC TTACTGAGTG
24251 CCTCCTCTGT GCGGGACAGT GCTGGGGACC CAGTGGTGGC CAGGACAGCC
24301 CAAGACCTGC CCTCATGGGG CTCAGAGTCC AGTAGGGCAG AATACCCATC
24351 TTCAGAGAGT GACAGTCCAG GGTGGGCAGG GTTGGGACAA GGAAGCTAGG
24401 GAGCTGGAGG AGCCCAGAGG GGTACCTGAC CCAATCTGGG TATATAGGGG
24451 GGCTTCCTGG AGGAGGTGAC ATCTGAACTG AGATCTGGAG GCCGAGGCAG
24501 GGTGAGATGT GGGAAAGAAA ATGGGAGGTC ATTTTAGGCA GAGGCAAAAA
24551 ATGTTGAGAG AGTACCAGGT TCCCACCCTC TGGAGCTTAT AATCCAGTGT
24601 GGGTGACAGA CATTGATCAT TAACCCATAC AAGCAACGAG TGTGATGCAG
24651 AGCATTTGCG AGAGTAATCC AACTTGGTCC TAGGAGTGAC ATTTGAGCTT
24701 ACACTTGAGG ATGAGGAGGA TTTAGCTAAG TCTAGGATGA AGGAAAGAGT
24751 ATTCCTGGCA GGGGAAACAG CATATGCAGA GACCAGAAGG CAGAAGAGAG
24801 TTTGCTGTAT TTGAGGCCGA GCAAGGAGGC CAGTGTGTCA GGAATAGCAT
24851 GTTGGGGGTA GAAGTCAGAG GTAGATGAGG GTCTAGGCCA TGGCTTTTAG
24901 GCCATTTAAG GGGCTCAGGC TTCTTCCTGA GGGCACTGGG GAGCCATGGC
24951 AGAGTTGTGA GCAGAGGAGG GACAGGGTCA GTCTTGTGCC TCAGTAAGAT
25001 CCCTCTGGTT TCTCTGTGGG AGGTGAGTAG GAAGGGGCAG GATTGGGGCA
25051 AGGAGACCAG GGAAGGGGCT GTGGGGTGAG GACCCAGAGT TGGGGGGCGA
25101 GCAGGGGCCT AGACTGGTGG AAGAGAGAGA CATTCAAATG GCAGAAGGAT
25151 CGGACTTTAG AAATGTCTGG CTCTGGTTGG GTTTGTAGGG GGAAAAGTTC
25201 AAGGGAAGAT GCAGGAGTCA GTCTGGGCTT TCCCTCCAAG ACTCAGTTTC
25251 CTTCTCTGTA CAATGGGGTC AGTCTGCCTC CCCTGGTGCT GAGATCCTGG
```

FIGURE 3K

```
25301 GGTAAAATGC TCAGCAAAAT CATCTGTAAC ATCACTCCTT TAGCCACTCA
25351 GCACATCTCA TTTACTCCTC CTGGTGGCTC TATGAGGGAG GTCCTTTTAT
25401 TATTCCCATT TTCTAGATGA GGAAACTGAG GTTCGTAGTG GACAAGTCAC
25451 CAGCCTGAAG TTGCACATTG TATCGAACAT TGGATTCAAA TCTGGGTGGC
25501 CTGACTCCCA AGTCTGCTTT TGCAGGTATG GGTGGAGATA ATCCTGAGCC
25551 TGGAGTCCCC TCACCTCTGT CTCTCCCCTC TCCCTAGGAC AAGCTTCTCT
25601 GAGCATCTCT GTGTCCAACA GTCAGATCCA AGAGAATGTG GTGAGACTTC
25651 CTGCCCCCAC CTGATGCCCT CCCCTCCCAC AAACCCTCCT CAGCTCTCTC
25701 GTCTCCTTGA CTCCCCCTTC CCCATTTCCA TTTGCACCCC TGACCTGCCC
25751 TGTCTTCACC CTGTAGGACA TTGCCACTGT CTACCAGATC TTCCCTGACG
25801 AAGTGCTGGG CTCAGGGCAG TTTGGAGTGG TCTATGGAGG TGAGGACACT
25851 TCAGAGCTAA CCCAGAGGGA GCCCCGGGCT GGGGGAAGCT GCTGTGGCTC
25901 CAGCCCTTTC TTTCTGGCTC CAACCCTTCC TTTCTGATTG GTCACATGCT
25951 CACCTCCCAT GTTGATTGGC TTAGCTAGAT CCTGGGTGGA CTGATTGCAG
26001 GTTCTCCTTT TCTCATTGGG AAAAACCAAT GGACATTCCT CCTGTTATTA
26051 ATAGGAAGGG TAAATTCGGC ACTCTGATTG GTCACAGAGG TAGATTTTGA
26101 TTGGATAGGG AAGGTAGATT CTGCACTCTG ATTGACCACA GAGCTAGAAC
26151 CTAGATTCTG ATTGGATAGA GTAGATTCTG CATTCATATT GGCCACAGAA
26201 CTAGTTCCTA GATTCTGATT GGAAAAGAGG GTAGATTCTG CACTCTGGCC
26251 ACAGAGCTAG ATCCTAGATT CTGATTGAAT AGGAGGGTAG ATTCTGCATT
26301 CTGATTGGCC ACAGGTCTAG ATCCTAGATT CTGATTGGAT TGGAGGGTAG
26351 ATTCTGCATT CTGATTGGCC ACAGGCTAAA TCCTAGATTC TGATTGTATG
26401 GGGCGGGTGG TAAATTTTAC ACTTTGATTT GCCACAGAGC TAGATCCTAG
26451 AGTTCAATAG GACAGGGAGG GTAACTTCTA CACTCTAAAC TCTAAGACTC
26501 AGTTTCCTTC TCTGTATAAT AGGGTCAGTC TGCCTCCCCT GGTGCTGGTG
26551 TCTCTCCCCT GTCCCCAGGA CTCTTATGGG TCACACAAAA CTAGATGCTA
26601 GATTCCGACT GGTTATAAAT CCAGTTTCCC ATGTTATACA TTCCCTTCTT
26651 CGGAGCTTTT TGTTTGTTTT TTGCTTTCCT TCTTTCTGCC TTTACTCCCA
26701 AGGTGCACCT CAGGTGGCCT TTTCACGTAT CTCCTGGGGC CTTCCAACTC
26751 TGCCCAACTC TGGCTGTCTC CATGGTGGGG GGCAGAGGTT GGCAGAGGTG
26801 GAGATACTCC TGCCAGGACT GGGTGGTCTT GCTCTCTCAT CCCCCATCTC
26851 TTCTACTCCC TGTGCAGGAA AACACCGGAA GACAGGCCGG GACGTGGCAG
26901 TTAAGGTCAT TGACAAACTG CGCTTCCCTA CCAAGCAGGA GAGCCAGCTC
26951 CGGAATGAAG TGGCCATTCT GCAGGTAACC ACCAGGCCGC CTTCCCTTTC
27001 TGCTTCTTCC TTTCATGGGC CAGCTGACCC AGTGTAGGGG TGGTCAGGGA
27051 AGGCTTCCTG GGGGAGGGCA TGTGCATGTT GAGACTGAAG GGGAGAAGGT
27101 GTTCTTAGCA GAGGGACCAG CCTGTACAAA GACCTGGTGA GAGGGAGCAT
27151 GAGGTTTTCT AGAAAGGAGG TACTGGGAGA TGAGGCCAGG GAGGAGGGCG
27201 GAGCCAGACC CTTTGGACTT TCTCCTGAGG GTACTGGAGA GCCACAGAAG
27251 GCTTTTGAGC AAGGGAGGGG CAGGATCAGG TGTGTACGTT AGGAAAATCC
27301 CGCAGGCTGC CATCTGGAGG GTGGGTGGAA AGGGAAGTGA TTGTAGCCAG
27351 GAGGCTGAGT GGGGATCTGG GTGGGAGAGA GGGGTTAGGC CAGGATAGGA
27401 CTGGAGAATG TGAGAGGGGG TATGGATTTA AAAGATACAG ATGTGCAGAG
27451 CTCTCCCCAT TTCTCCAAGC TCCCCCTCCT CCCTCCTGCA ACCCTGGGCC
27501 TCCACCAGAA TTTCAGGATG TAAAGATCCT TCTGGGCCGG GCATGGTGGC
27551 TCACGCCTGT AATCCCAGCA CTTTGGGAGG CTGAGGTGGG AGGATCACTT
```

FIGURE 3L

```
27601 GAGGCCAGAA GTTTGAGACC AGCCTGGCCA ACATGGCGAA ACCCCATCTC
27651 TATATTTAAA TAGAAAGAAA AAAAAGATCC TTCTGGGCAC CTGGCAGGTG
27701 GGGTGGAGGT GGGCCTGTTC TGTCTTGGCC TGTGGGAAGC CCCCTTCCCT
27751 CTCCAAGTGC CAATACCCCA GGGACATCCT TCTCCTTGTT TGTCATCCTC
27801 CTGCTCCTAT ACCTGACCCG TTGGGGTCTG AGTTTGTGGG TTACCTGGGC
27851 CCTGACCCCG CTCCCCACCC TGCAGAGCCT GCGGCATCCC GGGATCGTGA
27901 ACCTGGAGTG CATGTTCGAG ACGCCTGAGA AAGTGTTTGT GGTGATGGAG
27951 AAGCTGCATG GGACATGTT GGAGATGATC CTGTCCAGTG AGAAGGGCCG
28001 GCTGCCTGAG CGCCTCACCA AGTTCCTCAT CACCCAGGTG CGTCTGCCCT
28051 GCCCGCTGCC ACCCGCCCCT CCCCATCAGG TGTCAGCTTG GAGAGGCCCT
28101 GTATGCCTAG GGGGTCAAGC AGACACTTGG GGGAGTCACA ATAGCAGATA
28151 ACAGAAACCA TCATCAGGCT GGGCGCAGTG GCTCACACCC GTAATCCCAG
28201 CACTTTGGGA GGCCACGAG GTCAGGAGAT CGAAACCATC CTGGCTAACA
28251 TGGTGAAACC CTGTCTCTAC TAGAAATACA AAAAATTAGC CGGGCATGGT
28301 GGCAGGCGCC TGTAGTCCCA GCTACTCGGG AGGCTGAGGC AGGAGAATGG
28351 TGTGAACCTG GGAGATGGAG CTTGCAGTGA GCCGAGATCG CGCCACTGCA
28401 CTCCAGCCCG GGCGACAGAG CAAGACTCCA TCTCAAGAAA AAAAAAAAA
28451 AAAAAAAGGA ACCATAATCG TACAGAAGTA ATAATAACCA TAATAGAAAA
28501 AATAAGCCGG GCATGGTAGC ACGTGTCTGT GGTCTCAGCT ACTCAGGAGG
28551 CTGAGGCAGG AGGATCACTT GATCCCAGGA GTTCTGTGCT GATCAGGTGT
28601 CCTCATTAAG TTTGGCATCC ATGTGGTGAC CTCCCAGGAG TGGGGACCA
28651 CCAGGTTGCA AAGCAGCCCA GGTTGGAAAT GGAGCAGGTC AAAGCTCTCT
28701 TACTGATCAG TAGTGGGATC ACATCTGTGA AGAGGCATTG CACTCCAGCC
28751 TGGGCAACAT AGCGAGACCC CGCCTCTAAA AAGAAAGAAA GAAAAAAGAA
28801 AAATAATAGT GACAATAACA ATTAAAAATA AAGAGTATGC CAGGCGCGGT
28851 GGCTCACGCC TGTAATCCCA ACACTTTGGG AGGCCAAGGC GGGTGGATCA
28901 CCTGAGGTCA GGAGTTTGAG ACCAGCCTGG CCAACATGGT GAAACCCTGT
28951 CTCTACTAAA AATACAAAAA TTAGCTGAGC ATGGTGGCAG GCACCTGTAA
29001 TCATAGCTAC TTGGGAGGCT GAGGCAGGAG AATCCCTTGA GCCCAGGAGG
29051 CAGAGGTTAC AGTGAGCTGA GATCGTGCCA TTGTACTCCA GCCTGGGGGA
29101 CAAGAGTGAA ACTTCGTCTC AAAAAAAAAA AAAATAATAA TAATAATAAT
29151 AAAGAGTAAT CATAATAATA GAAAAAAATA GACTAGCGGT AATGATAGCT
29201 ATTTTTATTA TAAAAAATAA ATGATCAGTC AGGCTCCCTG GACCTGACTT
29251 GACTCATCTA GAAAAAAGGG GAGTCAGGCA TGGTGGGGTA CACCTGTAAT
29301 CCCAGCTACT CAGGAAGCTA AGGCCAGAGG ATTGCTTAAG CCCAGGAGTT
29351 TGAGCCAGCC TGGCAACAT AGCAAGAGCC CATCTCAAAA ACAGGCTGGC
29401 TCATGCCCGT AATCCCAGCG CTTTGGGAGG CCAAGGCAAG AGGATCGCTT
29451 GAAGCCAGGA GTTGGAGACC AGCCTAGGCG ACATAGTGAG ATCCCACCTC
29501 TACAAAAAGT AAAAAAAAAA ATAGAAAACC TAGCTGGATG TGGTGCCTGG
29551 TAGCACATGT CTGTAGTCCT AGCTGCTTGG GAGGAAGGGA GTGGAGAGGC
29601 TCTCTTGAAC CTAGGTGGTT GAGGCTGCAG TGAGCTATGA CCGTGCCACT
29651 GCACTCCAGC CTGGGTGACA GAGCGAGACC GTGTCTCAAA ACCAAACAAT
29701 AGAAAAAACG GGCAAGCAGC CCTTTTTCTC TCATTCATTC ATTCAGTTGG
29751 TCAACAAACA CTCCCTAGTC CCTGCTCTGT GCTTGGTCCC TTGCTGGTCA
29801 GTGTTGAGGA CACAGGGATG ACCAATACAG CCCCATTCTT AGACAGTGAT
29851 AGCTCAGGTG AGCAGGGCTA GGACAAGGGA GGCTGATAAT GGTGATGATA
```

FIGURE 3M

```
29901 AATAATGTGG TCACTAACAT TTATTGAGCA CTTACTATGT GCCAAGCACT
29951 CTTCAAACTC ATTTAATCTT CATAGTAACC TGTGCAGTAG GTGCTATTAT
30001 TATCAATCCC CTTTTATGGT TGAAGAAACT GAGGGTCAGA GACATCAAAT
30051 ATCTTGTCCA GGGTCACATA GCTGGTGGGA TTTGAACCTA GGATCTTTGC
30101 TTTTAACTAG TGATGTCAAA CTCATTTGTG TTACATTCAA ACAGATTTTC
30151 CTTGTGTGCC TGTGTGCCTG TGCTTTTTGT TTGTTTTTTT GAGACAGGGT
30201 CTCGCTCTGT CACCCGAGCT GGAGTGCAGT GGTACAATCA TGGCTCACTG
30251 CAGCCTTGAC CTCCCGGGTT CAAGCAATTC TCCTGCCTCA GCCTCCTGAG
30301 TAGCTGAGAC AACAGGCATC AGCCATCACA CCCAGCTAAT TTTTATAAAG
30351 ACATTTTTAT AAAGACTTGC TATGTTGCCC AGGCTGGTCT TCAACTCCTG
30401 GGCTCAAGTG ATCCTCCTGA CTCGGCCTCA GCCTCGCAAA GTTCTGGGAT
30451 TACAGGTGTG AGCCACTGTG CCCGGCCTCT GTTCTGCGTT TCTTTTTTTT
30501 TGGTGGAGGT GCACATTAGA TTCTTATCAC TTATATTGTT CAATGGTTTT
30551 ATCCCAGTGT TTGCCTCTTT ATTTTATATT TAGTTTTTAT TTACCATAGG
30601 GTTTTATTTA TTTTATTTTT TATTTTTTTT TGAGACGGAG TCTTGCTCTA
30651 TTGCCCAGGC TGGAGTGCAG TGGCACCATC TCGGCTCACT GCAAGCTCCG
30701 CCTCCCAGGT TCACACCATT CTCCTACCTC AGCCTCCCAA GTAGCTGGGA
30751 CTACAGGTGC CCACCACCAC GCCCGGCTAA TTTTTTGTAT TTTCAGTAGA
30801 GACAGGGTCT CACTGTGTTA ACCAGGATGG TCTCGATCTC CTGACCTCGT
30851 GATCCACCCG CCTCGGCCTC CCAAAGTGCT GGGATTACAG GTGTGAGCCA
30901 CCGCGCCTGG CCTATTTTAT TTTTTTTTTT GAGACAGGGT CTCATTTTGT
30951 CACCCAGGCT GGAGTGCAGT GGTGTAATCA TAGTTCACTG CAGCCTCAAA
31001 CTCCTAGGCT GAAGCAATTC TCCTATCTCA GCCTCCTGAG TTAACTGGAA
31051 CCACAGGCAT GAGCCACCAC GTCCAGCTAA TTTTTTTTTT TTTTTTTTT
31101 AATGTTTTG TAGAGACAAG GTCTCGCCAT GTTGCCCAGG CTGGTCTTGA
31151 ACTCCTGGGC TCGAGCGATC CTCCCATCTC AGTCTCCTGA GTTAGCTGGA
31201 ACCACAGGCA TGAGCCATTA CACCTGGCTA ATTTTTTTTT ATGTTTTTGT
31251 AGAGACAGGG TCTTGCCATG TTGGGTCTCG AACTCCTGGG CTTAAGTGGT
31301 CCTCTTGCTG CAGCCTCCCA AAGTTCTGGG TTACAGGCAT GAGCCACTGC
31351 GTCCAGCCGG CCATAGAGTG GAACTTTTAC GATGTTAAAT ATCCCCTTGT
31401 GTGGTTTCTG TGTTTCACAT CCTTCCTAGA AAGGCTTCCT TCTGGTGGGT
31451 GCCTTGCCTT CTTCTGAGAC ATCTCTGTGG GTCTCAGAGC CATCGTTGCT
31501 GTGTTCCCTT TACCCTGGCC CAGCACCCTT ATCCTCTCAG GCAGTGTGCC
31551 TGTGTTTGTC AGGCTGGCTT ATGGGGTGGG GACAGAAACC CACTGATGCA
31601 CCCTCATCCA GACTTTATTA TTTATGTATT TTTGAGACAG AGTCTCGCTT
31651 TGTTGCCCAG GCTGGAGCGC AGTGACACGA TCTCGGCTCA CTGCACCCTC
31701 TGCCCCCTGG GTTCAGGTGA TTCTCCTACC TCAGCCTCCC GAGTAGCTGG
31751 GATTATAGGT GTGTGCCACC ATGCCTGGCT AATTTTTGTA ATTTTAGTAG
31801 AGATGGGGTT TCATCATGTT GCCCAGGCCA GTCTCAAACT CCTGACCTCA
31851 AGTCATCTGC CTGCCTCAGC CTCCTGAAGT GCTGGGATTA CAGGCATGAG
31901 CCATCGTGCC CGGCCACATC CAGACTTCAG GTGTGGAAAG GAATCATGGT
31951 TCTCACAGGT GGCTGCTTTC AGCAGCTGAG GGGGTTTCTC TTTCTGGCCT
32001 TCATCTCTTC CTCTCTTTTT GCCTGCTCGC TCTTCTTTCT CTCTCTCTCT
32051 CTCTCTGCAG ATTTCTGCTT TCTGGGCTCT TGCCTGCCCC ACACCTAAGC
32101 CCTGTGCTAA GCCCTTTACC TCCTGAGCTT ATGTAGGCCT CACCACCATC
32151 CTAGGAGGTA GGTATTGTTA TAAACCCCAT TTTATAGATG AGGAAACTGA
```

FIGURE 3N

```
32201 GGCTCAGGGA GTTAGCAGTC TCCCTCGAGG TCACAGCCAA GTAGCTTTCC
32251 AGCCAAGATT TGAGTCTGGA TCTATCTAGC TTCCAACCTG CCCTCTTTCT
32301 TTTCTTTTTT TTTTTTTTTT TTTGAGACGA GTCTCACTC TGTCACCCAG
32351 GCTGGAGTGC AATAGTACAG TCTCAGCTCA CTGCAACCTC TGCCTCCCAG
32401 GTTCAAACAA TTGTCCCACC TCAGCCTCCT GAGTAGCTGG GACTACAGGT
32451 GCGTCCCAGT ACACCGGGCT AATTTTTGTA TTTTTAGTAG AGACGGGGTT
32501 TCACTATGTT GGCCAGGCTA GTCTTGAACT TCTGACCTCG TGATCCACCC
32551 GCCTCAGCCT CCCAAAATGC TGGGATTACA GGCGTGAGCC ACCATATCCG
32601 GCCAATGTTT TTTTTTTTTG GAGATGGAGT CTCGCTCTGT TGCCCAGGCT
32651 GGAGTGCAGT GGCGCTATCT CAGCTCACTG CAACCTCTGC CTCCCAGGTT
32701 CAAATGATTC TCCTGCCTCA GCCTCCTGAG TAGCTGGGAA CACAGGCACA
32751 CGCCACCATT CCTGGCTGAT TTTTGTATTT TTAGTAGAGA TGGGGTTTCA
32801 CCATGTCGAT CAGGCTGGTC TTGAACTTTT GATCTCGTGA TCTGCCCGCC
32851 TCAGCCTCCC AAAGTGCTGG GATTACAGG CGTAAGCCAC CGTGCCCGGC
32901 CTAACCTGCC CTCTTTGTTC ACATGAACTG GGAGAAAATC AACTGACAAA
32951 ATCTGGAAAT GGGCGGGGCG AGGTGGCTCA CGCCTGTCAT CCTAGAACTT
33001 TGGGAGGCCA AGGCAGATGG ATCACCTGAG GTCAGGAGTT TGAGACCAG
33051 CCTGGCCAAC ATGGTGAAAT CCCATCTTTA CTAATAATAC AAAAATTAGC
33101 CAGGTGTGGT GGCATTCACC TGTAATCCCA GCTACTGGGG AGGCTGAGGC
33151 ACAAGAATTG CTTGAACCTG GGAGGTGGAA TTTGTGGTGA GTCGAGGTCA
33201 TGCCGTTGCA CTCCAGCGTG GGCAACAGAG TGAGACTCCA TCTCAAAAAA
33251 ACAATCTGGA GATGACATAT ACAACACATG CATCTTTCCA GCTTGGTCTC
33301 CCAGTCTGTA GAATGAGGAG GTTGGTCAGG CATGGTGGGT CGTGCCTATT
33351 ATCTCAAGGT TTGGGTAGCT GAGGTGGGAA GATCATTTGA GGCCAGGAGT
33401 TTTAGACCAG CCTGGGCAAC ATAGCGAGAT GCCATCTCTA CAAAAAGATT
33451 TTTTTAAAAA AGAAAACAAT CAGAATAAAC ACAAGTATTT AAACTCTGAG
33501 ACAGATACAC AAGTATTTAA ACTCCGAGAC AGATAATAAT TGCAGTTGTA
33551 CAACACTCTA TGCTTCTGGT GTACTTGGCA TTTTGAGTTA CAGAGAATCA
33601 AGAAATATGA TTCTCACAGA TGAATGGTTA CAAATGGTAA TTTTTTTTTT
33651 AATCAGCTCA CCTTATCATA GGAACAGATA CAGCAGGAGA AGCTTTATTT
33701 AAGAGACACA AACAAATATA TTTACCAACA AGCCATCACA AAAATAATAA
33751 CTAATAACAA CAACAGTAAC AGCTAACATA CAGTGGTTAG CTATCCTAAG
33801 CGTTTTACAT GCATCTTTAG ATATGCTTTA AACCTTATAG CAACCTGTAA
33851 GGTTGGTACT CTTTTTTTTT CTGAGAGGCA TCTCACTCTG TCGCCCAGGC
33901 TGGAAGTGCA ATGGCGCGAT GTCGACTCAC TGCAACCTCC ACCTCTCCAG
33951 TTCAAGCGAT TTTCCTGCCT CAGCCTCCCG AGTAGCTGGG ACTACAGGCG
34001 CCCACCACCA CGCCTAATTT TTGTATTTTT AATAGAGGCA GGGTTTTGCT
34051 ATGTTGGCCA GGATGGTGTC TAACTCCTGA CCTCAGGTGA TCCACCTGCC
34101 TCAGCCTTCC AAAGTGCTGA GATTACAGGC ATGAGTCACC ATGCCCAGCC
34151 AAAGTTTTTT GTAAGGATGA AAAATATTTT TTTTAAAAAT GAAATCAGGC
34201 TGGGCACAGT GGCTCACGCC TATAATCCCA GCACTTTGGG AGGCCAAGGT
34251 TGGTGGATCA CGAGGTCAGG AGTTCAAGAC CAGCCTGACC AACATGATGA
34301 AACCCCGTCT CTACTAAAAA TACAAAAATT AGCCGGGCAT GGTGGTGTGT
34351 GCCTGTAATC CCAGCTGCTC AGGAGGCTGA GGCAGGAGAA TCAGGAGGCC
34401 TTCTCAAAAA AAAAAAAAAA AAGGAATCAA AGCCCGACAT GGTGGTGGTG
34451 GCACATGCCT GTAGTCCTAG CTATTTGGGA GACTGAGGCT GGAGGATCAC
```

FIGURE 30

```
34501 TTAACCCCAG GAGTTTGAGG CTGTAGAATG ATACTGCACT TCAGCCTGGG
34551 TGACAGAGGG AGACTCCATC TCTTCAAAAA AAAAATGGGT GAGGTGGGGG
34601 TGGCTCACGC CTGTTATCCA AGCACTTTGG GAGGCTGAGG TGGGTGGATC
34651 ACTTGAGTGC AGGAGTTTGA GACCAGCCTG GGCAACATGG TGAGACACTG
34701 TCTCTACAAA TACAAAAATT AGTCAGGTGT GATGGTGTGT GCCTATAATC
34751 CCAGTTACTA GGGAGGTTGA GGTGGGAGGA TGGATTTAGC CTGGGAGGTC
34801 GAGGTGCAGT GAGCTGTGAT CCCGCCTCTG TGCTCTGGCC TGAGTGACAG
34851 AGCAAGACTC TGTCTCAAAA AAAAAAAAAA AAAAAATAGA ATCACATAGT
34901 TGGATCTTGG AAATGCCTGC TCTGTGAGTA GCATTCAGGA GTTTACCACA
34951 TGCTAGAAGA TCTTGGGATC TTACAGCCCC ACTCATCTAG CCCAGACTTT
35001 CTAGTTTACA TTTAACTCTT ATCTCTCAGA TGTAAATGGT TCTATGATTC
35051 TGAGATTCTT TGGTGCTCCA GTGCCTCCTG TTTCCCTGGC TGGGGTGTCT
35101 GCAGGGGTGT GTAGGAAGGC ATGGATGGGG CCAGGCGCAG TGGCTCACTC
35151 ACGCCTGTAA TCCCAGCATT TGGGAGGCC AAGGTGGGTG GATCACTTGA
35201 GTCCAGGAGT TTGAGACCAG CCTGGTCAAC ATGGTGAAAC CCTGTCTCTA
35251 CTAAAAATAA AAGAAAAAAT TATCAGAGCA AGTCTGGGCC CGGTGGCTCA
35301 CGCCTGTAAT CCCAGCACTT TGGGAGGCCG AGGTGGGGGA ATCACGAGGT
35351 CAGGAGTTTG AGACCAGCCT GGCCAACATG GTGAAACCCC ATCTCTACTA
35401 AAAATAGAAA AAATTAGCTG GCATAGTGG CCAGCGCCTG TAATCCCAGC
35451 TACTCGGGAG GCTGAGGCAG GAGACTCACT TGAGCCCTGG AGGTAGAGGT
35501 TGCAGTGAGC CGAGATCGTG CCACTGCACT CCAGCCCAGG CGACAGAGTG
35551 AGACTCCGCC TCAAAAGAA AAAAAAAAT TAGCTGGGCA TGGTGGTGCA
35601 CGCCTGTAGT CCCAGCTACT TGGGAGGCTG AGGCAGGAGA ATCACTTGAA
35651 CCCAGGAGGT AGGGGTTGCA GTGAGCTGAG ATCATGCCAC TGCACTTCCA
35701 GCCTGGGCTA CAGAGCGAGA CTCTGTCTCA AAAAAAAAAA AAAAAAAGTA
35751 TGGATGGGTT TGGAGGGCTG GCTGCTGAGG TTGGGATTTG GCTGAGTACC
35801 TATCTACCTT TCCTTACTGG GCCCATCTGC TCCCCTCAGA TCCTGGTGGC
35851 TTTGAGACAC CTTCACTTCA AGAACATTGT CCACTGTGAC TTGAAACCAG
35901 AAAACGTGTT GCTGGCATCA GCAGACCCAT TTCCTCAGGT CAGTTATGTC
35951 CCCTCCTGAT TTGGGGAAAT CCAGGCAACA CTGATGGCCG GGGTGGGGGT
36001 GGGGAAGGGG ATTATACTAA TCAAGATGTG GGGGCGAGGC ACAGTGGCTC
36051 TTGCCTGTAA TCAGCATTTT GAGAGGCTGA GGCAGGAGGA TCATTTGAGC
36101 CCAAGAGTTT GAGACCAGCC TGGGCAACAT AGCGAGACCT CATCTATACA
36151 AAAAATGAAA AAAAAAATAG CCGGGAATGG TGGCGTGCGC CTATAGTCCT
36201 AGCTGCTTAG GAGGCTGAGA TGGGAGGATT GCTTGAGCCC AGGAGTTGGT
36251 GGCTGCAGTG AGCTATGATT GTGCCACTGC ACTCCAGCCT GAATAACAGA
36301 GTGAGAGCTG TCTCTTAAAA AAAAAAAAAA AAGACTGGGT GCGGTGGCTC
36351 ACGCCTGTAA TCCCAGCACT TTGGGAGGCC GAGGCGGGCA GTTCACGAGG
36401 TCAGGAGATC GAGACCATCC TGGCTAACAC GGTGAAACCC CTTCTCTACT
36451 AAAAATACAA AAAAAATTA GCGGGGCGTG GTGGTGTGTG CCTGTAGTCC
36501 CAGCTACTTG GGAGGCTGAG TTAGGAGAAT GGCATGAACC CGGGAGGCGG
36551 AGCTTGCAGT TAGCCGAGAT CACGCCACTG CACTCCAGCC TGGGTGACAG
36601 AGCGAGAGAG CGAGACTCTG TCTCAAAAAA AAAAAAAAAA ATATATATAT
36651 ATATATATAT ATAGTTTATC CCAACATATA GCACTTTATT CAACATGTAG
36701 TCAACATAAA AATTATTAAG GCCAGGGGAG GTGGCTCATG CCTATAATCC
36751 CCGCACTTTG GGAGGCCAAG ATGGGAAGAC GGCTTGAGAC CAGGAGTTCA
```

FIGURE 3P

```
36801 AGTCTGAAGT GAGCTATGAT TGTGCCACTG CACTCCAGCT GGGGTGACAG
36851 AGCAAGACCC TGTCTCTTAA AAAAGAAACA AAACTCAATG AAACATTCTG
36901 CTTGTTTTTC ATACTATGTC TTCAAAATCT GGTGTGTATA ACAGTTGGGG
36951 AAATAGATTG ACATGCCCAA GTTGTTCCAA ACATATTTAA AAGTTTTCTG
37001 GTTGGGCGCA GCGGCTCATG CCTATAATCC CAGCACTTTG GGAGGCTGAG
37051 GCGGGCAGAT CACTTGAGGT CTGGAGTTGG ATACCAGTCT GGCTAACATG
37101 GCGAAACCCC GTCTCTACTA AAAATACAAA AATTAGCTGG GCATGGTGGC
37151 GGGAACCTGT AATCCCAGGT TCTCAGGAGG CTGAAGCAGG AGAATTGCTT
37201 GAACCCAGGA GGGTGGAGGT TGCGGTGAGC CGAGATCACA CCACTGCACT
37251 CCAGCCTGGA CGACAGACCA AGACTCGTCT CAAAAAAATA ATAATAAAAT
37301 AAAAATTTTA AAAAAGATCC ATAGGAAAGT ATAGATCTTG GAAAAGAGAA
37351 AGAGCTATAA GATCTGTAGA AAGGGCAGAG TACCTCAGGA AAGGGTGGCT
37401 GTCACATTGA GATTCAGGTC AGGGGTTGAG GCGTGGCTGG TTTCAAAGGT
37451 GACAGAGGCT TCAGGCTTCA AGGATTTGGG GCTCTATCCT GCAAGCAACA
37501 GTGAGCCAAG GAAGGGTTTT GAACAGGGAA AGGACAGTAC ATGAACAGAG
37551 CTGGGAACCA AGGCTGAGAG GTAGGCAGCA GAGCAAGACC TTGAACCCAG
37601 GTCTTGCTGG CTCCAAAGCC TGTCCATGAC CTTAGACTGC AGCCATTAAC
37651 AATGAGGGTA TGGGGCCAGG TGTGGTGTCT CATGCCTGTA ATCCCAGCAC
37701 TTTGGGAGGC TGAGGCAGGA GGAACACCTG AGGTCAGGAG TTTGGGACCA
37751 GCCTGGCTGA TGTGGTGAAA TGTCGTCTCT ACTAAAAATA CAAAAATTAG
37801 CCAGGCATGG TGGCGGGTCC CTGTGATCCC AGCTATTCGG GAGGCTGAGG
37851 CAGGAGAATT GCTTGAACCC GGGAGGCAGA GGTTGCAGTG AGCCAAGATC
37901 ACGCTACTGC ACTCCAGCCT GGGCGACAGA GCGAGACTCC GTCTCAAAAA
37951 AAATAAAACA ATGAAGGAAA GGTAGGCATA CACCATACTG TCTGCCAGCT
38001 ACCGCAGTCA GCACCCACTC CTACCTAATC CCCAGGAAAG CCTGAGAGGA
38051 GGCTGCTATC AACAACCCCC CAATACAGAT GACAAAATCA AGGCCTGGAG
38101 AAATTAGGTC CTTGACCTGA GATCATCGAG GGTCATTCTG TGCTAGACAC
38151 TGCTCCTAAC ACGTTGCATA CATTTCTCTT TCAGTCTAAA CAAGCACCCT
38201 TTAAGGTAGG GACTGTTAAG ATCTCCATTA TGTTTCATGT TTTTTTTGTT
38251 TGTTTTTTGA GACGGAGTCT CGCTGTGTCA CCCAGGCTGG AATGCAGTGG
38301 TGCGATCTCG GCTCACTGCA ACCTCTGCCT CCCAGGTTCA GGCGATTCTC
38351 CTGCCTCAGC CTCCTGTAGT AGCTGGGACC GCAGGCGTGT GCTAATTTTT
38401 GTATTTTTAG TAGAGATGGG GTTTCATCGT GTTGGCCAGG CTGGTCTCGA
38451 ACTCCTGACC TCAAATGATC CATCTTCCTT GGCCTCCCAA AGTGCTGAGA
38501 TTGCAGGCAT GAGCCACCAC GCCCCAATCA TGTATATTTT GAGGCTATTA
38551 AAAAAAATCT GCATTATTCA AAAGAGGAAA CAGCGACCCA TTGGAGGTGG
38601 CAGAGGTATA GCAGCAGCTA GCATTTATTG TGCACCAACT GAATGCCAAA
38651 TATTGTCCTG TGGGCTTTGG ATGGTTTAAT TCACTAACCA TCATGGCAGT
38701 CCTCTGAGAT AGGTGCTCTT CTGCTCTTCT TCCTATAGAT GGGGAAACTG
38751 AGGCACAGAG GGGGAAGTC ACCTGCCCAG GGTTGCTCAG CTAGTGAGCC
38801 AAGGAGCCTG GATTCAAACC AGCATCCAGC TTTCTCTGGA ATACCATGGA
38851 GGGTGGTGTG GTGGGGATGC TGGGGTGGGT GCGGCTCCAT CACCTGGTGG
38901 AGCCTCCATC CCTTGCCCTC TGCAGGTGAA GCTGTGTGAC TTTGGCTTTG
38951 CTCGCATCAT CGGCGAGAAG TCGTTCCGCC GCTCAGTGGT GGGCACGCCG
39001 GCCTACCTGG CACCCGAGGT GCTGCTCAAC CAGGGCTACA ACCGCTCGCT
39051 GGACATGTGG TCAGTGGGCG TGATCATGTA CGTCAGCCTC AGCGGCACCT
```

FIGURE 3Q

```
39101 TCCCTTTCAA CGAGGATGAG GACATCAATG ACCAGATCCA GAACGCCGCC
39151 TTCATGTACC CGGCCAGCCC CTGGAGCCAC ATCTCAGCTG GAGGTGCCTG
39201 GGGCCCGCCT ACCCCATGGG CGGGTGGGTT GTGGGGTGGG GCTGGAGAAG
39251 TGGGCGGAGC CATGAGAGGG GGGTGGACCC GGAAACAGCC TGGCACCTTG
39301 GGGGTGGAGC CCAGTGCTGG GGCGGGCCTA CTGGAGGGAT GTGGCTACAG
39351 GAGGAGCCGT CCTGTAAAAG ATGGGCTGGG ACTCAGGCCT AGACTAGGTT
39401 ACTTGGGCTG GAAACCAAGT GCCCCAGAAG CGCTGAGGAC ACTTGGAACC
39451 TTAGGGGGGC TGAGTGAGAC TTGGCTTGTC TAGGGTGGGA CCAGGAAAGG
39501 GACTGGACTT GAGGGTACCA AAGGGCTGCG GTGACCAGGA GAAGGGGCTG
39551 AGCCTCCCAA GGCATTGGCT GGGACCTGGA GCCTTTGGGT TTACGACCCC
39601 AAAAGGGTCA GCCTTGCAAA AAGGAGGCAC CGGTGGGTAG GGTTGAGAAA
39651 CAAGGGCATG GCTACTTTGC TGTGTACTGG GGCCGTGACT TGGGTGAAGA
39701 TGGGCCTGAA GCCTGGGGTC GGTTCAGTGA CCAAGGGAGC CAGTCTAGGG
39751 ACGTGGCCGT GGAGGGTTTC CGAAGAGGTC CAGGAACAGG GCTGACCCTG
39801 AGTCCTGGAA GCTGGGAGTG GATGGGAGTG GGGAGGAGAA GGGAGCCAGG
39851 ACTGAGGCAG ACATTGCACT CTGCATTCTG GGGCTTTGGT GTTGTGGCTG
39901 GGCCTGATGA AGTGGCACCG GGCCTGGTGA CTTGAACCTA CTTGGGAATG
39951 GGTCTGTAAC TTTCCCTGCT TGGAAAAGTT AAGTCCTAAG GCCTGGAGCT
40001 TTGAGGCTGG GTGTGGGATG GCATGTTTAG AGGGCCAGAG GCAGGGCTAA
40051 GATACTGGGG TGTGTCAGAA GCCAGGAGAA CAAGGGACCT GTGTTGGAGC
40101 CAGGGAGCTC AGGAAGACAG ATGGAGTATG GAAGGGGGG GGATCATTCA
40151 TTCATTTATT TATAACCATT TATTCAACAA GTACATTCAT GTATTTGTAA
40201 CCATTGATTC AACATGTTGA GTGCCCACGA TGTGCCAGGC ATTGACTGTT
40251 CCAGCTCTGG GAATACTGTG ATGACTTGGA CAGAAGGGGT CAGGTGCAGG
40301 GTAGCTCATT GAGTGGTCCG CGAAGGGTGG AAAGGGGAAG GGTCCTCTCT
40351 GGAGGGTGCG GCTTCATGGA GCAGGTGGAG CAGGGTGACA CGGAGGTTGC
40401 TCGGTGCAGG ACAAGACAAG GTCTTGGTGG TGGTCTAAGA GCATGGGCCC
40451 TAAGCAGTGA GAATGTGGAT TGACTTGAGT CCTGGAGTAA TATTGGGGGT
40501 GCTCAACACT GGCTTTTTTT TTTTTTTTTG AGGTGGGGTC TCGCTCTTTC
40551 ACCCACGCTG GAGTGCAGTG GCGTGATCTC GGCTCACTGC AACCTCCACC
40601 TCTTGGGTTC AAGGGATTCT CCTGCCTCAG CCTCCCGAGT AACTGGGATT
40651 ACAGGCACAC AGCACCATGC CTGGCTCATG TTTTATATTT TTAGTAGAGA
40701 CAGGGTTTCG CCATGTTAGC CAGGCTGGTC TTGAACTCCT GACCTCAAGT
40751 TATTTGCCCG CTTCAGCCTC CCAAAGTGCT GGGATTGCAG GCATAAGCCA
40801 TCACACCCCG CCAGCATTGT CTTTTGAGAC CCACTCAGAA GTCCCTCAGT
40851 AAAAGTGCAT CGAGTGTGCA CAAGTGAATT TAAGTGTGGT TGCACCTGTG
40901 TGAGGATCAC AGAATCCTGT GGGTGTTGAC GGGAGCAGGG TGCCTGTGTG
40951 CACCAGGCCT CTCCTCGGAT GGGTTCATAC AGTGAAGCCT TGTCCTTCAT
41001 GGCTTCCCAT CAAGGAGAGA GCCTCGGATG AGTGCTGGCT TGTCTTGAAG
41051 CTTGACATTC GCTAGTCCTC TTTTTCACAA TGAACAGGCC TATCTCTGAG
41101 CCTTCTGCAG GCAATGGTGA CTAACTACCA TCTGATGACA TTTTGTTTTG
41151 TTTTGTTTTG TTTTGAGACG GAGTTTCGCT TTGTCACCC GGGCTGGAGT
41201 GCAGTGGCAC GATCTTGGCT CACTGCAACC TCTGCCTCCT GAGTTCAAGC
41251 GATTCTGCCT CAGCCTCCTG AGTAGCTGGG ACTACAGGCA TGCGCTACCA
41301 TGCCCAGCTA ATTTTTTGTA TTTTTAGTAG AGACGGGGTT TCCGTGTTGG
41351 CCAGGCTTGT CTCGAACTCC TGACCTCGGG TGATCCACCC GCCTCGGCCT
```

FIGURE 3R

```
41401 CCCAAAGTGT TGGGATTACA GGCATGAGCC ACCGCGCCCA GCCTGATGAC
41451 ATAGATGCTC CCTGATTTGC ACTGGGGTTA GATAAACCTG ATAAACCCAT
41501 TGCCCATTGT AAATTGAAAA TATCATAAGT TGGTCAGGCG CAGTGGCTGA
41551 AGCCCATAAT CCCAGCACCT TGGGAGGCCA AGGTAGGCAG ATTGCTTGAG
41601 CCCAGGAGTT CAAGACCAGC CTGGGCAATG TATCTCTACA AAAAATACAA
41651 AAATTAGCCG GCCATAGTGA CAGGTGCTTG TAGTCCCAGC TGGCTGCTCA
41701 GGAGGCTAAG GCAGGAGAAT CAATTAAGCT GGGGAGGTGG AGGCTTCAGT
41751 GAGCATTGAT CACGCCACTG CACTTCAGCT TGGGTAACAA TGAGACCCTG
41801 TCTCAAAAAA AAAAAAGGAA GTATTGTAGG TTGAAAATCC ATTTAGGCCG
41851 GGCGCAGTGG CTCATGCCTG TAATCCCAAC AATTTGGGAG GCCAAGGCAG
41901 GCGGATTGCT TGAGGTCAGG AGTTAGAGAC CAGCCTGGCC AATATGGTGA
41951 AACCCCATCT CTACTAAAAA TACAAAAAGT TAGCAGGACA TGGTGACACA
42001 CACCTGTATT CCTAGCTACT TGGGAGGCTG AGGCAGGAGA ATCACATGAA
42051 CCCGGGAGGC GGAGGTTGCA GTGAGCCAAG ATCGTGCCAT TGCACTCCAG
42101 CCTGGGCGAC AGAGCGAGAC TCTGTCTCAA TAAATAAATA AGTAAAAATA
42151 AAAAGAATAG TACAGGTGTA ATTGTATGTA CCTGTATATG ACAAAAAGAA
42201 AAAAAAAGGT GACATAGGGG AATGGGGAAA TTGAAGTAGA AACAGGTGA
42251 AGAGAGGGAG CTGGTGTGAA CATGCATGGG CAGGAGGAGA CAAATTTGTA
42301 ATGTAATGAG GAAATGGGTG GGTGAGTGAT TGGCACAGGT GAGGCTTCTG
42351 AGCCACCTGA GCTGGTGCAG AAGGAAGGTG TTGATGGCAG GCAGGTAGGC
42401 TAGGGGGTGC CTATTGGAGG AGGAGTGACC CTTGACCTGT AGGGCTTGAC
42451 CTGTTTCTCT TTCCTGTGCA GCCATTGACC TCATCAACAA CCTGCTGCAG
42501 GTGAAGATGC GCAAACGCTA CAGCGTGGAC AAATCTCTCA GCCACCCCTG
42551 GTTACAGGTG ATGCAGGGGG CAGGGCTGGC CCATTGGCTG GATTGGAGGA
42601 AGGGGTGGGA GTAGATCGCT TATTGGCTAG GCAGGTTGTG AAGGATGTAG
42651 GTTTCCTTGG GTCTGGAATG TGGCTAGGCC TCCCATTGGC TGGGTGCAGG
42701 AAGAGGGGGT GGAGCTAAAT GTCTACTGGC TGGGTGGGTT GCAGAGGGTA
42751 TGGCTTCACC TTCATTGGTA CCCAGCTCTC AGTGGCAAAC CAGAGGATAT
42801 CCAGGCACTG CTCCAATGCA GACCCCAAGC TAACCCCAGT TCTCTCGGGC
42851 CCAGGAGTAC CAGACGTGGC TGGACCTCCG AGAGCTGGAG GGGAAGATGG
42901 GAGAGCGATA CATCACGCAT GAGAGTGACG ACGCGCGCTG GGAGCAGTTT
42951 GCAGCAGAGC ATCCGCTGCC TGGGTCTGGG CTGCCCACGG ACAGGGATCT
43001 CGGTGGGGCC TGTCCACCAC AGGACCACGA CATGCAGGGG CTGGCGGAGC
43051 GCATCAGTGT TCTCTGAGGT CCTGTGCCCT CGTCCAGCTG CTGCCCTCCA
43101 CAGCGGTTCT TCACAGGATC CCAGCAATGA ACTGTTCTAG GAAAGTGGC
43151 TTCCTGCCCA AACTGGATGG GACACGTGGG GAGTGGGGTG GGGGGAGCTA
43201 TTTCCAAGGC CCCTCCCTGT TTCCCCAGCA ATTAAAACGG ACTCATCTCT
43251 GGCCCCATGG CCTTGATCTC AGCACACGGC ACTCTCGAAT CATTACTCTG
43301 TTGTACCAAC ATGGAGTTCA TCTGGAAGGA GGACTGCCTG AAAAGAGGAA
43351 GGATGGAAGG GGTGGGGAGA GAGGACTGAT GGGAGAGGAG TCTTGGAAGG
43401 AGGACGAGCT GGGGTAGAAA ATATACAGGA AGAGTGCCAG GAGAGAAGAT
43451 GAGAAGGGAG AGGGAGGAGT AATGGAGGAG GAGTTGGAAA CTGGGGAGAG
43501 ATGGAAGGAA TGTGACTGGA GGGTAGAGAA CTTGGAGAAA AAGTAATCTC
43551 ATGGTTTGTG ATGACTGATT TTTTATTTGG TGGTGGTGTT ACTACTAATC
43601 ACAACTATTA ATTCAGGCTG GGTGTGGTGG CTCATGCCTA TAATCCCAGC
43651 AATTTGGGAG GCCGAGGCAG GCAGATCCCT TAGATCTCAG GAGTTTGAGA
```

FIGURE 3S

```
43701 GCAGCCTGGC CAACGTGGTG AAACTCCCTT TCTACAAAAA GTTCAAAAAT
43751 TAGCCAAGTG TGGTGGCTTG CACCTGTGGT CCCAGCTACT TGGAGGTTGA
43801 GGCTAGAGGA TCGCTTGAGC CCAGGAAGCA GAGATTGCAG TGAGCCAAGA
43851 TCACACACCA CTGCACTCTA GCCTGGGCAA GAGAGTGAGA CCCTGTCTCA
43901 AAAGTCAAAT AATAAAATGC AGTTAGCCCA AGTCTGATCC ATACTAGAAA (SEQ ID NO:3)
```

FEATURES:
Start: 1191
Exon: 1191-1430
Intron: 1431-3561
Exon: 3562-3700
Intron: 3701-6524
Exon: 6525-6656
Intron: 6657-12915
Exon: 12916-13070
Intron: 13071-13173
Exon: 13174-13396
Intron: 13397-16453
Exon: 16454-16531
Intron: 16532-16613
Exon: 16614-16767
Intron: 16768-19715
Exon: 19716-19833
Intron: 19834-20331
Exon: 20332-20409
Intron: 20410-23439
Exon: 23440-23698
Intron: 23699-25587
Exon: 25588-25640
Intron: 25641-25766
Exon: 25767-25839
Intron: 25840-26867
Exon: 26868-26974
Intron: 26975-27875
Exon: 27876-28037
Intron: 28038-35839
Exon: 35840-35938
Intron: 35939-38925
Exon: 38926-39193
Intron: 39194-42471
Exon: 42472-42557
Intron: 42558-42854
Exon: 42855-43064
Stop: 43065

FIGURE 3T

CHROMOSOME MAP POSITION:
Chromosome 19

ALLELIC VARIANTS (SNPs):

| DNA Position | Major | Minor | Domain | Protein Position | Major | Minor |
|---|---|---|---|---|---|---|
| 638 | T | C | Beyond ORF(5') | | | |
| 1696 | T | C A | Intron | | | |
| 2220 | A | C | Intron | | | |
| 2718 | A | C | Intron | | | |
| 2905 | G | T | Intron | | | |
| 4136 | T | C | Intron | | | |
| 4846 | C | T | Intron | | | |
| 6409 | A | G | Intron | | | |
| 8088 | C | T | Intron | | | |
| 8228 | C | T | Intron | | | |
| 8478 | G | A | Intron | | | |
| 9831 | T | C | Intron | | | |
| 12341 | G | A | Intron | | | |
| 12631 | A | T | Intron | | | |
| 13168 | T | C | Intron | | | |
| 13572 | - | G T | Intron | | | |
| 14789 | A | G | Intron | | | |
| 15528 | A | C | Intron | | | |
| 17865 | C | T G | Intron | | | |
| 17865 | C | T G | Intron | | | |
| 19005 | A | G | Intron | | | |
| 19273 | C | G | Intron | | | |
| 24406 | A | T C G | Intron | | | |
| 24751 | C | T A | Intron | | | |
| 26208 | C | G | Intron | | | |
| 26522 | G | A C T | Intron | | | |
| 26577 | T | A G C | Intron | | | |
| 26981 | T | C A G | Intron | | | |
| 28409 | C | G A T | Intron | | | |
| 29179 | A | T | Intron | | | |
| 30276 | A | G | Intron | | | |
| 30320 | C | T | Intron | | | |
| 30502 | G | A | Intron | | | |
| 31348 | - | T | Intron | | | |
| 33403 | A | T | Intron | | | |
| 33554 | C | - | Intron | | | |
| 33558 | C | - | Intron | | | |
| 34192 | G | A | Intron | | | |
| 37005 | A | G | Intron | | | |
| 37429 | A | G | Intron | | | |

FIGURE 3U

| | | | | | | | |
|---|---|---|---|---|---|---|---|
| 37725 | C | T | Intron | | | | |
| 37870 | C | T | Intron | | | | |
| 39209 | C | T | Intron | | | | |
| 42934 | C | T | Exon | 835 | A | V | |

Context:

DNA
Position
638     GAGGCCCCGGGCCCACCCTCCCCTTCCGCCCCCGGCCCCTCGGCAGGCTCCGCCCCTCTC
TGACGTCGCCGAGGCCCGCGCCGATTGGTCGACTGCACTGTCGCTCCGGACACTTCCTCC
TGGGCCGCCGCCGCCGCCGCCGACTTAAACTTTGGAGGGGGAAAAAGAGCTACTGGCGCC
TGGCGACCCTCCCTGCCCCCCACCCAACCCCGCTCCGGCAACGCCCCCTTCCTCACGGCT
CCCGACCGAACTTTTCTCCAACTTCTGCGACTCGTGAGATTCCCTTCTACCCACTCCGGC
[T,C]
CTCGGGACCCCTCTGCCCATCCCCTGGCCGGTCGGGTCCCTGCGAACCCCTTTATCTCTG
GAATCCACTCGGTCCCCGACTCAGAGACTCCTGCCCTCCACCCCCAAGGTGAATTCCCCC
GGGCCGCCTTCTGAGTGGGATCCTCTTCTTGGAGCACTGGATCCTGGGATTCCCTCTGCC
CCCTTCTCAATCCCTCCTCTAGGGAAGGGGCCTTTGAATCGCGGGCTCTCCTGATCCCTG
TGACCCCGACCTACTAGATTTCCTCTCAGGCTTCTTGGAATCTCAATCGCTGGGACCTCC 1696     TGAAGCAGCTGGCCTGTTCCATCGTGGACCAGAAGGTGAGGGCGCAGGCTCCCTGGATCC
AGCTCGGGGAGAGGTTGAAGGAGGGGGCGCTGGCAGAGGGGTCTGGGGCCTGGTGTGCGG
AAGAGGGAGGAAGGAGACCTGAGCTTTGGGTGATGGAGGGATAGGGGGCATTGCCCCCCT
TCCATTGCCCCTCTCCCCACCATCCCTTTGAGAGAGGACTGGGCAGGGGTGGGGTGCCCC
AGAGGCCTCCCCAAATTTCATGTCCCTGCATGTCGTTGTTTTCTGCAGCAAACAGGGAGG
[T,C,A]
AGGGAGGGGCCAGCCAGGTGTAGAGAGGGGAGGAAGGGGCAGCAGATGTCGGCGGACCTC
CACGTCCAGGCCCATCCCCGGGCCTCCCATTTGGTGGAAACAGGAGAAATTGAACCCGGGC
TGGCCATGGTGATCCGGTGACATGTGTGGGTGCAGGTGCTTGAGTTAGCTGCCAGGGGCA
AGTGAGGTCTCGGAGCCCAATTCTGCCCTCCCCTAAGCCTGAGATATGTGTGGAGGGGCA
GGCACTCCTACAGACCCTGGGGACTCTATTCCCTTTCCTAGTCACAGTGCTGTTAGCCTA 2220     ATATGTGTGGAGGGGCAGGCACTCCTACAGACCCTGGGGACTCTATTCCCTTTCCTAGTC
ACAGTGCTGTTAGCCTACTCTTAATTTTTGGACACCAGGGTCCCCAGGGTGGGCAGCTGGG
TGTTATGGCAAGAGGAAACCAGGTGGAACTCCACGTCTAAACCGTGAAATGTTAAAAGAA
TAGTGGGCTTCTGTGTTGGAGTACTGGACTGTAGAAATGTTAGAATATTAGAATCATAAC
TTGTTGGAATATGCATCCTAGGCAATTAAATTGCCCCCATGTTCGTGTTCAAATATTAGA
[A,C]
TTCTAGGTTTGTGAAATAGTAAAACATTAAAATGCTGGAATATTAGATTCCTAGATTGTT
GAATCCTAGAAAGTTAAAATGTTAGAATTTTAGAATGCTGGATGGATGAGGTCCTTGAAT
GCTAAAGAATTCAAAGAGCACAGTCCTAGCTTGTCAGACTCCTAGAATATTAAAATATTA
GATTACCGCTTATTTAGGTTATTGAAATCCTAAAATGTATAGTGATACCAGGTAGGAATC
TAGAATGTATAATTCTATAATGTGAGCATGTTGGAGTCCCAAAATATCCAAATTCCAGAA

2718     GTTATTGAAATCCTAAAATGTATAGTGATACCAGGTAGGAATCTAGAATGTATAATTCTA

FIGURE 3V

```
        TAATGTGAGCATGTTGGAGTCCCAAAATATCCAAATTCCAGAATCTTTTCAGACTCCTGG
        AAATGAATCCTTTGGGCATCAGAGAAACGTGGGGAACTGGGCCAGCTCCCCCATTCTACA
        GACAAGGAAACTGAAGCTTAGAGAAAAACTTCCCAAGGGGTCAGGGCCAAGGCAGTCCTG
        GTCTTCTGTGGACTCTCTCTTAGCAGTGAGAACTGATAGGGTTTTGCCCACCAAATGCCT
        [A,C]
        AATCCCGCAGGCCCAGCTCACCACCCCAACTCAGCCCACTTCATGGGAAGCTGGTGGCAG
        TGGGGGTACGGGGGCAGATTGTCCCTTGGGTGAACTTCTTTGTCCAGTGCTCAAGTCCCC
        AGCCTGCCCCGCTCAGGCTTCACCCCAGTTTTATTTTTCTGCCAGGTCCAGGTGTGTTAG
        GGCCGCGTACCTTCCTTCCCGAGGCCCCACCGGGGCAGTTTCACTTTCTGTTCTACTAGG
        TTTCATTTCCTGCCCCCAGGCCCCCAAAGCTGAGGACCCAGACACCTGGGTCCTTTGAGC

2905    AAACTGAAGCTTAGAGAAAAACTTCCCAAGGGGTCAGGGCCAAGGCAGTCCTGGTCTTCT
        GTGGACTCTCTCTTAGCAGTGAGAACTGATAGGGTTTTGCCCACCAAATGCCTAAATCCC
        GCAGGCCCAGCTCACCACCCCAACTCAGCCCACTTCATGGGAAGCTGGTGGCAGTGGGGG
        TACGGGGGCAGATTGTCCCTTGGGTGAACTTCTTTGTCCAGTGCTCAAGTCCCCAGCCTG
        CCCCGCTCAGGCTTCACCCCAGTTTTATTTTTCTGCCAGGTCCAGGTGTGTTAGGGCCGC
        [G,T]
        TACCTTCCTTCCCGAGGCCCCACCGGGGCAGTTTCACTTTCTGTTCTACTAGGTTTCATT
        TCCTGCCCCCAGGCCCCCAAAGCTGAGGACCCAGACACCTGGGTCCTTTGAGCATTGGGT
        GGCAGGCGCCCTCCTTATCTCCAGCGCCCTCGAGTCCAAGTCCCCCGGCCCCCCCCCCCC
        ACTTTCCCAGGAGCCCCGAAAAGTCCTCCTTCCAGCTCGCCCCACCCCAGTGCTGGGCCT
        GGAGCCAGGTAACTGGGACAACAATAGACAGATCCAGGAAGGAAGCTGGGGGGCGGGTGT

4136    AGGCTGAGCTGGAGCTGGGGGGATCGCTTGAGCCCAGGAGTTCGAGATCAGCCTGGGCAA
        CATAGTGAGATTCCATCTCTACCCCTTTCTCTCCCTCTGAAAAAAAAAAAATAAGGAGAGT
        TGGGGGCTTCTGGAAGATGGTTACAGAGTGGGGTCATGAAGGCGCTCTTTAGGGACTGGT
        CTAAACTTTCATTTATGGATTAGGATGCTAGTGACACGCTTTGTACAGTTTGAAAATTCA
        TTGAGCTGTGCACTTGTGATGTGCGGCCTTTCCTGAACATATGTTATACTTATTTATTTA
        [T,C]
        AAAACTAGTCAAGTGCAGTAGTTAGAAGGGGGAAAAGAGGAGAAGAAGGAGTTGGATCTG
        TAACTGACTGTGTTATGCTTAAATATAAAGGTAAAAAATGGGCCAGCTGCAGTGGCTCAC
        ACCTGTAATCCCAGCAGTTTGGGAGGCTGAGGTGGGAGGATCGCTGGAGCCCAGGAGTTT
        GAGACCAGCCTGGGCAACATAAGGAGACCCCATCTCTTAAAAAAAAAAAAAAAAAAAAAA
        GTTAACCGGGCGAGGTGGCACACGTCTGTAGTCTCAGCTACTTGGGAGGCTGAGGTGGGA

4846    AAAAAGAAAAAAAAAAAGTTATGATGTCCATGGCTCCTGCCACGAAAATGCTAAATTAAAT
        CAGAATCTCTGCAAAGTGAGATGGAATCTGCACATCAGTATTTTTAAAAGCCCCCAGGTG
        ATTTTCTAAGACACAGCCAGAAGCCAGTTCATCCACTCACTATTCCAGTAGTATAGATGG
        GCATGCTCTCAGCACCTTAGAGCAGTCTATGGCCCTTGGTCCCTCTTGAGGGTGGGGGCA
        GCTGCCTTTTTCATGGCTGTCTTCCCTGCTGCTCCGGCATACTGCAGTGCCCAGTGAAAC
        [C,T]
        GGCTCAATGAATGAATGACAGAAGTCTGGATTTACACCTTTAGTGACCTTGTTCAGGCTT
        TAAGTACTCTTTCATATCATAAGCTGGCCTCACTTGAATTTTTATCTTCATTGTTGTCTC
        TCCCCTAAACCTGAGTTTTGTTTTGTTTTTGTCATTTTTATTATTTTTGTTTTTTTAGA
        CGGAGTCTCGCTCTGTCACCCAGGCTGGAGTGCAGTGGCGCAAACTCAGCTTGCTGCAAC
        CTCTGCCTCCTGGGTTCAAGCGATTCTCCTGCCTCAGCCTCCCGAGTAGCTGGGATTACA
```

FIGURE 3W

6409    ACTACTGTACTCCAGCCTGGGTGACAGAGTGAAACTCTCTAACAAACACAAACAAAAAAG
CCCACAACATTTTAAGCACTTTTAAGCGTACAGTTCAGTAATTTAAAGTTCACGCACACT
GTTGTGCAGCCGGTCTCCAGAACTGTTGTCATCTTGCGAAACTGAAGCTCCTTGCCCGTT
AAACAACTCCCCAATTCCCGCTCTGTCCCTGCCCAGGGCGTAGGGATATATGTGTTTTGT
TCAGGGGTGGAGCTGGGATTTGAACCCAGGCAGAATGTAGTATGAGAGCAAATGAAGGAA
[A,G]
GAAGGAAAGATCACACCTTGCGGCTGGGAGCACTGTGAGAAATCAGGGAACGTGGGGTCT
GGAAAAGCTTTGGCCTACCCCGCCTCAAGCATCCACCCCTATTTTCCGCCTACAGCCTCG
GCCACCTTCGAGGACTTCCAGATCCGCCCGCACGCCCTCACGGTGCACTCCTATCGGGCG
CCTGCCTTCTGTGATCACTGCGGGGAGATGCTCTTCGGCCTAGTGCGCCAGGGCCTCAAG
TGCGATGGTGAGAGCTAAAGGGTTGGGGGCGGGGCCTGGGGCGGGGCTCTGCACCGGGGG

8088    CTTTTTAAAACATTCAGCTGATTGAATGAGACCCACCTAGAACAAGCAGGATCACCTCTC
CCACTTACAGTCAGCTGATTATGGATTTTCATCACATCCAGAAAATACCTCCACTGGGCC
GGGTGCGGTGGCTCACGCCTGTAATCCCAGCACTCTGGGAGGCCGAGGCAGGTGAATCAC
CTGAGGTCAGGAGTTCGAGACCAGCCTGTCCAACATGGTGAAACCCCGTCTCTACTAAAA
ATACAAAAAAGCCGGCGTGTTGGTGGACGCCTGTAATTCCAGCTACTCGGGAGGCTCAGT
[C,T]
AGGAGAATCTCTTGAACCCGGGAGGCAGAGCTTGCAGTGAGCTGAGATTGCACCATTACA
CTCCAGCCTGGGCAACAAGAGCAAAACTCTGTCTCAAAAAAATGAAAAGAAAAGAAAATA
CCTCCATGGGGCCTTCTCTCCCCAGTTCTTCCTGGAGTCGGGGAAAAGCTGGGTTGAGAA
GGTGAAAAGAAAAAACAAACCTTGACTGGGCACAGTGGTTCACACCTGTAACCCCAGCAC
TTTGGAGGCTGAGGCAGGCGGATCATGAGGTCAAGAGATTGAGACCACCCTGGCCAACAT

8228    GTAATCCCAGCACTCTGGGAGGCCGAGGCAGGTGAATCACCTGAGGTCAGGAGTTCGAGA
CCAGCCTGTCCAACATGGTGAAACCCCGTCTCTACTAAAAATACAAAAAAGCCGGCGTGT
TGGTGGACGCCTGTAATTCCAGCTACTCGGGAGGCTCAGTCAGGAGAATCTCTTGAACCC
GGGAGGCAGAGCTTGCAGTGAGCTGAGATTGCACCATTACACTCCAGCCTGGGCAACAAG
AGCAAAACTCTGTCTCAAAAAAATGAAAAGAAAAGAAAATACCTCCATGGGGCCTTCTCT
[C,T]
CCCAGTTCTTCCTGGAGTCGGGGAAAAGCTGGGTTGAGAAGGTGAAAAGAAAAAACAAAC
CTTGACTGGGCACAGTGGTTCACACCTGTAACCCCAGCACTTTGGAGGCTGAGGCAGGCG
GATCATGAGGTCAAGAGATTGAGACCACCCTGGCCAACATGGTGAAACCCCATCTCTCCT
AAAAATACAAAAATTAGCGGGCGTGGTGGCATGTGCCTATAGTCCCAGCTACTTGGGAGG
CTGAGGTAGGAGAATCACTTGAACCCAGGAGACAGAGGTTGCAGTGAGCCGAGATCGTGC

8478    TGTCTCAAAAAAATGAAAAGAAAAGAAAATACCTCCATGGGGCCTTCTCTCCCCAGTTCT
TCCTGGAGTCGGGGAAAAGCTGGGTTGAGAAGGTGAAAAGAAAAAACAAACCTTGACTGG
GCACAGTGGTTCACACCTGTAACCCCAGCACTTTGGAGGCTGAGGCAGGCGGATCATGAG
GTCAAGAGATTGAGACCACCCTGGCCAACATGGTGAAACCCCATCTCTCCTAAAAATACA
AAAATTAGCGGGCGTGGTGGCATGTGCCTATAGTCCCAGCTACTTGGGAGGCTGAGGTAG
[G,A]
AGAATCACTTGAACCCAGGAGACAGAGGTTGCAGTGAGCCGAGATCGTGCCACTGCACTC
CAGCCTGGCAACAGAGCGAGACTCCGTCTCAAAAAAAAAAAACAAAAAAAAAAAACACA
AACAAACCAACCTTCATGGCAACATCTAGATTAGTGTCTGAATAACTGTGGATCTCGCCT

FIGURE 3X

```
              AGCCAAGCTGACACATTAACATGACTATCAGGGTCCATCTCTTGTCAACCTGGCACCTGT
              CTTAGTTTGTCAGGGCTGCCTTAACAAAATACCACCCTGCGTGGCTTAAATGACAGACAT

9831          ACCTCCACTTCCCAGGCTCAAGCGATTCTCCTGCCTCAGCCTACCGAGTAGCTGGGATTA
              CAGGCACACACCATTACTGCCCGGCTAATTTTTGTATTTCTAGTAGAGACGGGGTTTCAC
              CACGTTGGCCAGGCTGGTCTTGAACTCCTGACCTCAAATGATCCACCCGCCTTGCCCTCC
              CACAGTGCTGGGATTACAGGCATGAGCCACCGCGCCTGTCCAAAACATACAGTTCTTTAA
              GCCAAGATGTCTCAAGGTTCAGCCCAAGTGTCAAGATCTATATAGGTCCTCTGTCCCTGT
              [T,C]
              ATTCATGCTTCTGAGTGAGAATGTTGAAATCGGGGCTCTGCCTACAGATGAAGGCCATGT
              ACCTGCATTGGCTATGAGGACAGATGACAGGTGAGGACCATCCATTCTGTGATGAGACCC
              TGTGGCTCCATTTTTTTGTGTGTGTGAGACAGAGTCTTGCTCCGTCACCCAGGATGGAGT
              GCAGTGGCGTGGTCTTGGCTCACTGCAACCTCTACCTCCTGGGTTCAAGCAATTCTCCTG
              CTTCAGCCTCCCAAATAGCTGGGATTACAGGTGCGCACCACCACTCCTGGCTAATTTTTG

12341         GTGAGCCACCATGCGTGGCCCACACTACTAAGATTTAATCACACTACTTAGGGATTGCCT
              GGATTCCAGGTCTACAGAAAAGAGAAAGTGGGGTACAGGGGGTGAGCAGACCTGGAGGGA
              TAGTGACCTTAGGGGTGGGGGTGAGGAGAGGCATTTTCTTTTGGAAAGTTGGGGTTGGGG
              AAAGAGGGGGAACCAAAGGGGCCTCAGAAAAAGGAAGGTCAGGGTTAGAAGGGGGAACAG
              GTGTCTCTAGGGAGATGGACAGGAGTTTTGGGGAGGACTAGAAGGAGGTGCTTACCATAG
              [G,A]
              GGACTGGGGCTGGGTCAGAGCTTTGGCGGGGACTTTTGAGGCATCCATTGTTGCAGTGGG
              AAAAGGTGGGGTGTGAGGCGCGTTCAGGGCCTGGGGGGCAGATGGGGTGATGTCGGGGCT
              ACAAGCTGGAACTAGGGGTGGAGCTTTGGAGGGAACCTTTGAGGTATCCCTTGTTGGAGT
              GGGAAAATTTTGGGTGTGAGGCGTGTTCAGGGTCTGGGGGACAGATGGGGTGATGGCAGG
              GCTACAAGCTGAAACTGGGGACAGAGCTTTGGGGGGAGCCTTTGAGGTGACCCTTGTTGG

12631         CTTACCATAGAGGACTGGGGCTGGGTCAGAGCTTTGGCGGGGACTTTTGAGGCATCCATT
              GTTGCAGTGGGAAAAGGTGGGGTGTGAGGCGCGTTCAGGGCCTGGGGGGCAGATGGGGTG
              ATGTCGGGGCTACAAGCTGGAACTAGGGGTGGAGCTTTGGAGGGAACCTTTGAGGTATCC
              CTTGTTGGAGTGGGAAAATTTTGGGTGTGAGGCGTGTTCAGGGTCTGGGGGACAGATGGG
              GTGATGGCAGGGCTACAAGCTGAAACTGGGGACAGAGCTTTGGGGGGAGCCTTTGAGGTG
              [A,T]
              CCCTTGTTGGAGTGAGAAAAGGGGTGTGGGTGTGTTCAGGGTCTGGGGGACAGATGGGGT
              GATGGTGGGGCTACAAGCTGGAACTTGGGGCAGAACTCTAAGGAGGGGTGGGCCTGAAGG
              GGCTGATACACTTACGGATAGTAGTGCCTTTTGGAGGAGATCGTGCTGGCGGGGGGTGAT
              GGGACAGGACCAGGTGAGAGATTGGGTGGAAAGGGCACAACTTCTCAAGAAGAGACCTAG
              GAGGGGCAGACGCCATGTCTCTTACTCTCTGGCGCCCCCTGCAGGCTGCGGGCTGAACTA

13168         CTAGGAGGGGCAGACGCCATGTCTCTTACTCTCTGGCGCCCCCTGCAGGCTGCGGGCTGA
              ACTACCACAAGCGCTGTGCCTTCAGCATCCCCAACAACTGTAGTGGGCCCGCAAACGGC
              GCCTGTCATCCACGTCTCTGGCCAGTGGCCACTCGGTGCGCCTCGGCACCTCCGAGTCCC
              TGCCCTGCACGGCTGAAGAGCTGGTGAGGAGATGGGGGATGGGACGGGTTGGTGGCTAGG
              GGGGTGACTTGGCCCAGGCATGGGGCCAACGCACTGATGTGTCCCCTCCATTCTTGCCAA
              [T,C]
              GACAGAGCCGTAGCACCACCGAACTCCTGCCTCGCCGTCCCCCGTCATCCTCTTCCTCCT
```

FIGURE 3Y

```
         CTTCTGCCTCATCGTATACGGGCCGCCCCATTGAGCTGGACAAGATGCTGCTCTCCAAGG
         TCAAGGTGCCGCACACCTTCCTCATCCACAGCTATACACGGCCCACCGTTTGCCAGGCTT
         GCAAGAAACTCCTCAAGGGCCTCTTCCGGCAGGGCCTGCAATGCAAAGGTTAGCTGGGCC
         TGTCGGGGAGGACAGTACAGGGTCAGAACCTCCTTCCCGCCCCAACCTGGTCTTGTGGCA

13572    GATGCTGCTCTCCAAGGTCAAGGTGCCGCACACCTTCCTCATCCACAGCTATACACGGCC
         CACCGTTTGCCAGGCTTGCAAGAAACTCCTCAAGGGCCTCTTCCGGCAGGGCCTGCAATG
         CAAAGGTTAGCTGGGCCTGTCGGGGAGGACAGTACAGGGTCAGAACCTCCTTCCCGCCCC
         AACCTGGTCTTGTGGCAGGACACAAGGATCTGAGCCTTGGGACCCCAGGGCCTCAGAAGG
         GGAGGGCCCTGAATCCTAGTGTTCTGGGACCTTTGGAATTCTGGAATCTTAGAACCTCAG
         [-,G,T]
         TGTGTGTGTGTGTGTGTGTGTGTGTGTGTGTGTTGTGTTGTTTTTGAAGACAGGGTG
         TCACTCTATCACCCAGGCTGGAGTGCAGTGGCGCAATCACGGCTCACTGCAGCTTCAACC
         TCTTGGGTTCAAGTGATCCTCCTGCCTCAGCCTCCCAAGTAGCTAGGACTACAGGTGGTG
         CCACCACACCCAGCTAATTTTCTTTTCTTTTTTTTTTTTGAGACGGAGTCTCACTCTG
         TCGCCCAGGCTGGAGTGCAGTGGTGTGATCTCGGGCTCACTGCAAACTCTGCCTCCTGGG

14789    CTAGAATCATATAAGCTTGAAACCATCGTAACCTAGAATCCTGGAAATTCTAGACTCCCA
         GAACTTTGAACAATCAAATTCTAGAATCCAGCCAGGTGTGGTGGCTCATGCATGTAATCT
         CAGCACTTTGGGAGGCCAAGGTAGGTGGATCACTTGAGCCTAGGAGTTTAAGACCAGCCT
         GGGCAACATGGTGAAACCCTGTCTCTACAAAAAAAATTAAAAATTAGCCAGGCATGGCAG
         CATGCATCTGTGGTTCCAGCTACTTGGGACTCTGAGGAGGGAGGATTGCTTGAGCCCAGG
         [A,G]
         GGTTGAGGCTGCAGTGAGCCATGATTGTGCCACTGCATTCCAGCCTGGGTGACAGAGCAA
         GAACTTGTCTCAAAAAAAGAAAAAAAAAAAATTCTAGAACCTCAGAAGCCTAGATCCACAT
         AAACTTAGAAACATCCAATTCAAGAATTTACTGGAACAATCAAATTCTAGAATCTTAGAA
         GCCTAGAGCTAAAGAAGCATAGAAACATCAAATTCTAGAATCTTGTATGTATAGAATCCT
         AGAACCTTGGAATCTGCAGATTCTGGAGGTAGAGAAGCCTAGAATTGTAGAACCCTAGAA

15528    GTAGTGCGTGCCTGTAGTTTCAGCTACTCAGGAGGCTGAGGTGGGAAGATCGCTTGAGCC
         TGGGAGGCAGAGGTTGCAGTGAGCCGAGATGGTGCCATTGCACACTCTAGTCTGGGTGAC
         AGCCAGACTGTTTCTTAAAAAAAAAAAAAAAAAAA
         [A,C]
         AAAAACCAGAATCATAGAACCTTCATAAAATAGGTTTTTAGTAAACTCTAGAATCTTCGA
         TGTATAGTGTCCCTAGAACCGTGGAAACACTGAACTCTACAGCAATGGTTCTCGACCAGG
         GGCCGTTTTGCTCCTAGGGGATGTTTGGCAAGGGTTGGAGATGGTTTTGTTTGGTACGCT
         GGGATAGTGCTACTGGCATCCAGTAGGTAGAAGTCAGAGATGCAGCTAAACATCCTACAA
         TACACAGAGCAAGTGCCCTAAAACAAGGAATTATCCTGGGCACTGTGTTAGTGTCACGGG

17865    GGCCTCCCAAAGTGCTGGGATTACAGGCATGAGCCACCGCGCCTGACCTATATTCCTCTT
         CTTTTTTTTTTTTTTTTTTTTTTTAAGATAGGGGGTCTTGCTATGTTGCCCAGGGTGGTCT
         TGAACTTCTGCGCTCAAGCAATCCTCCCACCTCAGCCTCCCAAAGTTCTGGGATTACAGG
         TGTGTGCCACTGTGCCCCCAGCCTACACATTTTTTAAACTATACACGGAGTTCATACTTAG
         TCAGCTCCACTGGAATGTGAGCTCAGGTGCATGAGGGCAAGGATATTTTCTGCCCTCCCA
         [C,T,G]
         GTGCCTAGGACAGGACTGGCTCAGATCAGGCACTTCCTATCTGGGTGTGGCGTGAATGTT
```

FIGURE 3Z

```
         TATTGAGAAAGCACAGTTCACACAGGCGCTGGAGGGTGACAGCCCAGATCCCAGCTCTAC
         CACTTCACTTGCTAGGCGCTTCCCTGTGTGCCACGGTTTCCTCCTGGGGCGATGAGGTAC
         CTACCCCACGGGGTGATAAACCTGGGGTAGGGGTAAGGGGGCACCCTCACAGGTGCACTG
         GAAAATATTTAATGAGCACCTGCTGTGTTCAAGCACACAGCTATGAACAAAAGAGGTAAA

17865    GGCCTCCCAAAGTGCTGGGATTACAGGCATGAGCCACCGCGCCTGACCTATATTCCTCTT
         CTTTTTTTTTTTTTTTTTTTTTTAAGATAGGGGGTCTTGCTATGTTGCCCAGGGTGGTCT
         TGAACTTCTGCGCTCAAGCAATCCTCCCACCTCAGCCTCCCAAAGTTCTGGGATTACAGG
         TGTGTGCCACTGTGCCCCCAGCCTACACATTTTTAAACTATACACGGAGTTCATACTTAG
         TCAGCTCCACTGGAATGTGAGCTCAGGTGCATGAGGGCAAGGATATTTTCTGCCCTCCCA
         [C,T,G]
         GTGCCTAGGACAGGACTGGCTCAGATCAGGCACTTCCTATCTGGGTGTGGCGTGAATGTT
         TATTGAGAAAGCACAGTTCACACAGGCGCTGGAGGGTGACAGCCCAGATCCCAGCTCTAC
         CACTTCACTTGCTAGGCGCTTCCCTGTGTGCCACGGTTTCCTCCTGGGGCGATGAGGTAC
         CTACCCCACGGGGTGATAAACCTGGGGTAGGGGTAAGGGGGCACCCTCACAGGTGCACTG
         GAAAATATTTAATGAGCACCTGCTGTGTTCAAGCACACAGCTATGAACAAAAGAGGTAAA

19005    GTCTCAGGCAAAGAGATGTGATCAAGGCCACCCAGGTTCTGATCTAGCACAGGGATCCAG
         AGATTGTTGGTTCCAGAGTTGAGCAAGTCACTTAATCTCTCAAATCTCAAACTCCTGACC
         TCAAGTGATCCCCCCACTTCTGCCTCCCAAAGTGTTGGGATTACAGGCATGAGCCACCAT
         GCCCAGCAGGCCACTTAATCTCTGTAGACCTTCCTTACTGTACTAACAGCATCTGCACAA
         ATGAGGGAGGTGAGGCCCAGAGAGGTTGAATCACTTACCCAGTGTCACACAGCTGGCTCC
         [A,G]
         CAATTGCTGGACTAAATACCAATTAGCACTTACTGGAGGTCCTCTGTATGCCAGGCACTG
         TACTAAGCTCCGTAGAAAGGTTTCCATTCCTCATAGCATCCCCTTTGGGTGGACAAACTG
         AGGCATGAAGAGGTTAGGTAATTTGCTAGGCAGCCTGACTTCAGAAAGGCCTACTACAGA
         AGCCCTCTCAAGAATCTCCTTCTGGGCCAGCGTGGTGGCTCACACCTGTAAGCACTCTGG
         GAGGCCGAGGCGGATGGATCTCGTGAACGGATTCTAAGGGTGGGACTAGGGGCAGGAGTT

19273    AATCACTTACCCAGTGTCACACAGCTGGCTCCACAATTGCTGGACTAAATACCAATTAGC
         ACTTACTGGAGGTCCTCTGTATGCCAGGCACTGTACTAAGCTCCGTAGAAAGGTTTCCAT
         TCCTCATAGCATCCCCTTTGGGTGGACAAACTGAGGCATGAAGAGGTTAGGTAATTTGCT
         AGGCAGCCTGACTTCAGAAAGGCCTACTACAGAAGCCCTCTCAAGAATCTCCTTCTGGGC
         CAGCGTGGTGGCTCACACCTGTAAGCACTCTGGGAGGCCGAGGCGGATGGATCTCGTGAA
         [C,G]
         GGATTCTAAGGGTGGGACTAGGGGCAGGAGTTAGGGAAGGAGTTGAGGCAAAGAGTTCGA
         GACCAGCCTGGCCAACATGGTGAAACCTCATCACTACTAAAAATACAAAAATTAGCCAGG
         GGTGGTGGCGTGCACCTAATGGTCACCGTGATTGTCCCGGCCACTCAGGAGGCTGAGGCA
         CGAGAATCGCTTGAACCCGGGAGGCAGAGGTTGCAGTGAGCCGAGATCGCACCACTGCAT
         TCCAGCCTGGGTGACAGAGCGAGCCTCTTAAAAACAAACAAAAGCAACTCCCGGGTGTG

24406    CTCCAAAACAGAAAAAACAACAACAACAAAAATCCACAACAAATCTCTGTTAAGCTCCTG
         GCCTGATATGTGGCCCTGGGCATATCACTTCCCCTCCATGAGCCTTGTCCCAGGTGCTGA
         TAAGTCCTCATGCACTTACTGAGTGCCTCCTCTGTGCGGGACAGTGCTGGGACCCAGTG
         GTGGCCAGGACAGCCCAAGACCTGCCCTCATGGGGCTCAGAGTCCAGTAGGGCAGAATAC
         CCATCTTCAGAGAGTGACAGTCCAGGGTGGGCAGGGTTGGGACAAGGAAGCTAGGGAGCT
```

FIGURE 3AA

[A,T,C,G]
GAGGAGCCCAGAGGGGTACCTGACCCAATCTGGGTATATAGGGGGGCTTCCTGGAGGAGG
TGACATCTGAACTGAGATCTGGAGGCCGAGGCAGGGTGAGATGTGGGAAAGAAAATGGGA
GGTCATTTTAGGCAGAGGCAAAAAATGTTGAGAGAGTACCAGGTTCCCACCCTCTGGAGC
TTATAATCCAGTGTGGGTGACAGACATTGATCATTAACCCATACAAGCAACGAGTGTGAT
GCAGAGCATTTGCGAGAGTAATCCAACTTGGTCCTAGGAGTGACATTTGAGCTTACACTT

24751 GGCTTCCTGGAGGAGGTGACATCTGAACTGAGATCTGGAGGCCGAGGCAGGGTGAGATGT
GGGAAAGAAAATGGGAGGTCATTTTAGGCAGAGGCAAAAAATGTTGAGAGAGTACCAGGT
TCCCACCCTCTGGAGCTTATAATCCAGTGTGGGTGACAGACATTGATCATTAACCCATAC
AAGCAACGAGTGTGATGCAGAGCATTTGCGAGAGTAATCCAACTTGGTCCTAGGAGTGAC
ATTTGAGCTTACACTTGAGGATGAGGAGGATTTAGCTAAGTCTAGGATGAAGGAAAGAGT
[C,T,A]
TTCCTGGCAGGGGAAACAGCATATGCAGAGACCAGAAGGCAGAAGAGAGTTTGCTGTATT
TGAGGCCGAGCAAGGAGGCCAGTGTGTCAGGAATAGCATGTTGGGGGTAGAAGTCAGAGG
TAGATGAGGGTCTAGGCCATGGCTTTTAGGCCATTTAAGGGGCTCAGGCTTCTTCCTGAG
GGCACTGGGGAGCCATGGCAGAGTTGTGAGCAGAGGAGGGACAGGGTCAGTCTTGTGCCT
CAGTAAGATCCCTCTGGTTTCTCTGTGGGAGGTGAGTAGGAAGGGGCAGGATTGGGGCAA

26208 TTCTTTCTGGCTCCAACCCTTCCTTTCTGATTGGTCACATGCTCACCTCCCATGTTGATT
GGCTTAGCTAGATCCTGGGTGGACTGATTGCAGGTTCTCCTTTTCTCATTGGGAAAAACC
AATGGACATTCCTCCTGTTATTAATAGGAAGGGTAAATTCGGCACTCTGATTGGTCACAG
AGGTAGATTTTGATTGGATAGGGAAGGTAGATTCTGCACTCTGATTGACCACAGAGCTAG
AACCTAGATTCTGATTGGATAGAGTAGATTCTGCATTCATATTGGCCACAGAACTAGTTC
[C,G]
TAGATTCTGATTGGAAAAGAGGGTAGATTCTGCACTCTGGCCACAGAGCTAGATCCTAGA
TTCTGATTGAATAGGAGGGTAGATTCTGCATTCTGATTGGCCACAGGTCTAGATCCTAGA
TTCTGATTGGATTGGAGGGTAGATTCTGCATTCTGATTGGCCACAGGCTAAATCCTAGAT
TCTGATTGTATGGGGCGGGTGGTAAATTTTACACTTTGATTTGCCACAGAGCTAGATCCT
AGAGTTCAATAGGACAGGGAGGGTAACTTCTACACTCTAAACTCTAAGACTCAGTTTCCT

26522 GAAAAGAGGGTAGATTCTGCACTCTGGCCACAGAGCTAGATCCTAGATTCTGATTGAATA
GGAGGGTAGATTCTGCATTCTGATTGGCCACAGGTCTAGATCCTAGATTCTGATTGGATT
GGAGGGTAGATTCTGCATTCTGATTGGCCACAGGCTAAATCCTAGATTCTGATTGTATGG
GGCGGGTGGTAAATTTTACACTTTGATTTGCCACAGAGCTAGATCCTAGAGTTCAATAGG
ACAGGGAGGGTAACTTCTACACTCTAAACTCTAAGACTCAGTTTCCTTCTCTGTATAATA
[G,A,C,T]
GGTCAGTCTGCCTCCCCTGGTGCTGGTGTCTCTCCCCTGTCCCCAGGACTCTTATGGGTC
ACACAAAACTAGATGCTAGATTCCGACTGGTTATAAATCCAGTTTCCCATGTTATACATT
CCCTTCTTCGGAGCTTTTTGTTTGTTTTTTGCTTTCCTTCTTTCTGCCTTTACTCCCAAG
GTGCACCTCAGGTGGCCTTTTCACGTATCTCCTGGGGCCTTCCAACTCTGCCCAACTCTG
GCTGTCTCCATGGTGGGGGGCAGAGGTTGGCAGAGGTGGAGATACTCCTGCCAGGACTGG

26577 GAATAGGAGGGTAGATTCTGCATTCTGATTGGCCACAGGTCTAGATCCTAGATTCTGATT
GGATTGGAGGGTAGATTCTGCATTCTGATTGGCCACAGGCTAAATCCTAGATTCTGATTG
TATGGGGCGGGTGGTAAATTTTACACTTTGATTTGCCACAGAGCTAGATCCTAGAGTTCA

FIGURE 3BB

```
         ATAGGACAGGGAGGGTAACTTCTACACTCTAAACTCTAAGACTCAGTTTCCTTCTCTGTA
         TAATAGGGTCAGTCTGCCTCCCCTGGTGCTGGTGTCTCTCCCCTGTCCCCAGGACTCTTA
         [T,A,G,C]
         GGGTCACACAAAACTAGATGCTAGATTCCGACTGGTTATAAATCCAGTTTCCCATGTTAT
         ACATTCCCTTCTTCGGAGCTTTTTGTTTGTTTTTTGCTTTCCTTCTTTCTGCCTTTACTC
         CCAAGGTGCACCTCAGGTGGCCTTTTCACGTATCTCCTGGGGCCTTCCAACTCTGCCCAA
         CTCTGGCTGTCTCCATGGTGGGGGGCAGAGGTTGGCAGAGGTGGAGATACTCCTGCCAGG
         ACTGGGTGGTCTTGCTCTCTCATCCCCCATCTCTTCTACTCCCTGTGCAGGAAAACACCG

26981    TCTTTCTGCCTTTACTCCCAAGGTGCACCTCAGGTGGCCTTTTCACGTATCTCCTGGGGC
         CTTCCAACTCTGCCCAACTCTGGCTGTCTCCATGGTGGGGGGCAGAGGTTGGCAGAGGTG
         GAGATACTCCTGCCAGGACTGGGTGGTCTTGCTCTCTCATCCCCCATCTCTTCTACTCCC
         TGTGCAGGAAAACACCGGAAGACAGGCCGGGACGTGGCAGTTAAGGTCATTGACAAACTG
         CGCTTCCCTACCAAGCAGGAGAGCCAGCTCCGGAATGAAGTGGCCATTCTGCAGGTAACC
         [T,C,A,G]
         CCAGGCCGCCTTCCCTTTCTGCTTCTTCCTTTCATGGGCCAGCTGACCCAGTGTAGGGGT
         GGTCAGGGAAGGCTTCCTGGGGGAGGGCATGTGCATGTTGAGACTGAAGGGGAGAAGGTG
         TTCTTAGCAGAGGGACCAGCCTGTACAAAGACCTGGTGAGAGGGAGCATGAGGTTTTCTA
         GAAAGGAGGTACTGGGAGATGAGGCCAGGGAGGAGGGCGGAGCCAGACCCTTTGGACTTT
         CTCCTGAGGGTACTGGAGAGCCACAGAAGGCTTTTGAGCAAGGGAGGGGCAGGATCAGGT

28409    AGGGGGTCAAGCAGACACTTGGGGGAGTCACAATAGCAGATAACAGAAACCATCATCAGG
         CTGGGCGCAGTGGCTCACACCCGTAATCCCAGCACTTTGGGAGGCCCACGAGGTCAGGAG
         ATCGAAACCATCCTGGCTAACATGGTGAAACCCTGTCTCTACTAGAAATACAAAAAATTA
         GCCGGGCATGGTGGCAGGCGCCTGTAGTCCCAGCTACTCGGGAGGCTGAGGCAGGAGAAT
         GGTGTGAACCTGGGAGATGGAGCTTGCAGTGAGCCGAGATCGCGCCACTGCACTCCAGCC
         [C,G,A,T]
         GGGCGACAGAGCAAGACTCCATCTCAAGAAAAAAAAAAAAAAAAAAAAAGGAACCATAATC
         GTACAGAAGTAATAATAACCATAATAGAAAAAATAAGCCGGGCATGGTAGCACGTGTCTG
         TGGTCTCAGCTACTCAGGAGGCTGAGGCAGGAGGATCACTTGATCCCAGGAGTTCTGTGC
         TGATCAGGTGTCCTCATTAAGTTTGGCATCCATGTGGTGACCTCCCAGGAGTGGGGGACC
         ACCAGGTTGCAAAGCAGCCCAGGTTGGAAATGGAGCAGGTCAAAGCTCTCTTACTGATCA

29179    GGAGGCCAAGGCGGGTGGATCACCTGAGGTCAGGAGTTTGAGACCAGCCTGGCCAACATG
         GTGAAACCCTGTCTCTACTAAAAATACAAAAATTAGCTGAGCATGGTGGCAGGCACCTGT
         AATCATAGCTACTTGGGAGGCTGAGGCAGGAGAATCCCTTGAGCCCAGGAGGCAGAGGTT
         ACAGTGAGCTGAGATCGTGCCATTGTACTCCAGCCTGGGGGACAAGAGTGAAACTTCGTC
         TCAAAAAAAAAAAAAAATAATAATAATAATAATAAAGAGTAATCATAATAATAGAAAAAAA
         [A,T]
         AGACTAGCGGTAATGATAGCTATTTTTATTTATAAAAAATAAATGATCAGTCAGGCTCCCT
         GGACCTGACTTGACTCATCTAGAAAAAAGGGGAGTCAGGCATGGTGGGTACACCTGTAA
         TCCCAGCTACTCAGGAAGCTAAGGCCAGAGGATTGCTTAAGCCCAGGAGTTTGAGCCAGC
         CTGGGCAACATAGCAAGAGCCCATCTCAAAAACAGGCTGGCTCATGCCCGTAATCCCAGC
         GCTTTGGGAGGCCAAGGCAAGAGGATCGCTTGAAGCCAGGAGTTGGAGACCAGCCTAGGC

30276    TAACCTGTGCAGTAGGTGCTATTATTATCAATCCCCTTTTATGGTTGAAGAAACTGAGGG
```

FIGURE 3CC

TCAGAGACATCAAATATCTTGTCCAGGGTCACATAGCTGGTGGGATTTGAACCTAGGATC
TTTGCTTTTAACTAGTGATGTCAAACTCATTTGTGTTACATTCAAACAGATTTTCCTTGT
GTGCCTGTGTGCCTGTGCTTTTTGTTTGTTTTTTGAGACAGGGTCTCGCTCTGTCACCC
GAGCTGGAGTGCAGTGGTACAATCATGGCTCACTGCAGCCTTGACCTCCCGGGTTCAAGC
[A,G]
ATTCTCCTGCCTCAGCCTCCTGAGTAGCTGAGACAACAGGCATCAGCCATCACACCCAGC
TAATTTTTATAAAGACATTTTTATAAAGACTTGCTATGTTGCCCAGGCTGGTCTTCAACT
CCTGGGCTCAAGTGATCCTCCTGACTCGGCCTCAGCCTCGCAAAGTTCTGGGATTACAGG
TGTGAGCCACTGTGCCCGGCCTCTGTTCTGCGTTTCTTTTTTTTTGGTGGAGGTGCACAT
TAGATTCTTATCACTTATATTGTTCAATGGTTTTATCCCAGTGTTTGCCTCTTTATTTTA

30320    TTGAAGAAACTGAGGGTCAGAGACATCAAATATCTTGTCCAGGGTCACATAGCTGGTGGG
ATTTGAACCTAGGATCTTTGCTTTTAACTAGTGATGTCAAACTCATTTGTGTTACATTCA
AACAGATTTTCCTTGTGTGCCTGTGTGCCTGTGCTTTTTGTTTGTTTTTTGAGACAGGG
TCTCGCTCTGTCACCCGAGCTGGAGTGCAGTGGTACAATCATGGCTCACTGCAGCCTTGA
CCTCCCGGGTTCAAGCAATTCTCCTGCCTCAGCCTCCTGAGTAGCTGAGACAACAGGCAT
[C,T]
AGCCATCACACCCAGCTAATTTTTATAAAGACATTTTTATAAAGACTTGCTATGTTGCCC
AGGCTGGTCTTCAACTCCTGGGCTCAAGTGATCCTCCTGACTCGGCCTCAGCCTCGCAAA
GTTCTGGGATTACAGGTGTGAGCCACTGTGCCCGGCCTCTGTTCTGCGTTTCTTTTTTTT
TGGTGGAGGTGCACATTAGATTCTTATCACTTATATTGTTCAATGGTTTTATCCCAGTGT
TTGCCTCTTTATTTTATATTTAGTTTTTATTTACCATAGGGTTTTATTTATTTTATTTTT

30502    TCGCTCTGTCACCCGAGCTGGAGTGCAGTGGTACAATCATGGCTCACTGCAGCCTTGACC
TCCCGGGTTCAAGCAATTCTCCTGCCTCAGCCTCCTGAGTAGCTGAGACAACAGGCATCA
GCCATCACACCCAGCTAATTTTTATAAAGACATTTTTATAAAGACTTGCTATGTTGCCCA
GGCTGGTCTTCAACTCCTGGGCTCAAGTGATCCTCCTGACTCGGCCTCAGCCTCGCAAAG
TTCTGGGATTACAGGTGTGAGCCACTGTGCCCGGCCTCTGTTCTGCGTTTCTTTTTTTTT
[G,A]
GTGGAGGTGCACATTAGATTCTTATCACTTATATTGTTCAATGGTTTTATCCCAGTGTTT
GCCTCTTTATTTTATATTTAGTTTTTATTTACCATAGGGTTTTATTTATTTTATTTTTTA
TTTTTTTTTGAGACGGAGTCTTGCTCTATTGCCCAGGCTGGAGTGCAGTGGCACCATCTC
GGCTCACTGCAAGCTCCGCCTCCCAGGTTCACACCATTCTCCTACCTCAGCCTCCCAAGT
AGCTGGGACTACAGGTGCCCACCACCACGCCCGGCTAATTTTTTGTATTTTCAGTAGAGA

31348    GAACCACAGGCATGAGCCACCACGTCCAGCTAATTTTTTTTTTTTTTTTTTTAATGTTT
TTGTAGAGACAAGGTCTCGCCATGTTGCCCAGGCTGGTCTTGAACTCCTGGGCTCGAGCG
ATCCTCCCATCTCAGTCTCCTGAGTTAGCTGGAACCACAGGCATGAGCCATTACACCTGG
CTAATTTTTTTTTATGTTTTTGTAGAGACAGGGTCTTGCCATGTTGGGTCTCGAACTCCT
GGGCTTAAGTGGTCCTCTTGCTGCAGCCTCCCAAAGTTCTGGGTTACAGGCATGAGCCAC
[-,T]
GCGTCCAGCCGGCCATAGAGTGGAACTTTTACGATGTTAAATATCCCCTTGTGTGGTTTC
TGTGTTTCACATCCTTCCTAGAAAGGCTTCCTTCTGGTGGGTGCCTTGCCTTCTTCTGAG
ACATCTCTGTGGGTCTCAGAGCCATCGTTGCTGTGTTCCCTTTACCCTGGCCCAGCACCC
TTATCCTCTCAGGCAGTGTGCCTGTGTTTGTCAGGCTGGCTTATGGGGTGGGGACAGAAA
CCCACTGATGCACCCTCATCCAGACTTTATTATTTATGTATTTTTGAGACAGAGTCTCGC

FIGURE 3DD

33403  GGTGTGGTGGCATTCACCTGTAATCCCAGCTACTGGGGAGGCTGAGGCACAAGAATTGCT
TGAACCTGGGAGGTGGAATTTGTGGTGAGTCGAGGTCATGCCGTTGCACTCCAGCGTGGG
CAACAGAGTGAGACTCCATCTCAAAAAAACAATCTGGAGATGACATATACAACACATGCA
TCTTTCCAGCTTGGTCTCCCAGTCTGTAGAATGAGGAGGTTGGTCAGGCATGGTGGGTCG
TGCCTATTATCTCAAGGTTTGGGTAGCTGAGGTGGGAAGATCATTTGAGGCCAGGAGTTT
[A,T]
AGACCAGCCTGGGCAACATAGCGAGATGCCATCTCTACAAAAAGATTTTTTTAAAAAAGA
AAACAATCAGAATAAACACAAGTATTTAAACTCTGAGACAGATACACAAGTATTTAAACT
CCGAGACAGATAATAATTGCAGTTGTACAACACTCTATGCTTCTGGTGTACTTGGCATTT
TGAGTTACAGAGAATCAAGAAATATGATTCTCACAGATGAATGGTTACAAATGGTAATTT
TTTTTTTAATCAGCTCACCTTATCATAGGAACAGATACAGCAGGAGAAGCTTTATTTAAG

33554  ATCTGGAGATGACATATACAACACATGCATCTTTCCAGCTTGGTCTCCCAGTCTGTAGAA
TGAGGAGGTTGGTCAGGCATGGTGGGTCGTGCCTATTATCTCAAGGTTTGGGTAGCTGAG
GTGGGAAGATCATTTGAGGCCAGGAGTTTTAGACCAGCCTGGGCAACATAGCGAGATGCC
ATCTCTACAAAAAGATTTTTTTAAAAAAGAAAACAATCAGAATAAACACAAGTATTTAAA
CTCTGAGACAGATACACAAGTATTTAAACTCCGAGACAGATAATAATTGCAGTTGTACAA
[C,-]
ACTCTATGCTTCTGGTGTACTTGGCATTTTGAGTTACAGAGAATCAAGAAATATGATTCT
CACAGATGAATGGTTACAAATGGTAATTTTTTTTTTTAATCAGCTCACCTTATCATAGGAA
CAGATACAGCAGGAGAAGCTTTATTTAAGAGACACAAACAAATATATTTACCAACAAGCC
ATCACAAAAATAATAACTAATAACAACAACAGTAACAGCTAACATACAGTGGTTAGCTAT
CCTAAGCGTTTTACATGCATCTTTAGATATGCTTTAAACCTTATAGCAACCTGTAAGGTT

33558  GGAGATGACATATACAACACATGCATCTTTCCAGCTTGGTCTCCCAGTCTGTAGAATGAG
GAGGTTGGTCAGGCATGGTGGGTCGTGCCTATTATCTCAAGGTTTGGGTAGCTGAGGTGG
GAAGATCATTTGAGGCCAGGAGTTTTAGACCAGCCTGGGCAACATAGCGAGATGCCATCT
CTACAAAAAGATTTTTTTAAAAAAGAAAACAATCAGAATAAACACAAGTATTTAAACTCT
GAGACAGATACACAAGTATTTAAACTCCGAGACAGATAATAATTGCAGTTGTACAACACT
[C,-]
TATGCTTCTGGTGTACTTGGCATTTTGAGTTACAGAGAATCAAGAAATATGATTCTCACA
GATGAATGGTTACAAATGGTAATTTTTTTTTTAATCAGCTCACCTTATCATAGGAACAGA
TACAGCAGGAGAAGCTTTATTTAAGAGACACAAACAAATATATTTACCAACAAGCCATCA
CAAAAATAATAACTAATAACAACAACAGTAACAGCTAACATACAGTGGTTAGCTATCCTA
AGCGTTTTACATGCATCTTTAGATATGCTTTAAACCTTATAGCAACCTGTAAGGTTGGTA

34192  CGCCCAGGCTGGAAGTGCAATGGCGCGATGTCGACTCACTGCAACCTCCACCTCTCCAGT
TCAAGCGATTTTCCTGCCTCAGCCTCCCGAGTAGCTGGGACTACAGGCGCCCACCACCAC
GCCTAATTTTTGTATTTTTAATAGAGGCAGGGTTTTGCTATGTTGGCCAGGATGGTGTCT
AACTCCTGACCTCAGGTGATCCACCTGCCTCAGCCTTCCAAAGTGCTGAGATTACAGGCA
TGAGTCACCATGCCCAGCCAAAGTTTTTTGTAAGGATGAAAAATATTTTTTTTAAAAATG
[G,A]
AATCAGGCTGGGCACAGTGGCTCACGCCTATAATCCCAGCACTTTGGGAGGCCAAGGTTG
GTGGATCACGAGGTCAGGAGTTCAAGACCAGCCTGACCAACATGATGAAACCCCGTCTCT
ACTAAAAATACAAAAATTAGCCGGGCATGGTGGTGTGTGCCTGTAATCCCAGCTGCTCAG

FIGURE 3EE

```
        GAGGCTGAGGCAGGAGAATCAGGAGGCCTTCTCAAAAAAAAAAAAAAAAAAGGAATCAAAG
        CCCGACATGGTGGTGGTGGCACATGCCTGTAGTCCTAGCTATTTGGGAGACTGAGGCTGG

37005   CATAAAAATTATTAAGGCCAGGGGAGGTGGCTCATGCCTATAATCCCCGCACTTTGGGAG
        GCCAAGATGGGAAGACGGCTTGAGACCAGGAGTTCAAGTCTGAAGTGAGCTATGATTGTG
        CCACTGCACTCCAGCTGGGGTGACAGAGCAAGACCCTGTCTCTTAAAAAAGAAACAAAAC
        TCAATGAAACATTCTGCTTGTTTTTCATACTATGTCTTCAAAATCTGGTGTGTATAACAG
        TTGGGGAAATAGATTGACATGCCCAAGTTGTTCCAAACATATTTAAAAGTTTTCTGGTTG
        [A,G]
        GCGCAGCGGCTCATGCCTATAATCCCAGCACTTTGGGAGGCTGAGGCGGGCAGATCACTT
        GAGGTCTGGAGTTGGATACCAGTCTGGCTAACATGGCGAAACCCCGTCTCTACTAAAAAT
        ACAAAAATTAGCTGGGCATGGTGGCGGGAACCTGTAATCCCAGGTTCTCAGGAGGCTGAA
        GCAGGAGAATTGCTTGAACCCAGGAGGGTGGAGGTTGCGGTGAGCCGAGATCACACCACT
        GCACTCCAGCCTGGACGACAGACCAAGACTCGTCTCAAAAAAATAATAATAAAATAAAAA

37429   AAAATTAGCTGGGCATGGTGGCGGGAACCTGTAATCCCAGGTTCTCAGGAGGCTGAAGCA
        GGAGAATTGCTTGAACCCAGGAGGGTGGAGGTTGCGGTGAGCCGAGATCACACCACTGCA
        CTCCAGCCTGGACGACAGACCAAGACTCGTCTCAAAAAAATAATAATAAAATAAAAATTT
        TAAAAAAGATCCATAGGAAAGTATAGATCTTGGAAAAGAGAAAGAGCTATAAGATCTGTA
        GAAAGGGCAGAGTACCTCAGGAAAGGGTGGCTGTCACATTGAGATTCAGGTCAGGGGTTG
        [A,G]
        GGCGTGGCTGGTTTCAAAGGTGACAGAGGCTTCAGGCTTCAAGGATTTGGGGCTCTATCC
        TGCAAGCAACAGTGAGCCAAGGAAGGGTTTTGAACAGGGAAAGGACAGTACATGAACAGA
        GCTGGGAACCAAGGCTGAGAGGTAGGCAGCAGAGCAAGACCTTGAACCCAGGTCTTGCTG
        GCTCCAAAGCCTGTCCATGACCTTAGACTGCAGCCATTAACAATGAGGGTATGGGGCCAG
        GTGTGGTGTCTCATGCCTGTAATCCCAGCACTTTGGGAGGCTGAGGCAGGAGGAACACCT

37725   GTTGAGGCGTGGCTGGTTTCAAAGGTGACAGAGGCTTCAGGCTTCAAGGATTTGGGGCTC
        TATCCTGCAAGCAACAGTGAGCCAAGGAAGGGTTTTGAACAGGGAAAGGACAGTACATGA
        ACAGAGCTGGGAACCAAGGCTGAGAGGTAGGCAGCAGAGCAAGACCTTGAACCCAGGTCT
        TGCTGGCTCCAAAGCCTGTCCATGACCTTAGACTGCAGCCATTAACAATGAGGGTATGGG
        GCCAGGTGTGGTGTCTCATGCCTGTAATCCCAGCACTTTGGGAGGCTGAGGCAGGAGGAA
        [C,T]
        ACCTGAGGTCAGGAGTTTGGGACCAGCCTGGCTGATGTGGTGAAATGTCGTCTCTACTAA
        AAATACAAAAATTAGCCAGGCATGGTGGCGGGTCCCTGTGATCCCAGCTATTCGGGAGGC
        TGAGGCAGGAGAATTGCTTGAACCCGGGAGGCAGAGGTTGCAGTGAGCCAAGATCACGCT
        ACTGCACTCCAGCCTGGGCGACAGAGCGAGACTCCGTCTCAAAAAAAATAAAACAATGAA
        GGAAAGGTAGGCATACACCATACTGTCTGCCAGCTACCGCAGTCAGCACCCACTCCTACC

37870   GGTAGGCAGCAGAGCAAGACCTTGAACCCAGGTCTTGCTGGCTCCAAAGCCTGTCCATGA
        CCTTAGACTGCAGCCATTAACAATGAGGGTATGGGGCCAGGTGTGGTGTCTCATGCCTGT
        AATCCCAGCACTTTGGGAGGCTGAGGCAGGAGGAACACCTGAGGTCAGGAGTTTGGGACC
        AGCCTGGCTGATGTGGTGAAATGTCGTCTCTACTAAAAATACAAAAATTAGCCAGGCATG
        GTGGCGGGTCCCTGTGATCCCAGCTATTCGGGAGGCTGAGGCAGGAGAATTGCTTGAACC
        [C,T]
        GGGAGGCAGAGGTTGCAGTGAGCCAAGATCACGCTACTGCACTCCAGCCTGGGCGACAGA
```

FIGURE 3FF

```
         GCGAGACTCCGTCTCAAAAAAAATAAAACAATGAAGGAAAGGTAGGCATACACCATACTG
         TCTGCCAGCTACCGCAGTCAGCACCCACTCCTACCTAATCCCCAGGAAAGCCTGAGAGGA
         GGCTGCTATCAACAACCCCCCAATACAGATGACAAAATCAAGGCCTGGAGAAATTAGGTC
         CTTGACCTGAGATCATCGAGGGTCATTCTGTGCTAGACACTGCTCCTAACACGTTGCATA

39209    TCCCTTGCCCTCTGCAGGTGAAGCTGTGTGACTTTGGCTTTGCTCGCATCATCGGCGAGA
         AGTCGTTCCGCCGCTCAGTGGTGGGCACGCCGGCCTACCTGGCACCCGAGGTGCTGCTCA
         ACCAGGGCTACAACCGCTCGCTGGACATGTGGTCAGTGGGCGTGATCATGTACGTCAGCC
         TCAGCGGCACCTTCCCCTTTCAACGAGGATGAGGACATCAATGACCAGATCCAGAACGCCG
         CCTTCATGTACCCGGCCAGCCCCTGGAGCCACATCTCAGCTGGAGGTGCCTGGGGCCCGC
         [C,T]
         TACCCCATGGGCGGGTGGGTTGTGGGGTGGGGCTGGAGAAGTGGGCGGAGCCATGAGAGG
         GGGGTGGACCCGGAAACAGCCTGGCACCTTGGGGGTGGAGCCCAGTGCTGGGGCGGGCCT
         ACTGGAGGGATGTGGCTACAGGAGGAGCCGTCCTGTAAAAGATGGGCTGGGACTCAGGCC
         TAGACTAGGTTACTTGGGCTGGAAACCAAGTGCCCCAGAAGCGCTGAGGACACTTGGAAC
         CTTAGGGGGGCTGAGTGAGACTTGGCTTGTCTAGGGTGGGACCAGGAAAGGGACTGGACT

42934    GGTTGTGAAGGATGTAGGTTTCCTTGGGTCTGGAATGTGGCTAGGCCTCCCATTGGCTGG
         GTGCAGGAAGAGGGGGTGGAGCTAAATGTCTACTGGCTGGGTGGGTTGCAGAGGGTATGG
         CTTCACCTTCATTGGTACCCAGCTCTCAGTGGCAAACCAGAGGATATCCAGGCACTGCTC
         CAATGCAGACCCCAAGCTAACCCCAGTTCTCTCGGGCCCAGGAGTACCAGACGTGGCTGG
         ACCTCCGAGAGCTGGAGGGGAAGATGGGAGAGCGATACATCACGCATGAGAGTGACGACG
         [C,T]
         GCGCTGGGAGCAGTTTGCAGCAGAGCATCCGCTGCCTGGGTCTGGGCTGCCCACGGACAG
         GGATCTCGGTGGGGCCTGTCCACCACAGGACCACGACATGCAGGGGCTGGCGGAGCGCAT
         CAGTGTTCTCTGAGGTCCTGTGCCCTCGTCCAGCTGCTGCCCTCCACAGCGGTTCTTCAC
         AGGATCCCAGCAATGAACTGTTCTAGGGAAAGTGGCTTCCTGCCCAAACTGGATGGGACA
         CGTGGGGAGTGGGGTGGGGGGAGCTATTTCCAAGGCCCCTCCCTGTTTCCCCAGCAATTA
```

FIGURE 3GG

ISOLATED HUMAN KINASE PROTEINS, NUCLEIC ACID MOLECULES ENCODING HUMAN KINASE PROTEINS, AND USES THEREOF

This application is divisional of U.S. application Ser. No. 10/060,332, filed Feb. 1, 2002, now U.S. Pat. No. 6,528,294, which is a divisional of U.S. application Ser. No. 09/735,934, filed Dec. 14, 2000, now U.S. Pat. No. 6,372,468, issued Apr. 16, 2002, which claims priority to U.S. Provisional application No. 60/232,633, filed Sep. 14, 2000, now abandoned.

FIELD OF THE INVENTION

The present invention is in the field of kinase proteins that are related to the protein kinase C subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250-300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) J. Biol. Chem. 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) Annu. Rev. Cell. Biol. 8:463–93). Regulation of PTK activity may therefore be an important strategy in controlling some types of cancer.

Protein Kinase C

Protein kinase C (PKC) proteins are members of the STK family. Protein kinase D (PKD) proteins bind phorbol esters and diacylglycerol and are closely related to PKCs (Valverde et al., Proc Natl Acad Sci USA Aug. 30, 1994;91(18):8572–6).

Protein kinase C plays a key role in modulating cellular responses in a wide variety of extracellular receptor-mediated signal transduction pathways, and in regulating cellular differentiation and proliferation in a wide variety of cells.

Protein kinase C genes/proteins may play an important role in many cancers, and therefore may be useful for drug development and for screening for, diagnosing, preventing, and/or treating a variety of cancers. For example, tumor-specific deletions have been identified within the gene for alpha-type protein kinase C in a melanoma cell line (Linnenbach et al., Proc Natl Acad Sci USA 1988 Jan;85(1):74–8). Elevated expression levels of PKCs have been observed in certain tumor cell lines and it has been suggested that PKCs play an important role in signal transduction pathways related to growth control (Johannes et al., J Biol Chem Feb. 25, 1994;269(8):6140–8).

For a further review of PKCs, see Owczarek et al., Cytogenet. Cell Genet. 89: 240–241, 2000 and Hayashi et al., Biochim Biophys Acta May 6, 1999;1450(1):99–106.

Kinase proteins, particularly members of the protein kinase C subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the protein kinase C subfamily.

SUMMARY OF THE INVENTION

The present invention is based in part on the identification of amino acid sequences of human kinase peptides and proteins that are related to the protein kinase C subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas.

DESCRIPTION OF THE FIGURE SHEETS

FIG. 1 provides the nucleotide sequence of a cDNA molecule that encodes the kinase protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas.

FIGS. 2A–2F provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3G to provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As indicated in FIG. 3, SNPs were identified at 44 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the protein kinase C subfamily. Utilizing these sequences, additional genomic sequences were assembled and transcript and/or cDNA sequences were isolated and characterized. Based on this analysis, the present invention provides amino acid sequences of human kinase peptides and proteins that are related to the protein kinase C subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the protein kinase C subfamily and the expression pattern observed. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known protein kinase C family or subfamily of kinase proteins.

Specific Embodiments

Peptide Molecules

The present invention provides nucleic acid sequences that encode protein molecules that have been identified as being members of the kinase family of proteins and are related to the protein kinase C subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:

1) and the genomic sequences provided in FIG. 3 (SEQ ID NO:3). The amino acid sequence of such a protein is provided in FIG. 2. A protein consists of an amino-acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid-residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length preprocessed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 19 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 19 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase proteins of the present invention. SNPs were identified at 44 different nucleotide positions, including a non-synonymous coding SNP at position 42934. The change in the amino acid sequence that this SNP causes is indicated in FIG. 3 and can readily be determined using the universal genetic code and the protein sequence provided in FIG. 2 as a reference. SNPs outside the ORF and in introns may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas. A large percentage of pharmaceutical agents are being developed that modulate the activity of kinase proteins, particularly members of the protein kinase C subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Such uses can readily be determined using the information provided herein, that which is known in the art, and routine experimentation.

The proteins of the present invention (including variants and fragments that may have been disclosed prior to the present invention) are useful for biological assays related to kinases that are related to members of the protein kinase C subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent.

Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules-may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 19 (as indicated in FIG. 3), which is supported by multiple lines of evidence, such as STS and BAC map data.

FIG. 3 provides information on SNPs that have been found in the gene encoding the kinase proteins of the present invention. SNPs were identified at 44 different nucleotide positions, including a non-synonymous coding SNP at position 42934. The change in the amino acid sequence that this SNP causes is indicated in FIG. 3 and can readily be determined using the universal genetic code and the protein sequence provided in FIG. 2 as a reference. SNPs outside the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6X sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As indicated in FIG. 3, SNPs, were identified at 44 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 19 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate-compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase proteins of the present invention. SNPs were identified at 44 different nucleotide positions, including a non-synonymous coding SNP at position 42934. The change in the amino acid sequence that this SNP causes is indicated in FIG. 3 and can readily be determined using the universal genetic code and the protein sequence provided in FIG. 2 as a reference. SNPs outside the ORF and in introns may affect control/regulatory elements. The gene encoding the novel kinase protein of the present invention is located on a genome component that has been mapped to human chromosome 19 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase proteins of the present invention. SNPs were identified at 44 different nucleotide positions, including a non-synonymous coding SNP at position 42934. The change in the amino acid sequence that this SNP causes is indicated in FIG. 3 and can readily be determined using the universal genetic code and the protein sequence provided in FIG. 2 as a reference. SNPs outside the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in the lung (including fetal and carcinoid lung tissue), lymph (including mantle cell lymphomas of the lymph node), ovary tumors, kidney, colon, cervix, bone marrow, brain (including fetal), heart (including fetal), fetal liver, uterus, and pancreas. Specifically, a virtual northern blot shows expression in lung, carcinoid lung tissue, lymph, mantle cell lymphomas of the lymph node, ovary tumors, kidney, colon, and cervix. In addition, PCR-based tissue screening panels indicate expression in bone marrow, brain (including fetal), colon, heart (including fetal), kidney, lung (including fetal), fetal liver, uterus, and pancreas. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase proteins of the present invention. SNPs were identified at 44 different nucleotide positions, including a non-synonymous coding SNP at position 42934. The change in the amino acid sequence that this SNP causes is indicated in FIG. 3 and can readily be determined using the universal genetic code and the protein sequence provided in FIG. 2 as a reference. SNPs outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers; etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid-molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. Coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell Biol. 3:2156–2165 (1983)) and the pVL series (Lucklow et al., Virology 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, 1. et al. *Nature* 385:810–813 (1997) and PCT International Publication Nos. WO 97/07668 and WO 97107669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence that encodes a polypeptide comprising SEQ ID NO:2 in which residue 835 of SEQ ID NO:2 is valine, or the complement of said nucleotide sequence.

2. An isolated transcript or cDNA nucleic acid molecule comprising a nucleotide sequence that encodes a polypeptide comprising SEQ ID NO:2 in which residue 835 of SEQ ID NO:2 is valine, or the complement of said nucleotide sequence.

3. The isolated nucleic acid molecule of claim 1, further comprising a heterologous nucleotide sequence.

4. The isolated nucleic acid molecule of claim 3, wherein the heterologous nucleotide sequence encodes a heterologous amino acid sequence.

5. The isolated nucleic acid molecule of claim 2, further comprising a heterologous nucleotide sequence.

6. The isolated nucleic acid molecule of claim 5, wherein the heterologous nucleotide sequence encodes a heterologous amino acid sequence.

7. A vector comprising the nucleic acid molecule of any one of claims 1–4 and 5–6.

8. An isolated host cell containing the vector of claim 7.

9. A process for producing a polypeptide comprising culturing the host cell of claim 8 under conditions sufficient for the production of said polypeptide, and recovering said polypeptide.

10. The vector of claim 7, wherein said vector is selected from the group consisting of a plasmid, a virus, and a bacteriophage.

11. The vector of claim 7, wherein said nucleic acid molecule is inserted into said vector in proper orientation and correct reading frame such that a polypeptide comprising SEQ ID NO:2 in which residue 835 of SEQ ID NO:2 is valine is expressed by a cell transformed with said vector.

12. The vector of claim 11, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2637
<212> TYPE: DNA
<213> ORGANISM: Homo sapiens

<400> SEQUENCE: 1

```
atggccaccg ccccctctta tcccgccggg ctccctggct ctcccgggcc ggggtctcct      60 ccgcccccg gcggcctaga gctgcagtcg ccgccaccgc tactgcccca gatcccggcc     120
ccgggttccg gggtctcctt tcacatccag atcgggctga cccgcgagtt cgtgctgttg     180
cccgccgcct ccgagctggc tcatgtgaag cagctggcct gttccatcgt ggaccagaag     240
ttccctgagt gtggcttcta cggcctttac gacaagatcc tgcttttcaa acatgacccc     300
acgtcggcca acctcctgca gctggtgcgc tcgtccggag acatccagga gggcgacctg     360
gtggaggtgg tgctgtcggc ctcggccacc ttcgaggact tccagatccg cccgcacgcc     420
ctcacggtgc actcctatcg ggcgcctgcc ttctgtgatc actgcgggga gatgctcttc     480
ggcctagtgc gccagggcct caagtgcgat ggctgcgggc tgaactacca caagcgctgt     540
gccttcagca tccccaacaa ctgtagtggg gcccgcaaac ggcgcctgtc atccacgtct     600
ctggccagtg gccactcggt gcgcctcggc acctccgagt ccctgccctg cacggctgaa     660
gagctgagcc gtagcaccac cgaactcctg cctcgccgtc ccccgtcatc ctcttcctcc     720
```

```
tcttctgcct catcgtatac gggccgcccc attgagctgg acaagatgct gctctccaag      780
gtcaaggtgc cgcacacctt cctcatccac agctatacac ggcccaccgt ttgccaggct      840
tgcaagaaac tcctcaaggg cctcttccgg cagggcctgc aatgcaaaga ctgcaagttt      900
aactgtcaca acgctgcgc cacccgcgtc cctaatgact gcctggggga ggcccttatc      960
aatggagatg tgccgatgga ggaggccacc gatttcagcg aggctgacaa gagcgccctc     1020
atggatgagt cagaggactc cggtgtcatc cctggctccc actcagagaa tgcgctccac     1080
gccagtgagg aggaggaagg cgagggaggc aaggcccaga gctccctggg gtacatcccc     1140
ctaatgaggg tggtgcaatc ggtgcgacac acgacgcgga atccagcac acgctgcgg      1200 gagggttggg tggttcatta cagcaacaag gacacgctga aaagcggca ctattggcgc      1260 ctggactgca agtgtatcac gctcttccag aacaacacga ccaacagata ctataaggaa     1320
attccgctgt cagaaatcct cacggtggag tccgcccaga acttcagcct tgtgccgccg     1380
ggcaccaacc cacactgctt tgagatcgtc actgccaatg ccacctactt cgtgggcgag     1440
atgcctggcg ggactccggg tgggccaagt gggcagggg ctgaggccgc ccggggctgg     1500
gagacagcca tccgccaggc cctgatgccc gtcatccttc aggacgcacc cagcgccccca    1560 ggccacgcgc cccacagaca agcttctctg agcatctctg tgtccaacag tcagatccaa    1620
gagaatgtgg acattgccac tgtctaccag atcttccctg acgaagtgct gggctcaggg    1680
cagtttggag tggtctatgg aggaaaacac cggaagacag gccgggacgt ggcagttaag    1740
gtcattgaca aactgcgctt ccctaccaag caggagagcc agctccggaa tgaagtggcc    1800
attctgcaga gcctgcggca tcccgggatc gtgaacctgg agtgcatgtt cgagacgcct    1860
gagaaagtgt ttgtggtgat ggagaagctg catggggaca tgttggagat gatcctgtcc    1920
agtgagaagg gccggctgcc tgagcgcctc accaagttcc tcatcaccca gatcctggtg    1980
gctttgagac accttcactt caagaacatt gtccactgtg acttgaaacc agaaaacgtg    2040
ttgctggcat cagcagaccc atttcctcag gtgaagctgt gtgactttgg ctttgctcgc    2100
atcatcggcg agaagtcgtt ccgccgctca gtggtgggca cgccggccta cctggcaccc    2160
gaggtgctgc tcaaccaggg ctacaaccgc tcgctggaca tgtggtcagt gggcgtgatc    2220
atgtacgtca gcctcagcgg caccttccct ttcaacgagg atgaggacat caatgaccag    2280
atccagaacg ccgccttcat gtacccggcc agccctggga gccacatctc agctggagcc    2340
attgacctca tcaacaacct gctgcaggtg aagatgcgca aacgctacag cgtggacaaa    2400
tctctcagcc accctggtt acaggagtac cagacgtggc tggacctccg agagctggag    2460
gggaagatgg gagagcgata catcacgcat gagagtgacg acgcgcgctg ggagcagttt    2520
gcagcagagc atccgctgcc tgggtctggg ctgcccacgg acaggatct cggtggggcc    2580 tgtccaccac aggaccacga catgcagggg ctggcggagc gcatcagtgt tctctga       2637
```

<210> SEQ ID NO 2
<211> LENGTH: 878
<212> TYPE: PRT
<213> ORGANISM: Homo sapiens

<400> SEQUENCE: 2

Met Ala Thr Ala Pro Ser Tyr Pro Ala Gly Leu Pro Gly Ser Pro Gly
 1               5                  10                  15

Pro Gly Ser Pro Pro Pro Pro Gly Gly Leu Glu Leu Gln Ser Pro Pro
             20                  25                  30

Pro Leu Leu Pro Gln Ile Pro Ala Pro Gly Ser Gly Val Ser Phe His

-continued

```
                35                  40                  45
Ile Gln Ile Gly Leu Thr Arg Glu Phe Val Leu Leu Pro Ala Ala Ser
             50                  55                  60
Glu Leu Ala His Val Lys Gln Leu Ala Cys Ser Ile Val Asp Gln Lys
 65                  70                  75                  80
Phe Pro Glu Cys Gly Phe Tyr Gly Leu Tyr Asp Lys Ile Leu Leu Phe
                 85                  90                  95
Lys His Asp Pro Thr Ser Ala Asn Leu Leu Gln Leu Val Arg Ser Ser
                100                 105                 110
Gly Asp Ile Gln Glu Gly Asp Leu Val Glu Val Val Leu Ser Ala Ser
                115                 120                 125
Ala Thr Phe Glu Asp Phe Gln Ile Arg Pro His Ala Leu Thr Val His
            130                 135                 140
Ser Tyr Arg Ala Pro Ala Phe Cys Asp His Cys Gly Glu Met Leu Phe
145                 150                 155                 160
Gly Leu Val Arg Gln Gly Leu Lys Cys Asp Gly Cys Gly Leu Asn Tyr
                165                 170                 175
His Lys Arg Cys Ala Phe Ser Ile Pro Asn Asn Cys Ser Gly Ala Arg
                180                 185                 190
Lys Arg Arg Leu Ser Ser Thr Ser Leu Ala Ser Gly His Ser Val Arg
            195                 200                 205
Leu Gly Thr Ser Glu Ser Leu Pro Cys Thr Ala Glu Glu Leu Ser Arg
            210                 215                 220
Ser Thr Thr Glu Leu Leu Pro Arg Arg Pro Pro Ser Ser Ser Ser Ser
225                 230                 235                 240
Ser Ser Ala Ser Ser Tyr Thr Gly Arg Pro Ile Glu Leu Asp Lys Met
                245                 250                 255
Leu Leu Ser Lys Val Lys Val Pro His Thr Phe Leu Ile His Ser Tyr
            260                 265                 270
Thr Arg Pro Thr Val Cys Gln Ala Cys Lys Lys Leu Leu Lys Gly Leu
            275                 280                 285
Phe Arg Gln Gly Leu Gln Cys Lys Asp Cys Lys Phe Asn Cys His Lys
            290                 295                 300
Arg Cys Ala Thr Arg Val Pro Asn Asp Cys Leu Gly Glu Ala Leu Ile
305                 310                 315                 320
Asn Gly Asp Val Pro Met Glu Glu Ala Thr Asp Phe Ser Glu Ala Asp
                325                 330                 335
Lys Ser Ala Leu Met Asp Glu Ser Glu Asp Ser Gly Val Ile Pro Gly
            340                 345                 350
Ser His Ser Glu Asn Ala Leu His Ala Ser Glu Glu Glu Gly Glu
            355                 360                 365
Gly Gly Lys Ala Gln Ser Ser Leu Gly Tyr Ile Pro Leu Met Arg Val
            370                 375                 380
Val Gln Ser Val Arg His Thr Thr Arg Lys Ser Ser Thr Thr Leu Arg
385                 390                 395                 400
Glu Gly Trp Val Val His Tyr Ser Asn Lys Asp Thr Leu Arg Lys Arg
                405                 410                 415
His Tyr Trp Arg Leu Asp Cys Lys Cys Ile Thr Leu Phe Gln Asn Asn
                420                 425                 430
Thr Thr Asn Arg Tyr Tyr Lys Glu Ile Pro Leu Ser Glu Ile Leu Thr
            435                 440                 445
Val Glu Ser Ala Gln Asn Phe Ser Leu Val Pro Pro Gly Thr Asn Pro
            450                 455                 460
```

-continued

His Cys Phe Glu Ile Val Thr Ala Asn Ala Thr Tyr Phe Val Gly Glu
465                 470                 475                 480

Met Pro Gly Gly Thr Pro Gly Pro Ser Gly Gln Gly Ala Glu Ala
                485                 490                 495

Ala Arg Gly Trp Glu Thr Ala Ile Arg Gln Ala Leu Met Pro Val Ile
                500                 505                 510

Leu Gln Asp Ala Pro Ser Ala Pro Gly His Ala Pro His Arg Gln Ala
                515                 520                 525

Ser Leu Ser Ile Ser Val Ser Asn Ser Gln Ile Gln Glu Asn Val Asp
                530                 535                 540

Ile Ala Thr Val Tyr Gln Ile Phe Pro Asp Glu Val Leu Gly Ser Gly
545                 550                 555                 560

Gln Phe Gly Val Val Tyr Gly Gly Lys His Arg Lys Thr Gly Arg Asp
                565                 570                 575

Val Ala Val Lys Val Ile Asp Lys Leu Arg Phe Pro Thr Lys Gln Glu
                580                 585                 590

Ser Gln Leu Arg Asn Glu Val Ala Ile Leu Gln Ser Leu Arg His Pro
                595                 600                 605

Gly Ile Val Asn Leu Glu Cys Met Phe Glu Thr Pro Glu Lys Val Phe
610                 615                 620

Val Val Met Glu Lys Leu His Gly Asp Met Leu Glu Met Ile Leu Ser
625                 630                 635                 640

Ser Glu Lys Gly Arg Leu Pro Glu Arg Leu Thr Lys Phe Leu Ile Thr
                645                 650                 655

Gln Ile Leu Val Ala Leu Arg His Leu His Phe Lys Asn Ile Val His
                660                 665                 670

Cys Asp Leu Lys Pro Glu Asn Val Leu Leu Ala Ser Ala Asp Pro Phe
                675                 680                 685

Pro Gln Val Lys Leu Cys Asp Phe Gly Phe Ala Arg Ile Ile Gly Glu
                690                 695                 700

Lys Ser Phe Arg Arg Ser Val Val Gly Thr Pro Ala Tyr Leu Ala Pro
705                 710                 715                 720

Glu Val Leu Leu Asn Gln Gly Tyr Asn Arg Ser Leu Asp Met Trp Ser
                725                 730                 735

Val Gly Val Ile Met Tyr Val Ser Leu Ser Gly Thr Phe Pro Phe Asn
                740                 745                 750

Glu Asp Glu Asp Ile Asn Asp Gln Ile Gln Asn Ala Ala Phe Met Tyr
                755                 760                 765

Pro Ala Ser Pro Trp Ser His Ile Ser Ala Gly Ala Ile Asp Leu Ile
770                 775                 780

Asn Asn Leu Leu Gln Val Lys Met Arg Lys Arg Tyr Ser Val Asp Lys
785                 790                 795                 800

Ser Leu Ser His Pro Trp Leu Gln Glu Tyr Gln Thr Trp Leu Asp Leu
                805                 810                 815

Arg Glu Leu Glu Gly Lys Met Gly Glu Arg Tyr Ile Thr His Glu Ser
                820                 825                 830

Asp Asp Ala Arg Trp Glu Gln Phe Ala Ala Glu His Pro Leu Pro Gly
                835                 840                 845

Ser Gly Leu Pro Thr Asp Arg Asp Leu Gly Gly Ala Cys Pro Pro Gln
                850                 855                 860

Asp His Asp Met Gln Gly Leu Ala Glu Arg Ile Ser Val Leu
865                 870                 875

<210> SEQ ID NO 3
<211> LENGTH: 43950
<212> TYPE: DNA
<213> ORGANISM: Homo sapiens

<400> SEQUENCE: 3

```
cgcggcgggg agggcagggg tgacgctcgg agaacagaga ggccgaaccc agagagcggg        60
ccgggacctg ataccgattt cccacccgtc ccctgccatg ggcgccggac gcctgccgga       120
gagggctccc ctccttaaag ggccagtggc ctccaagccc gacgcctgcg accggcggtg       180
ggtgatagtg tttcccctcc ctgtccagcc gagggaaaag ttaactttcc aggcttggct       240
gtgttcaggg aaggaactgg tctcgcctgc ctgccctcca tccctcacac catcccttgt       300
cccgacccct ggaggcggag gtccagcccc caactcggag gccccgggcc caccctcccc       360
ttccgccccc ggcccctcgg caggctccgc ccctctctga cgtcgccgag gcccgcgccg       420
attggtcgac tgcactgtcg ctccggacac ttcctcctgg gccgccgccg ccgccgccga       480
cttaaacttt ggaggggaaa aagagctac tggcgcctgg cgaccctccc tgccccccac       540
ccaacccgc tccggcaacg ccccccttcct cacggctccc gaccgaactt ttctccaact       600
tctgcgactc gtgagattcc cttctaccca ctccggccct cgggacccct ctgcccatcc       660
cctgccggt cgggtccctg cgaacccctt tatctctgga atccactcgg tccccgactc       720
agagactcct gccctccacc cccaaggtga attccccccgg gccgccttct gagtgggatc       780
ctcttcttgg agcactggat cctgggattc cctctgcccc cttctcaatc cctcctctag       840
ggaaggggcc tttgaatcgc gggctctcct gatccctgtg accccgacct actagatttc       900
ctctcaggct tcttggaatc tcaatcgctg gacctccaa cccactactt ttctcctttc       960
tgatcttctg ggagccctgg attccgggcc tctgacccac tatagtgcct ttctctcctt      1020
cccaggaccc cgccatcctc aggtccctc cgcctgccag atcttttctc ggatccccgc      1080
tctcccacca cctgctcacg agatcccgcg gatctagaac ccagggtccc ccggggcccc      1140
ccggccgggt cccgggtggg ctccaggcgg ccggtcccg gcctccccccc atggccaccg      1200
cccccctctta tcccgccggg ctccctggct ctccggggcc ggggtctcct ccgccccccg      1260
gcggcctaga gctgcagtcg ccgccaccgc tactgcccca gatcccggcc cgggttccg       1320
gggtctcctt tcacatccag atcgggctga cccgcgagtt cgtgctgttg cccgccgcct      1380
ccgagctggc tcatgtgaag cagctggcct gttccatcgt ggaccagaag gtgagggcgc      1440
aggctccctg gatccagctc ggggagaggt tgaaggaggg ggcgctggca gagggtctg       1500
gggcctggtg tgcggaagag ggaggaagga gacctgagct ttgggtgatg gagggatagg      1560
gggcattgcc cccttccat tgcccctctc ccaccatcc ctttgagaga ggactgggca       1620
ggggtggggt gccccagagg cctccccaaa tttcatgtcc ctgcatgtcg ttgttttctg      1680
cagcaaacag ggaggaaggg aggggccagc caggtgtaga gaggggagga aggggcagca      1740
gatgtcggcg gacctccacg tccaggccca tcccgggcct cccatttggt ggaaacagga      1800
gaaattgaac ccgggctggc catggtgatc cggtgacatg tgtgggtgca ggtgcttgag      1860
ttagctgcca ggggcaagtg aggtctcgga gcccaattct gccctccct aagcctgaga       1920
tatgtgtgga gggcaggca ctcctacaga ccctggggac tctattccct ttcctagtca       1980
cagtgctgtt agcctactct taattttgga caccagggtc cccagggtgg gcagctggt       2040
gttatggcaa gaggaaacca ggtggaactc acgtctaaa ccgtgaaatg ttaaaagaat       2100
agtgggcttc tgtgttggag tactggactg tagaaatgtt agaatattag aatcataact      2160
```

-continued

```
tgttggaata tgcatcctag gcaattaaat tgcccccatg ttcgtgttca aatattagaa    2220
ttctaggttt gtgaaatagt aaaacattaa aatgctggaa tattagattc ctagattgtt    2280
gaatcctaga aagttaaaat gttagaattt tagaatgctg gatggatgag gtccttgaat    2340
gctaaagaat tcaaagagca cagtcctagc ttgtcagact cctagaatat aaaatatta    2400 gattaccgct tatttaggtt attgaaatcc taaaatgtat agtgatacca ggtaggaatc    2460
tagaatgtat aattctataa tgtgagcatg ttggagtccc aaaatatcca aattccagaa    2520
tcttttcaga ctcctggaaa tgaatccttt gggcatcaga gaaacgtggg gaactgggcc    2580
agctccccca ttctacagac aaggaaactg aagcttagag aaaaacttcc caagggtca    2640 gggccaaggc agtcctggtc ttctgtggac tctctcttag cagtgagaac tgataggtt    2700 ttgcccacca aatgcctaaa tcccgcaggc ccagctcacc accccaactc agcccacttc    2760
atgggaagct ggtggcagtg ggggtacggg ggcagattgt cccttgggtg aacttctttg    2820
tccagtgctc aagtccccag cctgccccgc tcaggcttca ccccagtttt attttctgc    2880 caggtccagg tgtgttaggg ccgcgtacct tccttcccga ggcccaccg gggcagtttc     2940 actttctgtt ctactaggtt tcatttcctg cccccaggcc cccaaagctg aggacccaga    3000
cacctgggtc ctttgagcat tgggtggcag gcgccctcct tatctccagc gccctcgagt    3060
ccaagtcccc cggcccccc ccccactttt cccaggagcc ccgaaaagtc ctccttccag     3120
ctcgccccac cccagtgctg ggcctggagc caggtaactg ggacaacaat agacagatcc    3180
aggaaggaag ctgggggggcg ggtgtgtgag cctggggagg aggcacaggg gagggagtgt   3240
tcattcagca tcccctccca cctccgccag gttccggaaa attcgaggtg tccacgctcc    3300
cggagccact ctccctccca ccccagctcc cccttccagc caccaaaccc acgccggcgc    3360
cccctccccg tacaattggg gcgctggcat cctgcccggc tcgcgctggg gttgggaggg    3420
ggcaggcagg aagcgagggc ctgcggggtc tctgcgtttc cggggggaaac agccggccct    3480 gccctgggag ggtcacagtc cgcccgctgc tgaaggcggc tctgagcttt tccgtcgcca    3540
catccctctc ccgcccctca gttccctgag tgtggcttct acggccttta cgacaagatc    3600
ctgcttttca acatgaccc cacgtcggcc aacctcctgc agctggtgcg ctcgtccgga    3660
gacatccagg agggcgacct ggtggaggtg gtgctgtcgg gtgagaggtg gtggccggcc    3720
tgggggcggg gcctcgggtg ggggcgggc atctggggga ggagagggta ggggagtta      3780 gaagtcagga gaggccgggt gtagtggctc acgcctgtga tcccagcact ttgggaggct    3840
gagctggagc tgggggggatc gcttgagccc aggagttcga gatcagcctg gcaacatag    3900 tgagattcca tctctacccc tttctctccc tctgaaaaaa aaaataagg agagttgggg     3960 gcttctggaa gatggttaca gagtgggtc atgaaggcgc tctttaggga ctggtctaaa    4020 cttcattta tggattagga tgctagtgac acgctttgta cagtttgaaa attcattgag     4080
ctgtgcactt gtgatgtgcg gcctttcctg aacatatgtt atacttattt atttataaaa    4140
ctagtcaagt gcagtagtta aagggggaa aagaggagaa gaaggagttg gatctgtaac     4200
tgactgtgtt atgcttaaat ataaaggtaa aaaatgggcc agctgcagtg gctcacacct    4260
gtaatcccag cagtttggga ggctgaggtg ggaggatcgc tggagcccag gagtttgaga    4320
ccagcctggg caacataagg agaccccatc tcttaaaaaa aaaaaaaaaa aaaaagtta    4380 accgggcgag gtggcacacg tctgtagtct cagctacttg ggaggctgag gtgggaggat    4440
ttcttgagct taggagtttg aggctgcagt gagccacgat catgtcactg cactccagcc    4500
```

```
tgggcaacag agagagaccc tatctctaaa aaagaaaaaa agtagaaaaa gaaaaaaaaa    4560
agttatgatg tccatggctc ctgccacgaa aatgctaaat taaatcagaa tctctgcaaa    4620
gtgagatgga atctgcacat cagtattttt aaaagccccc aggtgatttt ctaagacaca    4680
gccagaagcc agttcatcca ctcactattc cagtagtata gatgggcatg ctctcagcac    4740
cttagagcag tctatggccc ttggtccctc ttgagggtgg gggcagctgc cttttttcatg   4800 gctgtcttcc ctgctgctcc ggcatactgc agtgcccagt gaaaccggct caatgaatga    4860
atgacagaag tctggattta ccctttagt gaccttgttc aggctttaag tactctttca     4920
tatcataagc tggcctcact tgaattttta tcttcattgt tgtctctccc ctaaacctga    4980
gttttgtttt gttttgtca tttttattat ttttgtttt tttagacgga gtctcgctct       5040
gtcacccagg ctgagtgca gtggcgcaaa ctcagcttgc tgcaacctct gcctcctggg      5100
ttcaagcgat tctcctgcct cagcctcccg agtagctggg attacaggcg cctgctacca    5160
cacgtggcta atttttgtat ttttagtaga cgggatttt caccttgttg gccaggctgg     5220
tctcgaactg ctgatcttaa gtgatctgcc cacctcagcc tcccaaagtg ctgcgattac    5280
aggtgtgagc caccgctccc ggccctgtta ttttgttttg aggcagggtc ttgttctgtc    5340
acccaggctg gaatgcagtg gcatgaccac cactcactgc agcctctacc tcccagactg    5400
aagcaatcat cccgcctcag cctcctgagg tggctggact ataggcatta caggcatgca    5460
ccaccacact gggctttttt ttttttcttt tttttagac agaatcttac tctgtcaccc     5520
aggctggagt gccgtggcat gatcttggct cacggcaacc tctgcctccc gggttcaagc    5580
aattctcctg cctcagcctc ctgagtagct gggattacag gcacgcggca ccaggcctgg   5640 ctaattttg tattttagt agagacgggg tttcatcatg ttggccaggc tggtttcgaa      5700
cttctgacct caagtgatcc gcccacctgg gcctcccaaa gtgctgggat tacagatgtg    5760
agccaccggg caccgcctat ccatgttctt ttttgttgtt ggtggtggta tttttaatta    5820
aaaatttttt aatttggtaa aatatacata acataaaaat tactatttta ggccgggtgc    5880
agtggctcac gcctgtaatc ccaacacttt gagagaccga ggcgggcaga tcacctgagt    5940
cgggagtttg agaccatccc tggccaacat ggtgaaactc cgtctctact aaaaatacaa    6000
aaattagtcg ggtgtggtgg cgcatgcctg taatcccagc tactctggag gctgaggcag    6060
gagaactgct tgaacccggg aggcggactt gtggtgagcc gagatctcac tactgtactc    6120
cagcctgggt gacagagtga aactctctaa caaacacaaa caaaaaagcc cacaacattt     6180
taagcacttt taagcgtaca gttcagtaat ttaaagttca cgcacactgt tgtgcagccg    6240
gtctccagaa ctgttgtcat cttgcgaaac tgaagctcct tgcccgttaa acaactcccc    6300
aattcccgct ctgtccctgc ccagggcgta gggatatatg tgttttgttc aggggtggag    6360
ctgggatttg aacccaggca gaatgtagta tgagagcaaa tgaaggaagg aaggaaagat    6420
cacaccttgc ggctgggagc actgtgagaa atcagggaac gtgggtctg gaaaagcttt      6480 ggcctacccc gcctcaagca tccacccta ttttccgcct acagcctcgg ccaccttcga     6540
ggacttccag atccgcccgc acgccctcac ggtgcactcc tatcgggcgc ctgccttctg    6600
tgatcactgc ggggagatgc tcttcggcct agtgcgccag ggcctcaagt gcgatggtga    6660
gagctaaagg gttgggggcg gggcctgggg cgggctctg caccggggc ggagcgtaat       6720 ggtcctggca cggggacagc gtggggagga ggagcgggtc tcagagctgg gggcgcagcc    6780
taggaagtaa taatgggaag aaggatgggc ccagaagcag agcttgggga aggagtggtg    6840
gggctgggcc ggggctcagg tctaggggcg gagcctagga ggtggagctg ggagggacaa    6900
```

-continued

```
gtagggcctt aagaacagag cctaggggag cagaagggtg gcgggggaag agggtggggc      6960
ctctatcagt tagggatcaa gcagagaaac atccaggagg agatatatat tgagatattt      7020
atatgcaagg aatcagctta cagaattgtg tgggctggct aggcaactca aatctggctg      7080
ggcacagtgg gggaggccag taatcccagc actttgggag gcaaaggtag gtggatcact      7140
tgaggccagg agttcaagac cagcctgggc aacatagcaa gactctgcct gtacaaaaaa      7200
taattagcca agcatggtga cagacacttg tggtcccagc cacttgggag gctgaggcgg      7260
gaggatcact tgagcctggg agctcgacac tgtagtgagc cctgattgca ccactgcaca      7320
ccagcctggg tgacagagcg agaccctggc tcaaaaacag gaaaaggcc ggacacggtg       7380
gctcatgcct gtaatcccag cactttggga ggccgaggcg ggtggatcac gaggtcagga      7440
gattgagacc ctccctggct aacatggtga aaccccgtct ctactaaaaa tacaaaaaat      7500
tagccgacgc tggtggcaca cgcctgtagt cccagctact tgggaggctg aggcaggaga      7560
attgcttgga cctgagagga ggaggttgca gtgagccgag attgtgccac tgcactccag      7620
cctggtgata gagtgagact ccttctgaaa acagaaacaa aaacaaaaca ataaaaagaa      7680
aaagaaaaaa aaatccatcc tatcaggaag ggcaagtggg aactcaggca caagctgaag      7740
ctgatgtcca caggtggaat ttcttcatcc gaaaagtctc tgatctgctt tttaaaacat      7800
tcagctgatt gaatgagacc cacctagaac aagcaggatc acctctccca cttacagtca      7860
gctgattatg gattttcatc acatccagaa aatacctcca ctgggccggg tgcggtggct      7920
cacgcctgta atcccagcac tctggaggcc cgaggcaggt gaatcacctg aggtcaggag      7980
ttcgagacca gcctgtccaa catggtgaaa ccccgtctct actaaaaata caaaaagcc       8040
ggcgtgttgg tggacgcctg taattccagc tactcgggag gctcagtcag gagaatctct      8100
tgaacccggg aggcagagct tgcagtgagc tgagattgca ccattacact ccagcctggg      8160
caacaagagc aaaactctgt ctcaaaaaaa tgaaagaaa agaaatacc tccatggggc         8220
cttctctccc cagttcttcc tggagtcggg gaaaagctgg gttgagaagg tgaaaagaaa      8280
aaacaaacct tgactgggca cagtggttca cacctgtaac cccagcactt tggaggctga      8340
ggcaggcgga tcatgaggtc aagagattga gaccaccctg gccaacatgg tgaaacccca      8400
tctctcctaa aaatacaaaa attagcgggc gtggtggcat gtgcctatag tcccagctac      8460
ttgggaggct gaggtaggag aatcacttga acccaggaga cagaggttgc agtgagccga      8520
gatcgtgcca ctgcactcca gcctggcaac agagcgagac tccgtctcaa aaaaaaaaa      8580
acaaaaaaaa aaaacacaaa caaaccaacc ttcatggcaa catctagatt agtgtctgaa      8640
taactgtgga tctcgcctag ccaagctgac acattaacat gactatcagg gtccatctct      8700
tgtcaacctg gcacctgtct tagtttgtca gggctgcctt aacaaaatac caccctgcgt      8760
ggcttaaatg acagacattt acttctcaaa atccctggaa ttgtgagagg ctggaaagac      8820
aaagatccag attctggcag ggttctgttt ctggtgtagc ctgctttcct gccttgcaga      8880
gggccatcat ttcactgtgc gctcacatgg gacacgagag agagatccc tggtatctct       8940
tccctttata aggaaggcca ggcatggtgg ctcatgccta taatcccagc actttgggag      9000
gatggtggat cgcttgagtc caggagttcg agaccagcat gggcgacatg gtgaaacccc      9060
gtctctaaaa aatacaacaa attggccagg catggtggtg cataccctca gtcctagcta      9120
ctcaagaggc tgaggtggga ggatcacctg gcctgggag gttgaggctg cggtgagccg       9180
tgatcatgcc actgcactcc agcctaggtg acagaacacg attgtctcag gaaaaaaaaa      9240
```

```
aaaaaaaaaa aaaaaagggt caccagtccc attggattac agccacactc tttcggcctc   9300
aattaacctt aattacctcc ataaaggcac cgtctccaga tatagttgca ttggaggtta   9360
gggtttcaac ataagaattt tgggggagac acagacattt agtccataac agcacccata   9420
catatctcct taaatcatag tttaaaaata tacaggtttt cttttttgga gacagcgtct   9480
cagtctgtca cccaggctgg agtgcagtgg cgcgatctca gctcaccaca acctccactt   9540
cccaggctca agcgattctc ctgcctcagc ctaccgagta gctgggatta caggcacaca   9600
ccattactgc ccggctaatt tttgtatttc tagtagagac ggggtttcac cacgttggcc   9660
aggctggtct tgaactcctg acctcaaatg atccacccgc cttgccctcc cacagtgctg   9720
ggattacagg catgagccac cgcgcctgtc aaaacatac agttctttaa gccaagatgt   9780
ctcaaggttc agcccaagtg tcaagatcta tataggtcct ctgtccctgt tattcatgct   9840
tctgagtgag aatgttgaaa tcgggctct gcctacagat gaaggccatg tacctgcatt   9900
ggctatgagg acagatgaca ggtgaggacc atccattctg tgatgagacc ctgtggctcc   9960
atttttttgt gtgtgtgaga cagagtcttg ctccgtcacc caggatggag tgcagtggcg  10020
tggtcttggc tcactgcaac ctctacctcc tgggttcaag caattctcct gcttcagcct  10080
cccaaatagc tgggattaca ggtgcgcacc accactcctg gctaattttt gtattttag   10140
tagacggggt ttcaccatgt tggccaggct ggtttcaagt aatccaccct cctcagcctc  10200
cccaagtgct gggattacag acatgagcca ctgcgctggg ccccatgcgc ctccatttt   10260
gtatggtgtg ccctgcaatt agagccatat tcttggatgt tccattgggt attaggtctg  10320
agacagcatc tctagctccg tgggtgccac gcttgtacag aaatcctgat tctgggccag  10380
gcacggtggc tcacacctgt aatcccagca ctttgggagg ccaaggcggg cggatcatga  10440
ggtcaggagt tagagaccag cctggccaac atggtgaaac cctgtctcta ctaaaactag  10500
aaaaattagc tgggtgtggt ggcgggtacc tataatccca gctactcggg aggctgaggc  10560
aggagaatca tttgaacctg aggggtgga ggttgcagtg agccgagatc ataccattgc  10620
actccagcct gggtgacagg gtgagactcc gtctcaaaaa aaaaaaaaaa aaagaaatcc  10680
agtttctcca atatcctgtg ttccagatca tcatgcagtc caaagtatac ttgtattatt  10740
taaggactct aggcctgcag atactgattc agtgcattaa aagctcttat aaatattgcc  10800
atcgtccaca caccatatcc aactcttgag gtctcagcat atgcagtctt tgtcatgata  10860
cagccctggt gtcatcaagt cctaatgggt tatcagcaca gacttcactg gtgcagcatc  10920
acagatgatg gtcccagttc ctatggtggc aagagaaccc caaatgacta cattccgaca  10980
ggagtttaac tctatcctga gactcattct gagagttata gataagattc tgaaattctg  11040
gaaggcacat gagtgattca aggccaacac tgggaaatgg ttcctgtgtg caagaccat   11100
ttgccctgct gaagctcttc ttgcagggcc aacaccgttc tccaagcttg cctccgtgat  11160
tacagcatgc agccaagaca gtgcctacaa tgaggaggtg tggaactgga agcctggag   11220
caggcgggta ccagaagggc tcccaaaggc tggaggaaca ttcttcactc cagaatagaa  11280
agcgatcctg gaatcgtttg gaatcactgg agatgtatta gagcacacat acagaacgtc  11340
cagtgggaaa cagggagttg agctgatttc tccatggatg aggattttaa agataaaat   11400
aggcagggca cagtggctca tgcctgtaat cccaacactt tgggaggctg aggtgggagg  11460
atcacttgag cccaggagtt caagaccagc ctgggcaatg tagcgagacc ccatctctac  11520
aaaaaaataa aaataaaaaa attatctggg catggtagtg tatgtctgtg gttctggcta  11580
ctcaggaggc tgaggcagga ggattacttg agcccaggag ttgaaggctg cagtgagcta  11640
```

```
tgattgtgcc attgtgcttc agccggggt  acagggagat cctgtctcta caaaataaaa  11700
taagacaata agaagtcata cttctgccta gtatggtaca atggacctga gtacaactga  11760
gaactctttt ttttttttg  aaactgagtc tcgctgtatt gcccaggctg gagtgcagtg  11820
gcgtgatctc agctcactac aacctctgcc tcctgggttc aagtgattct cctgcctcag  11880
cctccggagt agctgggatt acaggcgtgt gccactacac ccggctaatt ttgtattttt  11940
agtagagatg gggttttgcc atgttggcca gtgtggtctc aaactcctga cctcaagtga  12000
tccgccggcc ttggcctccc aaagtgctgg gattacaggc gtgagccacc atgcgtggcc  12060
cacactacta agatttaatc acactactta gggattgcct ggattccagg tctacagaaa  12120
agagaaagtg gggtacaggg ggtgagcaga cctggaggga tagtgacctt aggggtgggg  12180
gtgaggagag gcattttctt ttggaaagtt gggggttgggg aaagaggggg aaccaagggg  12240
gcctcagaaa aaggaaggtc agggttagaa gggggaacag gtgtctctag ggagatggac  12300
aggagttttg gggaggacta aaggaggtg cttaccatag aggactgggg ctgggtcaga  12360
gctttggcgg ggacttttga ggcatccatt gttgcagtgg gaaaaggtgg ggtgtgaggc  12420
gcgttcaggg cctgggggggc agatgggtg atgtcgggc  tacaagctgg aactaggggt  12480
ggagctttgg agggaaccctt tgaggtatcc cttgttggag tgggaaaatt ttgggtgtga  12540
ggcgtgttca gggtctgggg acagatgg   gtgatggcag ggctacaagc tgaaactggg  12600
gacagagctt tgggggggagc ctttgaggtg accttgttg  gagtgagaaa aggggtgtgg  12660
gtgtgttcag ggtctgggg acagatgg    tgatggtggg gctacaagct ggaacttggg  12720
gcagaactct aaggagggt gggcctgaag gggctgatac acttacggat agtagtgcct  12780
tttggaggag atcgtgctgg cgggggtga  tgggacagga ccaggtgaga gattgggtgg  12840
aaagggcaca acttctcaag aagagaccta ggaggggcag acgccatgtc tcttactctc  12900
tggcgccccc tgcaggctgc gggctgaact accacaagcg ctgtgccttc agcatcccca  12960
acaactgtag tggggcccgc aaacggcgcc tgtcatccac gtctctggcc agtggccact  13020
cggtgcgcct cggcacctcc gagtccctgc cctgcacggc tgaagagctg gtgaggagat  13080
gggggatggg acgggttggt ggctaggggg gtgacttggc ccaggcatgg ggccaacgca  13140
ctgatgtgtc ccctccattc ttgccaatga cagagccgta gcaccaccga actcctgcct  13200
cgccgtcccc cgtcatcctc ttcctcctct tctgcctcat cgtatacggg ccgccccatt  13260
gagctggaca agatgctgct ctccaaggtc aaggtgccgc acaccttcct catccacagc  13320
tatacacggc ccaccgtttg ccaggcttgc aagaaactcc tcaagggcct cttccggcag  13380
ggcctgcaat gcaaaggtta gctgggcctg tcggggagga cagtacaggg tcagaacctc  13440
cttcccgccc caacctggtc ttgtggcagg acacaaggat ctgagccttg ggaccccagg  13500
gcctcagaag ggagggccc  tgaatcctag tgttctggga cctttggaat tctgaatct   13560
tagaacctca gttgtgtgtg tgtgtgtgtg tgtgtgtg   tgtgtgttgt gttgtttttt  13620
gaagacaggt tgtcactcta tcacccaggc tggagtgcag tggcgcaatc acggctcact  13680
gcagcttcaa cctcttgggt tcaagtgatc ctcctgcctc agcctcccaa gtagctagga  13740
ctacaggtgg tgccaccaca cccagctaat ttctttttct ttttttttt  tttgagacgg  13800
agtctcactc tgtcgcccag gctggagtgc agtggtgtga tctcgggctc actgcaaact  13860
ctgcctcctg ggatcaggac attctcctgc ctcagcctcc tgagtagctg ggactacagg  13920
cgcccgccac catgcctggc taattttttt gtattttag tagagacggg gtttcaccat  13980
```

```
gttagctagg atggtctcga tctcctgacc ttgtgatcca cctgcctcga cctcccaaaa   14040
tgccgggatt acaggcgtga gccaccgcgc ctggccacac ccagctaatt tttaaatcat   14100
ttgtagagag aaggtatcac tatattgttc aggctggtct tgaactcctg ggctcaagca   14160
atcctcctac ctcggcctcc caaagtgctg ggattacagg tgtgagccac cgcgcccagc   14220
tgaacctcag tctttagaac cttggaatcc tagattcata acgtgcttag catggaattc   14280
taaaactgta gaacctgaga attctagaat cagaaccata gcattcaaga attccgaatg   14340
atagaattca gctaaaataa caacagaact ttagattaca catcttagat ctcccaagtt   14400
atagactctc agagcatgag aattttggaa ccatgggatt tgagggtaat agaaacatag   14460
gcacatcaaa tttgagagtc ttagacgtct agaatcatat aagcttgaaa ccatcgtaac   14520
ctagaatcct ggaaattcta gactcccaga actttgaaca atcaaattct agaatccagc   14580
caggtgtggt ggctcatgca tgtaatctca gcactttggg aggccaaggt aggtggatca   14640
cttgagccta ggagtttaag accagcctgg gcaacatggt gaaaccctgt ctctacaaaa   14700
aaaattaaaa attagccagg catggcagca tgcatctgtg gttccagcta cttgggactc   14760
tgaggaggga ggattgcttg agcccaggag gttgaggctg cagtgagcca tgattgtgcc   14820
actgcattcc agcctgggtg acagagcaag aacttgtctc aaaaaaagaa aaaaaaaat   14880
tctagaacct cagaagccta gatccacata aacttagaaa catccaattc aagaatttac   14940
tggaacaatc aaattctaga atcttagaag cctagagcta agaagcata gaaacatcaa   15000
attctagaat cttgtatgta tagaatccta gaaccttgga atctgcagat tctgaggta   15060
gagaagccta gaattgtaga accctagaac tgtcaaattt tagagtttag atatataaca   15120
ccctaaaatc ttggacatta aagagtctta gaagtgttga ctcatagatg tctagagttc   15180
tagaaacttg gacatcaaac tctgaagcct tagaaatacg gaatcaggtc aggggcagta   15240
gctcacacct gtaatcccag cactttggga ggcttaggtg ggtggattgc ttgagcccag   15300
gagttcaaga ccagcttgta caacatggaa agaccccatc tctacaaaaa atacgaaaaa   15360
ttagccaggc atggtagtgc gtgcctgtag tttcagctac tcaggaggct gaggtgggaa   15420
gatcgcttga gcctgggagg cagaggttgc agtgagccga gatggtgcca ttgcacactc   15480
tagtctgggt gacagccaga ctgtttctta aaaaaaaaa aaaaaaaaa aaaccagaat   15540
catagaacct tcataaaata ggtttttagt aaactctaga atcttcgatg tatagtgtcc   15600
ctagaaccgt ggaaacactg aactctacag caatggttct cgaccagggg ccgttttgct   15660
cctagggat gttggcaag ggttggagat ggttttgttt ggtacgctgg gatagtgcta   15720
ctggcatcca gtaggtagaa gtcagagatg cagctaaaca tcctacaata cacagagcaa   15780
gtgccctaaa acaaggaatt atcctgggca ctgtgttagt gtcacgggtt gaggaaccca   15840
gccctagggt gttcagagtc tggagtcaca gcacattaga accaataaca cacacacaca   15900
cacacacaca caagtcgggc gcggtggctc acgcctgtaa tcccagcact tttaggaggc   15960
caaggcaggt ggatcatctg aggtcaggag cgcgaaacca gcctgaccaa catggcgaaa   16020
ccccgtctct actaaaaaca caaaaaaatc agctgggcgt ggtagtgggc gcctgtagtc   16080
ccacgcccag ctaatttttg tatttttagt agagacgagg ttttaccatg tagggcaggc   16140
tggtttcgaa ctcctgacct caatgatcct gctctcccg gcctcccaaa ataccgagat   16200
tacaggcggg agccactgca cccagcagtc gtcgggattt tgagtctagc cctcctactt   16260
aatcaagacc cccccgatgg ttgggaaaac tgtggctgaa agtgggaaaa tgaccagggc   16320
agcagcagcc agtgttctta cccagacagc aagagtagac tcttttgagc ctgaggctta   16380
```

```
gggtcaaggt tcaagccttc caggtaacct ctcttcccct tctcacccgt tcccttgttc    16440
cctgtcctac cagactgcaa gtttaactgt cacaaacgct gcgccacccg cgtccctaat    16500
gactgcctgg gggaggccct tatcaatgga ggtgagaggc tgggggggatg ctggggagaa    16560 aggggaaggg gcaggactgg gtggagaccc ctctgatgcc tccgtcccca cagatgtgcc    16620
gatggaggag gccaccgatt tcagcgaggc tgacaagagc gccctcatgg atgagtcaga    16680
ggactccggt gtcatccctg gctcccactc agagaatgcg ctccacgcca gtgaggagga    16740
ggaaggcgag ggaggcaagg cccagaggta tacacagaac cctccaagag accctggggg    16800
aagaccctcc tgcacagtga acctcaattt cttttttctct acaatgggct gacatcacct    16860
catatttata aattttccca gttcctgagg caaaccttttt aaagcactac aatttttttt    16920
aaataatttt ttgtttgaga cagggtctcg gtctgtcgcc caggctggtg cagtggtgca    16980
gtcttgactc actgcagcct cgaccacctg ggctcaagcg atcctgccac cttagcctct    17040
cgagtagctg ggaccacagg ctcgtccacc acacccagct aatttttgta tttctgtaga    17100
gacagggtct accctatgtt gcccaggctg gtcttgaact cctgactcct gagctcaagt    17160
gatccacccg cctcagcctc ccaaagggtc ttgctttgtt gcccactgga gtgcagtggt    17220
gtgattgtgg ctcactgtaa cctcaaactc ctgggctcag gtgatcctcc tgcctcagcc    17280
tcccgagtat ctgggactac aggatgcac tgctatccct ggctaatttt agacggcgtt    17340
tcgctcttgt tgcccaggct ggagtgcagt gatgcaattt cagttcattg caacctctgt    17400
ctcctgggtt caagcgattc tcctgcctca gcctcccaag tagctgggac tacaggcacc    17460
cgcccaggcc cagctacttt ttttgtattt ttagtagaga cagggttttg ccatgttggt    17520
caggctggtc ttgaactccc aacctcaggt aatccacctg cctcggcctc ccaaagtgct    17580
gggattacag gcatgagcca ccgcgcctga cctatattcc tcttcttttt tttttttttt    17640
tttttttaag ataggggtc ttgctatgtt gcccagggtg gtcttgaact tctgcgctca    17700
agcaatcctc ccacctcagc ctcccaaagt tctgggatta caggtgtgtg ccactgtgcc    17760
cccagcctac acatttttaa actatacacg gagttcatac ttagtcagct ccactggaat    17820
gtgagctcag gtgcatgagg gcaaggatat tttctgccct cccaggtgcc taggacagga    17880
ctggctcaga tcaggcactt cctatctggg tgtggcgtga atgtttattg agaaagcaca    17940
gttcacacag gcgctggagg gtgacagccc agatcccagc tctaccactt cacttgctag    18000
gcgcttccct gtgtgccacg gtttcctcct ggggcgatga ggtacctacc ccacggggtg    18060
ataaacctgg ggtaggggta aggggggcacc ctcacaggtg cactggaaaa tatttaatga    18120
gcacctgctg tgttcaagca cacagctatg aacaaaagag gtaaaagtct gcccttctgg    18180
agctgactgc ctcagtgggg agacagctaa taaatgcatc catagcatcg ggtattggta    18240
atggtgataa aaacaagagg agatggagaa tgggggacat gctatcttag ggtccttcaa    18300
ggagacctcg ctgaggaagt ggcagttgaa gggaggggag ggaaggagcc ttgtgggggct    18360 ctggggaaa aggcttccag gcagaggcaa cagcgagtgc aaaggccctg ggtggaggc    18420 accgtgttcc agggacagca aagagaccca tgtagctgca gcagggaggg cgaggggaag    18480
agggttggac agaaagggga tgggtaagcc agtcacagtg acgacagagt gtttcctgcg    18540
gtgcctccca acccaagcag cctgaagccg caggttccct ttctcccacg tctttcctgg    18600
gaatgcctag taacaccgtc atacactgtc aagagttgga ccttgaggga ttggggggtgg    18660 cgggtgtggg gagaggcagc ccatttcaca gatggggaaa ctgagtctca ggcaaagaga    18720
```

-continued

| | | | | |
|---|---|---|---|---|
| tgtgatcaag | gccacccagg | ttctgatcta | gcacagggat | ccagagattg ttggttccag | 18780 |
| agttgagcaa | gtcacttaat | ctctcaaatc | tcaaactcct | gacctcaagt gatcccccca | 18840 |
| cttctgcctc | ccaaagtgtt | gggattacag | gcatgagcca | ccatgcccag caggccactt | 18900 |
| aatctctgta | gaccttcctt | actgtactaa | cagcatctgc | acaaatgagg gaggtgaggc | 18960 |
| ccagagaggt | tgaatcactt | acccagtgtc | acacagctgg | ctccacaatt gctggactaa | 19020 |
| ataccaatta | gcacttactg | gaggtcctct | gtatgccagg | cactgtacta agctccgtag | 19080 |
| aaaggtttcc | attcctcata | gcatcccctt | tgggtggaca | aactgaggca tgaagaggtt | 19140 |
| aggtaatttg | ctaggcagcc | tgacttcaga | aaggcctact | acagaagccc tctcaagaat | 19200 |
| ctccttctgg | gccagcgtgg | tggctcacac | ctgtaagcac | tctgggaggc cgaggcggat | 19260 |
| ggatctcgtg | aacggattct | aagggtggga | ctaggggcag | gagttaggga aggagttgag | 19320 |
| gcaaagagtt | cgagaccagc | ctggccaaca | tggtgaaacc | tcatcactac taaaaataca | 19380 |
| aaaattagcc | agggtggtg | gcgtgcacct | aatggtcacc | gtgattgtcc cggccactca | 19440 |
| ggaggctgag | gcacgagaat | cgcttgaacc | cgggaggcag | aggttgcagt gagccgagat | 19500 |
| cgcaccactg | cattccagcc | tgggtgacag | agcgagcctc | ttaaaaacaa acaaaaagca | 19560 |
| actcccgggt | gtgtgttggg | gggaaaatgt | caaacaaac | caaacaaaca aaaacagtcc | 19620 |
| ccaactccct | agtttcccag | agatgccccc | tgcattccca | agcagcatgg tcactttctg | 19680 |
| catgtgactt | ctcacccctt | cctcttcctt | cgcagctccc | tggggtacat ccccctaatg | 19740 |
| agggtggtgc | aatcggtgcg | acacacgacg | cggaaatcca | gcaccacgct gcgggagggt | 19800 |
| tgggtggttc | attacagcaa | caaggacacg | ctggtgagtg | gccggggcgg ggccgggtac | 19860 |
| ggcggagcga | aggctggaag | aggggcggct | cagcttgagt | aggcggggct aggtgggtgg | 19920 |
| ggctggagct | aggcgcgagc | ggggccagta | gtgggctggg | ccgtgctgga ggcggggcta | 19980 |
| gaattagaag | tgtgggctgt | aagggtggga | ctacggcag | gagttaggga agacccgggg | 20040 |
| ctcagggcaa | ggtcaggggc | ggggctagag | ttaggggagg | agcttggctg gaggaagagg | 20100 |
| gctaagtggg | ggcgagtctg | gggttagggc | gtggggctg | ggctagggtt aaggctaggg | 20160 |
| gcggggctgg | ggttagggcg | tgtggtgggg | tggggttacg | gcgtgggta ggtgctagag | 20220 |
| ttacggcgtg | cacgtggtgc | tccaggcacc | tggagcccca | agcagctcca cgggataggg | 20280 |
| actgggcagg | aaagtctggc | ggttcacgtg | actcttcaaa | catctctgca gagaaagcgg | 20340 |
| cactattggc | gcctggactg | caagtgtatc | acgctcttcc | agaacaacac gaccaacaga | 20400 |
| tactataagg | taagcctccg | ggctttcagc | tccctcggac | ttcccgctgt gcccacaaac | 20460 |
| tttcccacac | ctcctcctac | ccccagttac | tccagacaga | tcctgcaaat cacaccctct | 20520 |
| gcccacccc | agcctccctg | cttccagctc | atcagcaagt | gctgcccatc cgattctggc | 20580 |
| cccaccactt | tccagccagg | gggactccgg | gcaggttccc | ttacttctca gtgcctcacg | 20640 |
| cttctcacct | gcaaaatgcc | tcaaatgcta | atactcacct | cagggctggt gcgagaattc | 20700 |
| aaagagccaa | tccactaaac | caattggctt | aaggcgtggt | atatattaag ctcccagtaa | 20760 |
| ttctaaggct | gttctcacta | ttcctttatt | ttttgttatt | tatttatttt ttgagacaga | 20820 |
| gtctcactct | gtcgcccagc | tggagtgcag | tggcgcgatc | tcggctcact gcaacctccg | 20880 |
| cttcccgggt | tcaagcgatt | ctcctgcctc | agcctccac | cctaggacta caggtgaatg | 20940 |
| ccaccacacc | cagctaattt | ttgtattttt | agtagagacg | gggtttcacc atgttggaca | 21000 |
| ggatggtctt | gatctcttga | cctcatgatc | tgccccctc | ggcctcccaa agtgctggga | 21060 |
| ttacaggcat | gagccaccgc | acccggcctc | actatttctt | tataattaat gtattgcatt | 21120 |

```
gtgtgcgtat tcgtcaccac ctcccatgcc cacactgtgt cccagccact gtcttccacc   21180
tggatggttt cagccttctc cttgcagggt ccttgcttct gacctcacaa cctctgtcat   21240 ttccccaca gccaggggga gtcttcatta aaaccgtcaa accccccagt ggctcccatt    21300
gtcttagaag taataaaacc tggtactcca gctgttacct gccctggaag cgtcttcctt   21360
gaactttcca tggctggttc cttatcatct tcccattttg ctcagaccac accatctaaa   21420
atgctgtcct tggccaggcg tggtggctca cgcctgtaat cccagcgctt tcagaggccg   21480
aggtgggcgg atcacttgag atcatgagtt cgaaaccagc ctggccaata tggtgaaacc   21540
ttgtctgtac taaaaataca aaaattagct gggcatggtg gcgggtgcct ataacccag    21600 ctacttggga ggctgaggca ggagaattgc ttgaacctgg gaggtggagg ttgcagtgag   21660
ctgagatcgc gtcactgcac tcctgcctgg gcaacagagc aagactccat ctcaaaaaaa   21720
taaaataaaa taaaatataa tgctgtcctc accatgcccc cccgacgtgt ccatgtcatc   21780
acctggtttt atgggctgcc taagtcattc attctttcct ctctcctacc tccctccttc   21840
ctcttttgac acgtttccca ccccatagtc cctgtgcctt ctgtcccgcc tgggtcccct   21900
cagcctcctt cctggttctc tgtctccatc tcattctatt ccatctgccc tccgcacaca   21960
agcggatgat gctcaaaagc cttcagtggc ttcctagggc ccttggacaa agcccaggct   22020
cttccttgtg gcccgcaaag ccctgtgtgg cctcatttcc tccatttatt atcaaacgtt   22080
tatttttgag acgagtctc gctctgtcac ccaggctgga gtgcagtggc gcgatcttgg    22140
ctcactgcaa cctccgcctc cggggttcaa gtgattcttc tgcctcagcc tcccaagtag   22200
ctaggattat aggtgtgcca ccacgcctgg ctaattttg tatttttagt agagatgggc    22260
tttcaccatg ttggtcaggc gggtctcgaa ctcctgactt tgtgatccgc ctgccttggc   22320
ctcccaaagt gttgggatta caggcatgag ccaccatgcc cagcccattt atttatttg    22380 agacaggctc ttgccctgtc tcccaggtgc agtggcatga tcatggctca ctgtaacctc   22440
tgcctccctg gctcaaatga ttctcccacc tccacagtag ctgggattac aggtgcgcac   22500
caccacacct ggctagtttt tttattttt gtagagatgg gggtctcatt gtgttgctct    22560
ggctggtctc aaactcctgg gctccagcga tctgcctgcc ttggcctccc aaagtgctgg   22620
gattacaggc ttgtggcacc atgcctaatt ttttaatttt ttgtagagct ggggtctcac   22680
tgtgttgccc aggctggtct tgaactcctg gccatctgc ccactcggc ctcccaaagt     22740 gctgggagta caggcacgag ccaccacatc cggccatcaa aatgtttatc aagcttttac   22800
tatgtccagg caccgcccca tgtgatgggg atacagcttg gcttttgagc atagcctttc   22860
cttagggcct ttgcacatgc tgttcccta ctcccttgcc aactggctgc ttcttaccctt   22920 tctggtctct gcttcaatat cacttctgcc agtaattagt attattatta ttattttga    22980 gacgaatct cactctgtcg cccaggctgg agtgcagtgg tgcgatcttg gctcattaca    23040
accaccgcct cccaggtgca agcgattttc ctgcctcagc ctcccgatta gctgggatta   23100
caggcgcaca ccaccacgcc tggctaattt ttgtattttc agtagagacg ggattttgcc   23160
atgttggcca ggctggtctc gaactcctga cctcaagtga gctgcccacc tcggccttcc   23220
aaagtgttgg gattacaggc atgagccacc gcacctggcc tctgccagta attataaaag   23280
aacagtgaga acaggcttag aattactggg aacttgtctg accactgtgc aaaccaggcc   23340
catccctatc aacatggatc ccgtgtatcc ttctgggtaa gcactagaat tccaaggtct   23400
gcctggcatc ctcacctgtg ctggttccac gtcctgcagg aaattccgct gtcagaaatc   23460
```

```
ctcacggtgg agtccgccca gaacttcagc cttgtgccgc cgggcaccaa cccacactgc    23520
tttgagatcg tcactgccaa tgccacctac ttcgtgggcg agatgcctgg cgggactccg    23580
ggtgggccaa gtgggcaggg ggctgaggcc gcccggggct gggagacagc catccgccag    23640
gccctgatgc ccgtcatcct tcaggacgca cccagcgccc caggccacgc gccccacagt    23700
aagtcctccc acctcgggtc cttgagagaa tagatctaga tgggtggggc acggttctgg    23760
ggaatggaag ggccaaagag gaaagtgggc aatggtgggg ttgagaacgc agcttctgga    23820
ctcagcaggc ctgggttcaa actctgttaa tcactcctgt taatcccagc gctttgggaa    23880
gccaaggagg aggatcact tgaggccagg agttcaagac cagcctgggc aacataatga    23940
gattccatct ctacaaaaaa taaaaacaat tagccaggtg tggtggtgca cacctgtagt    24000
tccaggtact tggaaggctg aggcaggaga attgcttgag cctgggagta gtgagtcatg    24060
attgcatcac tgcactccag tctgggtgac agagcaagac tctgtctcca aaacagaaaa    24120
aacaacaaca acaaaaatcc acaacaaatc tctgttaagc tcctggcctg atatgtggcc    24180
ctgggcatat cacttcccct ccatgagcct tgtcccaggt gctgataagt cctcatgcac    24240
ttactgagtg cctcctctgt gcgggacagt gctgggacc cagtggtggc caggacagcc    24300
caagacctgc cctcatgggg ctcagagtcc agtagggcag aatacccatc ttcagagagt    24360
gacagtccag ggtgggcagg gttgggacaa ggaagctagg gagctggagg agcccagagg    24420
ggtacctgac ccaatctggg tatataggg ggcttcctgg aggaggtgac atctgaactg    24480
agatctggag gccgaggcag ggtgagatgt gggaaagaaa atgggaggtc attttaggca    24540
gaggcaaaaa atgttgagag agtaccaggt tcccaccctc tggagcttat aatccagtgt    24600
gggtgacaga cattgatcat taacccatac aagcaacgag tgtgatgcag agcatttgcg    24660
agagtaatcc aacttggtcc taggagtgac atttgagctt acacttgagg atgaggagga    24720
tttagctaag tctaggatga aggaaagagt attcctggca ggggaaacag catatgcaga    24780
gaccagaagg cagaagagag tttgctgtat ttgaggccga gcaaggaggc cagtgtgtca    24840
ggaatagcat gttgggggta gaagtcagag gtagatgagg gtctaggcca tggcttttag    24900
gccatttaag gggctcaggc ttcttcctga gggcactggg gagccatggc agagttgtga    24960
gcagaggagg gacagggtca gtcttgtgcc tcagtaagat ccctctggtt tctctgtggg    25020
aggtgagtag gaaggggcag gattggggca aggagaccag ggaaggggct gtggggtgag    25080
gacccagagt tggggggcga gcaggggcct agactggtgg aagagagaga cattcaaatg    25140
gcagaaggat cggactttag aaatgtctgg ctctggttgg gtttgtaggg ggaaaagttc    25200
aagggaagat gcaggagtca gtctgggctt ccctccaag actcagtttc cttctctgta    25260 caatgggtc agtctgcctc ccctggtgct gagatcctgg ggtaaaatgc tcagcaaaat    25320
catctgtaac atcactcctt tagccactca gcacatctca tttactcctc ctggtggctc    25380
tatgagggag gtccttttat tattcccatt ttctagatga ggaaactgag gttcgtagtg    25440
gacaagtcac cagcctgaag ttgcacattg tatcgaacat tggattcaaa tctgggtggc    25500
ctgactccca agtctgcttt tgcaggtatg ggtggagata atcctgagcc tggagtcccc    25560
tcacctctgt ctctcccctc tccctaggac aagcttctct gagcatctct gtgtccaaca    25620
gtcagatcca agagaatgtg gtgagacttc ctgcccccac ctgatgccct ccctcccac    25680 aaaccctcct cagctctctc gtctccttga ctccccttc cccatttcca tttgcacccc    25740
tgacctgccc tgtcttcacc ctgtaggaca ttgccactgt ctaccagatc ttccctgacg    25800
aagtgctggg ctcagggcag tttggagtgg tctatggagg tgaggacact tcagagctaa    25860
```

```
cccagaggga gccccgggct gggggaagct gctgtggctc cagcccttt  tttctggctc   25920
caacccttcc tttctgattg gtcacatgct cacctcccat gttgattggc ttagctagat   25980
cctgggtgga ctgattgcag gttctccttt tctcattggg aaaaaccaat ggacattcct   26040
cctgttatta ataggaaggg taaattcggc actctgattg gtcacagagg tagattttga   26100
ttggataggg aagtagatt  ctgcactctg attgaccaca gagctagaac ctagattctg   26160
attggataga gtagattctg cattcatatt ggccacagaa ctagttccta gattctgatt   26220
ggaaaagagg gtagattctg cactctggcc acagagctag atcctagatt ctgattgaat   26280
aggagggtag attctgcatt ctgattggcc acaggtctag atcctagatt ctgattggat   26340
tggagggtag attctgcatt ctgattggcc acaggctaaa tcctagattc tgattgtatg   26400
gggcgggtgg taaattttac actttgattt gccacagagc tagatcctag agttcaatag   26460
gacaggagg  gtaacttcta cactctaaac tctaagactc agtttccttc tctgtataat   26520
agggtcagtc tgcctcccct ggtgctggtg tctctcccct gtccccagga ctcttatggg   26580
tcacacaaaa ctagatgcta gattccgact ggttataaat ccagtttccc atgttataca   26640
ttcccttctt cggagctttt tgtttgtttt ttgctttcct tctttctgcc tttactccca   26700
aggtgcacct caggtggcct tttcacgtat ctcctgggc  cttccaactc tgcccaactc   26760
tggctgtctc catggtgggg ggcagaggtt ggcagaggtg gagatactcc tgccaggact   26820
gggtggtctt gctctctcat cccccatctc ttctactccc tgtgcaggaa acaccggaa    26880
gacaggccgg gacgtggcag ttaaggtcat tgacaaactg cgcttcccta ccaagcagga   26940
gagccagctc cggaatgaag tggccattct gcaggtaacc accaggccgc cttcccttc    27000
tgcttcttcc tttcatgggc cagctgaccc agtgtagggg tggtcaggga aggcttcctg   27060
ggggagggca tgtgcatgtt gagactgaag gggagaaggt gttcttagca gagggaccag   27120
cctgtacaaa gacctggtga gagggagcat gaggttttct agaaaggagg tactgggaga   27180
tgaggccagg gaggagggcg gagccagacc ctttggactt tctcctgagg gtactggaga   27240
gccacagaag gcttttgagc aagggagggg caggatcagg tgtgtacgtt aggaaaatcc   27300
cgcaggctgc catctggagg gtgggtggaa agggaagtga ttgtagccag gaggctgagt   27360
ggggatctgg gtgggagaga ggggttaggc caggatagga ctggagaatg tgagaggggg   27420
tatggattta aagatacag  atgtgcagag ctctccccat ttctccaagc tccccctcct   27480
ccctcctgca accctgggcc tccaccagaa tttcaggatg taaagatcct tctgggccgg   27540
gcatggtggc tcacgcctgt aatcccagca ctttgggagg ctgaggtggg aggatcactt   27600
gaggccagaa gtttgagacc agcctggcca acatggcgaa accccatctc tatatttaaa   27660
tagaaagaaa aaaagatcc  ttctgggcac ctggcaggtg gggtggaggt gggcctgttc   27720
tgtcttggcc tgtgggaagc cccttccct  ctccaagtgc caatacccca gggacatcct   27780
tctccttgtt tgtcatcctc ctgctcctat acctgacccg ttggggtctg agtttgtggg   27840
ttacctgggc cctgacccg  ctccccaccc tgcagagcct gcggcatccc gggatcgtga   27900
acctggagtg catgttcgag acgcctgaga aagtgtttgt ggtgatggag aagctgcatg   27960
gggacatgtt ggagatgatc ctgtccagtg agaaggccg  gctgcctgag cgcctcacca   28020
agttcctcat cacccaggtg cgtctgccct gcccgctgcc accgcccct  ccccatcagg   28080
tgtcagcttg gagaggccct gtatgcctag ggggtcaagc agacacttgg gggagtcaca   28140
atagcagata acagaaacca tcatcaggct gggcgcagtg gctcacaccc gtaatcccag   28200
```

```
cactttggga ggcccacgag gtcaggagat cgaaaccatc ctggctaaca tggtgaaacc   28260
ctgtctctac tagaaataca aaaattagc cgggcatggt ggcaggcgcc tgtagtccca    28320
gctactcggg aggctgaggc aggagaatgg tgtgaacctg ggagatggag cttgcagtga   28380
gccgagatcg cgccactgca ctccagcccg ggcgacagag caagactcca tctcaagaaa   28440
aaaaaaaaaa aaaaaagga accataatcg tacagaagta ataataacca taatagaaaa    28500
aataagccgg gcatggtagc acgtgtctgt ggtctcagct actcaggagg ctgaggcagg   28560
aggatcactt gatcccagga gttctgtgct gatcaggtgt cctcattaag tttggcatcc   28620
atgtggtgac ctcccaggag tgggggacca ccaggttgca aagcagccca ggttggaaat   28680
ggagcaggtc aaagctctct tactgatcag tagtgggatc acatctgtga agaggcattg   28740
cactccagcc tgggcaacat agcgagaccc gcctctaaa aagaaagaaa gaaaaagaa    28800 aaataatagt gacaataaca attaaaaata aagagtatgc caggcgcggt ggctcacgcc   28860
tgtaatccca acactttggg aggccaaggc gggtggatca cctgaggtca ggagtttgag   28920
accagcctgg ccaacatggt gaaaccctgt ctctactaaa aatacaaaaa ttagctgagc   28980
atggtggcag gcacctgtaa tcatagctac ttgggaggct gaggcaggag aatcccttga   29040
gcccaggagg cagaggttac agtgagctga gatcgtgcca ttgtactcca gcctggggga   29100
caagagtgaa acttcgtctc aaaaaaaaaa aaaataataa taataataat aaagagtaat   29160
cataataata gaaaaaaata gactagcggt aatgatagct attttttatta taaaaaataa   29220 atgatcagtc aggctccctg gacctgactt gactcatcta gaaaaaggg gagtcaggca   29280 tggtgggta cacctgtaat cccagctact caggaagcta aggccagagg attgcttaag    29340
cccaggagtt tgagccagcc tgggcaacat agcaagagcc catctcaaaa acaggctggc   29400
tcatgcccgt aatcccagcg ctttgggagg ccaaggcaag aggatcgctt gaagccagga   29460
gttggagacc agcctaggcg acatagtgag atcccacctc tacaaaaagt aaaaaaaaa    29520 atagaaaacc tagctggatg tggtgcctgg tagcacatgt ctgtagtcct agctgcttgg   29580
gaggaaggga gtggagaggc tctcttgaac ctaggtggtt gaggctgcag tgagctatga   29640
ccgtgccact gcactccagc ctgggtgaca gagcgagacc gtgtctcaaa accaaacaat   29700
agaaaaaacg ggcaagcagc ccttttctc tcattcattc attcagttgg tcaacaaaca    29760
ctccctagtc cctgctctgt gcttggtccc ttgctggtca gtgttgagga cacagggatg   29820
accaatacag ccccattctt agacagtgat agctcaggtg agcagggcta ggacaaggga   29880
ggctgataat ggtgatgata ataatgtgg tcactaacat ttattgagca cttactatgt    29940
gccaagcact cttcaaactc atttaatctt catagtaacc tgtgcagtag gtgctattat   30000
tatcaatccc cttttatggt tgaagaaact gagggtcaga gacatcaaat atcttgtcca   30060
gggtcacata gctggtggga tttgaaccta ggatctttgc ttttaactag tgatgtcaaa   30120
ctcatttgtg ttacattcaa acagattttc cttgtgtgcc tgtgtgcctg tgcttttttgt   30180 ttgtttttt gagacagggt ctcgctctgt cacccgagct ggagtgcagt ggtacaatca   30240
tggctcactg cagccttgac ctcccgggtt caagcaattc tcctgcctca gcctcctgag   30300
tagctgagac aacaggcatc agccatcaca cccagctaat ttttataaag acatttttat   30360
aaagacttgc tatgttgccc aggctggtct tcaactcctg ggtcaagtg atcctcctga    30420 ctcggcctca gctcgcaaa gttctgggat tacaggtgtg agccactgtg cccggcctct   30480
gttctgcgtt tcttttttt tggtggaggt gcacattaga ttcttatcac ttatattgtt   30540
caatggtttt atcccagtgt ttgcctcttt attttatatt tagtttttat ttaccatagg   30600
```

```
gttttattta ttttattttt tatttttttt tgagacggag tcttgctcta ttgcccaggc    30660
tggagtgcag tggcaccatc tcggctcact gcaagctccg cctcccaggt tcacaccatt    30720
ctcctacctc agcctcccaa gtagctggga ctacaggtgc ccaccaccac gcccggctaa    30780
ttttttgtat tttcagtaga gacagggtct cactgtgtta accaggatgg tctcgatctc    30840
ctgacctcgt gatccacccg cctcggcctc caaagtgct gggattacag gtgtgagcca    30900
ccgcgcctgg cctattttat tttttttttt gagacaggt ctcatttgt cacccaggct    30960 ggagtgcagt ggtgtaatca tagttcactg cagcctcaaa ctcctaggct gaagcaattc    31020
tcctatctca gcctcctgag ttaactggaa ccacaggcat gagccaccac gtccagctaa    31080
tttttttttt tttttttttt aatgtttttg tagagacaag gtctcgccat gttgcccagg    31140
ctggtcttga actcctgggc tcgagcgatc ctcccatctc agtctcctga gttagctgga    31200
accacaggca tgagccatta cacctggcta attttttttt atgttttgt agagacaggg    31260 tcttgccatg ttgggtctcg aactcctggg cttaagtggt cctcttgctg cagcctccca    31320
aagttctggg ttacaggcat gagccactgc gtccagccgg ccatagagtg gaacttttac    31380
gatgttaaat atccccttgt gtggtttctg tgtttcacat ccttcctaga aaggcttcct    31440
tctggtgggt gccttgcctt cttctgagac atctctgtgg gtctcagagc catcgttgct    31500
gtgttccctt taccctggcc cagcacccct atcctctcag gcagtgtgcc tgtgtttgtc    31560
aggctggctt atgggtggg acagaaaacc cactgatgca ccctcatcca gactttatta    31620
tttatgtatt tttgagacag agtctcgctt tgttgcccag gctggagcgc agtgacacga    31680
tctcggctca ctgcaccctc tgcccctgg gttcaggtga ttctcctacc tcagcctccc    31740
gagtagctgg gattataggt gtgtgccacc atgcctggct aattttttgta attttagtag    31800 agatggggtt tcatcatgtt gcccaggcca gtctcaaact cctgacctca gtcatctgc    31860 ctgcctcagc ctcctgaagt gctgggatta caggcatgag ccatcgtgcc cggccacatc    31920
cagacttcag gtgtggaaag gaatcatggt tctcacaggt ggctgctttc agcagctgag    31980
ggggtttctc tttctggcct tcatctcttc ctctcttttt gcctgctcgc tcttctttct    32040
ctctctctct ctctctgcag atttctgctt tctgggctct tgcctgcccc acacctaagc    32100
cctgtgctaa gccctttacc tcctgagctt atgtaggcct caccaccatc ctaggaggta    32160
ggtattgtta taaaccccat tttatagatg aggaaactga ggctcaggga gttagcagtc    32220
tccctcgagg tcacagccaa gtagctttcc agccaagatt tgagtctgga tctatctagc    32280
ttccaacctg ccctctttct tttctttttt ttttttttt tttgagacga agtctcactc    32340
tgtcacccag gctggagtgc aatagtacag tctcagctca ctgcaacctc tgcctcccag    32400
gttcaaacaa ttgtcccacc tcagcctcct gagtagctgg gactacaggt gcgtcccagt    32460
acaccgggct aattttgta ttttagtag acgggggtt tcactatgtt ggccaggcta    32520
gtcttgaact tctgacctcg tgatccaccc gcctcagcct cccaaaatgc tgggattaca    32580
ggcgtgagcc accatatccg gccaatgttt ttttttttg agatggagt ctcgctctgt    32640 tgcccaggct ggagtgcagt ggcgctatct cagctcactg caacctctgc ctcccaggtt    32700
caaatgattc tcctgcctca gcctcctgag tagctgggaa cacaggcaca cgccaccatt    32760
cctggctgat ttttgtattt ttagtagaga tggggtttca ccatgtcgat caggctggtc    32820
ttgaactttt gatctcgtga tctgcccgcc tcagcctccc aaagtgctgg ggattacagg    32880
cgtaagccac cgtgcccggc ctaacctgcc ctctttgttc acatgaactg ggagaaaatc    32940
```

```
aactgacaaa atctggaaat gggcggggcg aggtggctca cgcctgtcat cctagaactt    33000
tgggaggcca aggcagatgg atcacctgag gtcaggagtt ttgagaccag cctggccaac    33060
atggtgaaat cccatcttta ctaataatac aaaaattagc caggtgtggt ggcattcacc    33120
tgtaatccca gctactgggg aggctgaggc acaagaattg cttgaacctg ggaggtggaa    33180
tttgtggtga gtcgaggtca tgccgttgca ctccagcgtg ggcaacagag tgagactcca    33240
tctcaaaaaa acaatctgga gatgacatat acaacacatg catctttcca gcttggtctc    33300
ccagtctgta gaatgaggag gttggtcagg catggtgggt cgtgcctatt atctcaaggt    33360
ttgggtagct gaggtgggaa gatcatttga ggccaggagt tttagaccag cctgggcaac    33420
atagcgagat gccatctcta caaaagatt ttttaaaaa agaaaacaat cagaataaac      33480
acaagtattt aaactctgag acagatacac aagtatttaa actccgagac agataataat    33540
tgcagttgta caacactcta tgcttctggt gtacttggca ttttgagtta cagagaatca    33600
agaaatatga ttctcacaga tgaatggtta caaatggtaa ttttttttt aatcagctca     33660 ccttatcata ggaacagata cagcaggaga agctttattt aagagacaca aacaaatata    33720
tttaccaaca agccatcaca aaaataataa ctaataacaa caacagtaac agctaacata    33780
cagtggttag ctatcctaag cgttttacat gcatctttag atatgcttta aaccttatag    33840
caacctgtaa ggttggtact cttttttttt ctgagaggca tctcactctg tcgcccaggc    33900
tggaagtgca atggcgcgat gtcgactcac tgcaacctcc acctctccag ttcaagcgat    33960
tttcctgcct cagcctcccg agtagctggg actacaggcg cccaccacca cgcctaattt    34020
ttgtattttt aatagaggca gggttttgct atgttggcca ggatggtgtc taactcctga    34080
cctcaggtga tccacctgcc tcagccttcc aaagtgctga gattacaggc atgagtcacc    34140
atgcccagcc aaagtttttt gtaaggatga aaatatttt ttttaaaaat gaaatcaggc     34200
tgggcacagt ggctcacgcc tataatccca gcactttggg aggccaaggt tggtggatca    34260
cgaggtcagg agttcaagac cagcctgacc aacatgatga aaccccgtct ctactaaaaa    34320
tacaaaaatt agccgggcat ggtggtgtgt gcctgtaatc ccagctgctc aggaggctga    34380
ggcaggagaa tcaggaggcc ttctcaaaaa aaaaaaaaa aaggaatcaa agcccgacat     34440
ggtggtggtg gcacatgcct gtagtcctag ctatttggga gactgaggct ggaggatcac    34500
ttaaccccag gagtttgagg ctgtagaatg atactgcact tcagcctggg tgacagaggg    34560
agactccatc tcttcaaaaa aaaatgggt gaggtgggg tggctcacgc ctgttatcca      34620
agcactttgg gaggctgagg tgggtggatc acttgagtgc aggagtttga gaccagcctg    34680
ggcaacatgg tgagacactg tctctacaaa tacaaaaatt agtcaggtgt gatggtgtgt    34740
gcctataatc ccagttacta gggaggttga ggtgggagga tgatttagc ctgggaggtc     34800 gaggtgcagt gagctgtgat cccgcctctg tgctctggcc tgagtgacag agcaagactc    34860
tgtctcaaaa aaaaaaaaa aaaaatag atcacatagt tggatcttgg aaatgcctgc       34920
tctgtgagta gcattcagga gtttaccaca tgctagaaga tcttgggatc ttacagcccc    34980
actcatctag cccagacttt ctagtttaca tttaactctt atctctcaga tgtaaatggt    35040
tctatgattc tgagattctt tggtgctcca gtgcctcctg tttccctggc tggggtgtct    35100
gcaggggtgt gtaggaaggc atggatgggc ccagcgcag tggctcactc acgcctgtaa     35160
tcccagcatt tgggaggcc aagtgggtg atcacttga gtccaggagt ttgagaccag       35220
cctggtcaac atggtgaaac cctgtctcta ctaaaaataa agaaaaaat tatcagagca     35280 agtctgggcc cggtggctca cgcctgtaat cccagcactt tgggaggccg aggtggggga    35340
```

```
atcacgaggt caggagtttg agaccagcct ggccaacatg gtgaaacccc atctctacta    35400
aaaatagaaa aaattagctg ggcatagtgg ccagcgcctg taatcccagc tactcgggag    35460
gctgaggcag gagactcact tgagccctgg aggtagaggt tgcagtgagc cgagatcgtg    35520
ccactgcact ccagcccagg cgacagagtg agactccgcc tcaaaaagaa aaaaaaaat    35580
tagctgggca tggtggtgca cgcctgtagt cccagctact ggggaggctg aggcaggaga    35640
atcacttgaa cccaggaggt aggggttgca gtgagctgag atcatgccac tgcacttcca    35700
gcctgggcta cagagcgaga ctctgtctca aaaaaaaaa aaaaaagta tggatgggtt    35760
tggagggctg gctgctgagg ttgggatttg gctgagtacc tatctacctt tccttactgg    35820
gcccatctgc tcccctcaga tcctggtggc tttgagacac cttcacttca agaacattgt    35880
ccactgtgac ttgaaaccag aaaacgtgtt gctggcatca gcagacccat ttcctcaggt    35940
cagttatgtc ccctcctgat ttggggaaat ccaggcaaca ctgatggccg gggtgggggt    36000
ggggaagggg attatactaa tcaagatgtg ggggcgaggc acagtggctc ttgcctgtaa    36060
tcagcatttt gagaggctga ggcaggagga tcatttgagc ccaagagttt gagaccagcc    36120
tgggcaacat agcgagacct catctataca aaaaatgaaa aaaaaaatag ccgggaatgg    36180
tggcgtgcgc ctatagtcct agctgcttag gaggctgaga tgggaggatt gcttgagccc    36240
aggagttggt ggctgcagtg agctatgatt gtgccactgc actccagcct gaataacaga    36300
gtgagactg tctcttaaaa aaaaaaaaa aagactgggt gcggtggctc acgcctgtaa    36360
tcccagcact ttgggaggcc gaggcgggca gttcacgagg tcaggagatc gagaccatcc    36420
tggctaacac ggtgaaaccc cttctctact aaaaatacaa aaaaaatta gcggggcgtg    36480
gtggtgtgtg cctgtagtcc cagctacttg ggaggctgag ttaggagaat ggcatgaacc    36540
cgggaggcgg agcttgcagt tagccgagat cacgccactg cactccagcc tgggtgacag    36600
agcgagagag cgagactctg tctcaaaaaa aaaaaaaaa atatatatat atatatat    36660
atagtttatc ccaacatata gcactttatt caacatgtag tcaacataaa aattattaag    36720
gccaggggag gtggctcatg cctataatcc ccgcactttg ggaggccaag atgggaagac    36780
ggcttgagac caggagttca agtctgaagt gagctatgat tgtgccactg cactccagct    36840
ggggtgacag agcaagaccc tgtctcttaa aaagaaaca aaactcaatg aaacattctg    36900
cttgttttc atactatgtc ttcaaaatct ggtgtgtata acagttgggg aaatagattg    36960
acatgcccaa gttgttccaa acatatttaa aagttttctg gttgggcgca gcggctcatg    37020
cctataatcc cagcactttg ggaggctgag gcgggcagat cacttgaggt ctggagttgg    37080
ataccagtct ggctaacatg gcgaaacccc gtctctacta aaaatacaaa aattagctgg    37140
gcatggtggc gggaacctgt aatcccaggt tctcaggagg ctgaagcagg agaattgctt    37200
gaacccagga gggtggaggt tgcggtgagc cgagatcaca ccactgcact ccagcctgga    37260
cgacagacca agactcgtct caaaaaata ataataaat aaaattttta aaaagatcc    37320
ataggaaagt atagatcttg gaaaagagaa agagctataa gatctgtaga aagggcagag    37380
tacctcagga aagggtggct gtcacattga gattcaggtc aggggttgag gcgtggctgg    37440
tttcaaaggt gacagaggct tcaggcttca aggatttggg gctctatcct gcaagcaaca    37500
gtgagccaag gaagggtttt gaacagggaa aggacagtac atgaacagag ctgggaacca    37560
aggctgagag gtaggcagca gagcaagacc ttgaacccag gtcttgctgg ctccaaagcc    37620
tgtccatgac cttagactgc agccattaac aatgagggta tggggccagg tgtggtgtct    37680
```

```
catgcctgta atcccagcac tttgggaggc tgaggcagga ggaacacctg aggtcaggag   37740
tttgggacca gcctggctga tgtggtgaaa tgtcgtctct actaaaaata caaaaattag   37800
ccaggcatgg tggcgggtcc ctgtgatccc agctattcgg gaggctgagg caggagaatt   37860
gcttgaaccc gggaggcaga ggttgcagtg agccaagatc acgctactgc actccagcct   37920
gggcgacaga gcgagactcc gtctcaaaaa aataaaaaca atgaaggaaa ggtaggcata   37980
caccatactg tctgccagct accgcagtca gcacccactc ctacctaatc cccaggaaag   38040
cctgagagga ggctgctatc aacaaccccc caatacagat gacaaaatca aggcctggag   38100
aaattaggtc cttgacctga gatcatcgag ggtcattctg tgctagacac tgctcctaac   38160
acgttgcata catttctctt tcagtctaaa caagcaccct ttaaggtagg gactgttaag   38220
atctccatta tgtttcatgt tttttttgtt tgtttttga gacggagtct cgctgtgtca   38280
cccaggctgg aatgcagtgg tgcgatctcg gctcactgca acctctgcct cccaggttca   38340
ggcgattctc ctgcctcagc ctcctgtagt agctgggacc gcaggcgtgt gctaattttt   38400
gtatttttag tagagatggg gtttcatcgt gttggccagg ctggtctcga actcctgacc   38460
tcaaatgatc catcttcctt ggcctcccaa agtgctgaga ttgcaggcat gagccaccac   38520
gccccaatca tgtatatttt gaggctatta aaaaaaatct gcattattca aaagaggaaa   38580
cagcgaccca ttggaggtgg cagaggtata gcagcagcta gcatttattg tgcaccaact   38640
gaatgccaaa tattgtcctg tgggctttgg atggtttaat tcactaacca tcatggcagt   38700
cctctgagat aggtgctctt ctgctcttct tcctatagat ggggaaactg aggcacagag   38760
gggggaagtc acctgcccag ggttgctcag ctagtgagcc aaggagcctg gattcaaacc   38820
agcatccagc tttctctgga ataccatgga gggtggtgtg gtggggatgc tgggggtgggt   38880 gcggctccat cacctggtgg agcctccatc ccttgccctc tgcaggtgaa gctgtgtgac   38940
tttggctttg ctcgcatcat cggcgagaag tcgttccgcc gctcagtggt gggcacgccg   39000
gcctacctgg cacccgaggt gctgctcaac cagggctaca accgctcgct ggacatgtgg   39060
tcagtgggcg tgatcatgta cgtcagcctc agcggcacct tccctttcaa cgaggatgag   39120
gacatcaatg accagatcca gaacgccgcc ttcatgtacc cggccagccc ctggagccac   39180
atctcagctg gaggtgcctg gggcccgcct accccatggg cggtgggtt gtgggtgggg   39240 gctggagaag tgggcggagc catgagaggg gggtggaccc ggaaacagcc tggcaccttg   39300
ggggtggagc ccagtgctgg ggcgggccta ctggagggat gtggctacag gaggagccgt   39360
cctgtaaaag atgggctggg actcaggcct agactaggtt acttgggctg gaaaccaagt   39420
gccccagaag cgctgaggac acttggaacc ttaggggggc tgagtgagac ttggcttgtc   39480
tagggtggga ccaggaaagg gactggactt gagggtacca aagggctgcg gtgaccagga   39540 gaagggctg agcctcccaa ggcattggct gggacctgga gcctttgggt ttacgacccc   39600
aaaagggtca gccttgcaaa aaggaggcac cggtgggtag ggttgagaaa caagggcatg   39660
gctactttgc tgtgtactgg ggccgtgact tgggtgaaga tgggcctgaa gcctggggtc   39720
ggttcagtga ccaagggagc cagtctaggg acgtggccgt ggagggtttc cgaagaggtc   39780
caggaacagg gctgaccctg agtcctggaa gctgggagtg gatgggagtg gggaggagaa   39840
gggagccagg actgaggcag acattgcact ctgcattctg gggctttggt gttgtggctg   39900
ggcctgatga agtggcaccg ggcctggtga cttgaaccta cttgggaatg ggtctgtaac   39960
tttccctgct tggaaaagtt aagtcctaag gcctggagct ttgaggctgg gtgtgggatg   40020
gcatgtttag agggccagag gcagggctaa gatactgggg tgtgtcagaa gccaggagaa   40080
```

```
caagggacct gtgttggagc cagggagctc aggaagacag atggagtatg ggaagggggg   40140
ggatcattca ttcatttatt tataaccatt tattcaacaa gtacattcat gtatttgtaa   40200
ccattgattc aacatgttga gtgcccacga tgtgccaggc attgactgtt ccagctctgg   40260
gaatactgtg atgacttgga cagaagggt caggtgcagg gtagctcatt gagtggtccg    40320
cgaagggtgg aaaggggaag gtcctctct ggagggtgcg gcttcatgga gcaggtggag    40380
cagggtgaca cggaggttgc tcggtgcagg acaagacaag gtcttggtgg tggtctaaga   40440
gcatgggccc taagcagtga gaatgtggat tgacttgagt cctggagtaa tattgggggt   40500
gctcaacact ggcttttttt ttttttttg aggtgggtc tcgctctttc acccacgctg     40560
gagtgcagtg gcgtgatctc ggctcactgc aacctccacc tcttgggttc aagggattct   40620
cctgcctcag cctcccgagt aactgggatt acaggcacac agcaccatgc ctggctcatg   40680
ttttatattt ttagtagaga cagggtttcg ccatgttagc caggctggtc ttgaactcct   40740
gacctcaagt tatttgcccg cttcagcctc ccaaagtgct gggattgcag cataagcca    40800
tcacaccccg ccagcattgt cttttgagac ccactcagaa gtccctcagt aaaagtgcat   40860
cgagtgtgca caagtgaatt taagtgtggt tgcacctgtg tgaggatcac agaatcctgt   40920
gggtgttgac gggagcaggg tgcctgtgtg caccaggcct ctcctcggat gggttcatac   40980
agtgaagcct tgtccttcat ggcttcccat caaggagaga gcctcggatg agtgctggct   41040
tgtcttgaag cttgacattc gctagtcctc ttttcacaa tgaacaggcc tatctctgag    41100
ccttctgcag gcaatggtga ctaactacca tctgatgaca ttttgttttg ttttgttttg   41160
ttttgagacg gagtttcgct tttgtcaccc gggctggagt gcagtggcac gatcttggct   41220
cactgcaacc tctgcctcct gagttcaagc gattctgcct cagcctcctg agtagctggg   41280
actacaggca tgcgctacca tgcccagcta attttttgta tttttagtag agacggggtt   41340
tccgtgttgg ccaggcttgt ctcgaactcc tgacctcggg tgatccaccc gcctcggcct   41400
cccaaagtgt tgggattaca ggcatgagcc accgcgccca gcctgatgac atagatgctc   41460
cctgatttgc actggggtta gataaacctg ataaacccat tgcccattgt aaattgaaaa   41520
tatcataagt tggtcaggcg cagtggctga agcccataat cccagcacct tgggaggcca   41580
aggtaggcag attgcttgag cccaggagtt caagaccagc ctgggcaatg tatctctaca   41640
aaaaatacaa aaattagccg gccatagtga caggtgcttg tagtcccagc tggctgctca   41700
ggaggctaag gcaggagaat caattaagct ggggaggtgg aggcttcagt gagcattgat   41760
cacgccactg cacttcagct tgggtaacaa tgagaccctg tctcaaaaaa aaaaaaggaa   41820
gtattgtagg ttgaaaatcc atttaggccg ggcgcagtgg ctcatgcctg taatcccaac   41880
aatttgggag gccaaggcag gcggattgct tgaggtcagg agttagagac cagcctggcc   41940
aatatggtga aaccccatct ctactaaaaa tacaaaaagt tagcaggaca tggtgacaca   42000
cacctgtatt cctagctact tgggaggctg aggcaggaga atcacatgaa cccgggaggc   42060
ggaggttgca gtgagccaag atcgtgccat tgcactccag cctgggcgac agagcgagac   42120
tctgtctcaa taaataaata agtaaaaata aaagaatag tacaggtgta attgtatgta     42180
cctgtatatg acaaaaagaa aaaaaaggt gacatagggg aatggggaaa ttgaagtaga    42240
gaacaggtga agagagggag ctggtgtgaa catgcatggg caggaggaga caaatttgta   42300
atgtaatgag gaaatggtg ggtgagtgat tggcacaggt gaggcttctg agccacctga    42360
gctggtgcag aaggaaggtg ttgatggcag gcaggtaggc taggggtgc ctattggagg    42420
```

-continued

```
aggagtgacc cttgacctgt agggcttgac ctgtttctct ttcctgtgca gccattgacc      42480
tcatcaacaa cctgctgcag gtgaagatgc gcaaacgcta cagcgtggac aaatctctca      42540 gccaccctg gttacaggtg atgcaggggg cagggctggc ccattggctg gattggagga       42600
aggggtggga gtagatcgct tattggctag gcaggttgtg aaggatgtag gtttccttgg      42660
gtctggaatg tggctaggcc tcccattggc tgggtgcagg aagagggggt ggagctaaat      42720
gtctactggc tgggtgggtt gcagagggta tggcttcacc ttcattggta cccagctctc      42780
agtggcaaac cagaggatat ccaggcactg ctccaatgca gaccccaagc taacccagt       42840 tctctcgggc ccaggagtac cagacgtggc tggacctccg agagctggag gggaagatgg      42900
gagagcgata catcacgcat gagagtgacg acgcgcgctg ggagcagttt gcagcagagc      42960
atccgctgcc tgggtctggg ctgcccacgt acagggatct cggtggggcc tgtccaccac      43020
aggaccacga catgcagggg ctggcggagc gcatcagtgt tctctgaggt cctgtgccct      43080
cgtccagctg ctgccctcca cagcggttct tcacaggatc ccagcaatga actgttctag      43140
ggaaagtggc ttcctgccca aactggatgg gacacgtggg gagtggggtg ggggagcta      43200 tttccaaggc ccctccctgt ttccccagca attaaaacgg actcatctct ggccccatgg      43260
ccttgatctc agcacacggc actctcgaat cattactctg ttgtaccaac atggagttca     43320
tctggaagga ggactgcctg aaaagaggaa ggatggaagg ggtggggaga gaggactgat      43380
gggagaggag tcttggaagg aggacgagct ggggtagaaa atatacagga agagtgccag      43440
gagagaagat gagaagggag agggaggagt aatggaggag gagttggaaa ctggggagag      43500
atggaaggaa tgtgactgga gggtagagaa cttggagaaa aagtaatctc atggtttgtg      43560
atgactgatt tttatttggt ggtggtgtt actactaatc acaactatta attcaggctg       43620
ggtgtggtgg ctcatgccta taatcccagc aatttgggag gccgaggcag gcagatccct      43680
tagatctcag gagtttgaga gcagcctggc caacgtggtg aaactccctt tctacaaaaa      43740
gttcaaaaat tagccaagtg tggtggcttg cacctgtggt cccagctact tggaggttga     43800
ggctagagga tcgcttgagc ccaggaagca gagattgcag tgagccaaga tcacacacca      43860
ctgcactcta gcctgggcaa gagagtgaga ccctgtctca aaagtcaaat aataaaatgc      43920
agttagccca agtctgatcc atactagaaa                                       43950
```

<210> SEQ ID NO 4
<211> LENGTH: 894
<212> TYPE: PRT
<213> ORGANISM: Homo sapiens
<400> SEQUENCE: 4

```
Ala Ala Ala Ala Ala Ala Ala Leu Val Pro Gly Ser Gly Pro Gly
 1               5                  10                  15

Pro Ala Pro Phe Leu Ala Pro Val Ala Ala Pro Val Gly Gly Ile Ser
             20                  25                  30

Phe His Leu Gln Ile Gly Leu Ser Arg Glu Pro Val Leu Leu Leu Gln
         35                  40                  45

Asp Ser Ser Gly Asp Tyr Ser Leu Ala His Val Arg Glu Met Ala Cys
     50                  55                  60

Ser Ile Val Asp Gln Lys Phe Pro Glu Cys Gly Phe Tyr Gly Met Tyr
 65                  70                  75                  80

Asp Lys Ile Leu Leu Phe Arg His Asp Pro Thr Ser Glu Asn Ile Leu
                 85                  90                  95

Gln Leu Val Lys Ala Ala Ser Asp Ile Gln Glu Gly Asp Leu Ile Glu
```

```
            100                 105                 110
Val Val Leu Ser Arg Ser Ala Thr Phe Glu Asp Phe Gln Ile Arg Pro
        115                 120                 125
His Ala Leu Phe Val His Ser Tyr Arg Ala Pro Ala Phe Cys Asp His
        130                 135                 140
Cys Gly Glu Met Leu Trp Gly Leu Val Arg Gln Gly Leu Lys Cys Glu
145                 150                 155                 160
Gly Cys Gly Leu Asn Tyr His Lys Arg Cys Ala Phe Lys Ile Pro Asn
                165                 170                 175
Asn Cys Ser Gly Val Arg Arg Arg Leu Ser Asn Val Ser Leu Thr
                180                 185                 190
Gly Val Ser Thr Ile Arg Thr Ser Ser Ala Glu Leu Ser Thr Ser Ala
                195                 200                 205
Pro Asp Glu Pro Leu Leu Gln Lys Ser Pro Ser Glu Ser Phe Ile Gly
        210                 215                 220
Arg Glu Lys Arg Ser Asn Ser Gln Ser Tyr Ile Gly Arg Pro Ile His
225                 230                 235                 240
Leu Asp Lys Ile Leu Met Ser Lys Val Lys Val Pro His Thr Phe Val
                245                 250                 255
Ile His Ser Tyr Thr Arg Pro Thr Val Cys Gln Tyr Cys Lys Lys Leu
                260                 265                 270
Leu Lys Gly Leu Phe Arg Gln Gly Leu Gln Cys Lys Asp Cys Arg Phe
                275                 280                 285
Asn Cys His Lys Arg Cys Ala Pro Lys Val Pro Asn Asn Cys Leu Gly
                290                 295                 300
Glu Val Thr Ile Asn Gly Asp Leu Leu Ser Pro Gly Ala Glu Ser Asp
305                 310                 315                 320
Val Val Met Glu Glu Gly Ser Asp Asp Asn Asp Ser Glu Arg Asn Ser
                325                 330                 335
Gly Leu Met Asp Asp Met Glu Glu Ala Met Val Gln Asp Ala Glu Met
                340                 345                 350
Ala Met Ala Glu Cys Gln Asn Asp Ser Gly Glu Met Gln Asp Pro Asp
        355                 360                 365
Pro Asp His Glu Asp Ala Asn Arg Thr Ile Ser Pro Ser Thr Ser Asn
        370                 375                 380
Asn Ile Pro Leu Met Arg Val Val Gln Ser Val Lys His Thr Lys Arg
385                 390                 395                 400
Lys Ser Ser Thr Val Met Lys Glu Gly Trp Met Val His Tyr Thr Ser
                405                 410                 415
Lys Asp Thr Leu Arg Lys Arg His Tyr Trp Arg Leu Asp Ser Lys Cys
                420                 425                 430
Ile Thr Leu Phe Gln Asn Asp Thr Gly Ser Arg Tyr Tyr Lys Glu Ile
                435                 440                 445
Pro Leu Ser Glu Ile Leu Ser Leu Glu Pro Val Lys Thr Ser Ala Leu
        450                 455                 460
Ile Pro Asn Gly Ala Asn Pro His Cys Phe Glu Ile Thr Thr Ala Asn
465                 470                 475                 480
Val Val Tyr Tyr Val Gly Glu Asn Val Val Asn Pro Ser Ser Pro Ser
                485                 490                 495
Pro Asn Asn Ser Val Leu Thr Ser Gly Val Gly Ala Asp Val Ala Arg
                500                 505                 510
Met Trp Glu Ile Ala Ile Gln His Ala Leu Met Pro Val Ile Pro Lys
        515                 520                 525
```

```
Gly Ser Ser Val Gly Thr Gly Thr Asn Leu His Arg Asp Ile Ser Val
    530             535                 540

Ser Ile Ser Val Ser Asn Cys Gln Ile Gln Glu Asn Val Asp Ile Ser
545             550                 555                 560

Thr Val Tyr Gln Ile Phe Pro Asp Glu Val Leu Gly Ser Gly Gln Phe
                565                 570                 575

Gly Ile Val Tyr Gly Gly Lys His Arg Lys Thr Gly Arg Asp Val Ala
            580                 585                 590

Ile Lys Ile Ile Asp Lys Leu Arg Phe Pro Thr Lys Gln Glu Ser Gln
        595                 600                 605

Leu Arg Asn Glu Val Ala Ile Leu Gln Asn Leu His His Pro Gly Val
    610                 615                 620

Val Asn Leu Glu Cys Met Phe Glu Thr Pro Glu Arg Val Phe Val Val
625             630                 635                 640

Met Glu Lys Leu His Gly Asp Met Leu Glu Met Ile Leu Ser Ser Glu
                645                 650                 655

Lys Gly Arg Leu Pro Glu His Ile Thr Lys Phe Leu Ile Thr Gln Ile
            660                 665                 670

Leu Val Ala Leu Arg His Leu His Phe Lys Asn Ile Val His Cys Asp
        675                 680                 685

Leu Lys Pro Glu Asn Val Leu Leu Ala Ser Ala Asp Pro Phe Pro Gln
    690                 695                 700

Val Lys Leu Cys Asp Phe Gly Phe Ala Arg Ile Ile Gly Glu Lys Ser
705             710                 715                 720

Phe Arg Arg Ser Val Val Gly Thr Pro Ala Tyr Leu Ala Pro Glu Val
                725                 730                 735

Leu Arg Asn Lys Gly Tyr Asn Arg Ser Leu Asp Met Trp Ser Val Gly
            740                 745                 750

Val Ile Ile Tyr Val Ser Leu Ser Gly Thr Phe Pro Phe Asn Glu Asp
        755                 760                 765

Glu Asp Ile His Asp Gln Ile Gln Asn Ala Ala Phe Met Tyr Pro Pro
    770                 775                 780

Asn Pro Trp Lys Glu Ile Ser His Glu Ala Ile Asp Leu Ile Asn Asn
785             790                 795                 800

Leu Leu Gln Val Lys Met Arg Lys Arg Tyr Ser Val Asp Lys Thr Leu
                805                 810                 815

Ser His Pro Trp Leu Gln Asp Tyr Gln Thr Trp Leu Asp Leu Arg Glu
            820                 825                 830

Leu Glu Cys Lys Ile Gly Glu Arg Tyr Ile Thr His Glu Ser Asp Asp
        835                 840                 845

Leu Arg Trp Glu Lys Tyr Ala Gly Glu Gln Arg Leu Gln Tyr Pro Thr
    850                 855                 860

His Leu Ile Asn Pro Ser Ala Ser His Ser Asp Thr Pro Glu Thr Glu
865             870                 875                 880

Glu Thr Glu Met Lys Ala Leu Gly Glu Arg Val Ser Ile Leu
                885                 890
```